(12) United States Patent
Clifford et al.

(10) Patent No.: US 9,700,419 B2
(45) Date of Patent: Jul. 11, 2017

(54) EXTRA-ARTICULAR IMPLANTABLE MECHANICAL ENERGY ABSORBING SYSTEMS AND IMPLANTATION METHOD

(75) Inventors: Anton G. Clifford, Mountain View, CA (US); Mary O'Connell, Menlo Park, CA (US); Joshua Makower, Los Altos, CA (US); Richard G. Vecchiotti, Redwood City, CA (US)

(73) Assignee: MOXIMED, INC., Hayward, CA (US)

( * ) Notice: Subject to any disclaimer, the term of this patent is extended or adjusted under 35 U.S.C. 154(b) by 1613 days.

(21) Appl. No.: 12/605,564

(22) Filed: Oct. 26, 2009

(65) Prior Publication Data

US 2010/0114322 A1  May 6, 2010

Related U.S. Application Data

(63) Continuation of application No. 11/775,139, filed on Jul. 9, 2007, now Pat. No. 7,611,540.

(51) Int. Cl.
| | |
|---|---|
| *A61F 2/38* | (2006.01) |
| *A61B 17/68* | (2006.01) |
| *A61B 17/70* | (2006.01) |
| *A61F 2/08* | (2006.01) |
| A61B 17/15 | (2006.01) |
| A61B 17/04 | (2006.01) |

(Continued)

(52) U.S. Cl.
CPC ............ *A61F 2/3836* (2013.01); *A61B 17/68* (2013.01); *A61B 17/7028* (2013.01); *A61B 17/7044* (2013.01); *A61F 2/08* (2013.01); *A61F 2/0811* (2013.01); *A61F 2/3854* (2013.01); *A61B 17/0482* (2013.01); *A61B 17/154* (2013.01); *A61B 17/6425* (2013.01); *A61B 2017/567* (2013.01); *A61F 2002/0823* (2013.01); *A61F 2002/0864* (2013.01); *A61F 2002/0888* (2013.01); *Y10S 623/914* (2013.01)

(58) Field of Classification Search
CPC ............................ A61F 2/3836; A61F 2/3854
USPC ............................... 623/13.12, 20.21, 20.22
See application file for complete search history.

(56) References Cited

U.S. PATENT DOCUMENTS

| | | |
|---|---|---|
| 2,632,440 A | 3/1953 | Hauser |
| 2,877,033 A | 3/1959 | Koetke |

(Continued)

FOREIGN PATENT DOCUMENTS

| | | |
|---|---|---|
| CA | 1205602 | 6/1986 |
| DE | 19855254 | 6/2000 |

(Continued)

OTHER PUBLICATIONS

Lapinskaya, Valentina Spiridovna, "Treatment of Diseases and Injuries of Hip Joint Using a Method of Distractions", Kuibyshev Medial Institute, 1990.

(Continued)

*Primary Examiner* — Bruce E Snow
*Assistant Examiner* — Melissa Hoban
(74) *Attorney, Agent, or Firm* — Adam J. Cermak; Cermak Nakajima & McGowan LLP

(57) ABSTRACT

A system and method for sharing and absorbing energy between body parts. In one aspect, the method involves identifying link pivot locations, fixing base components and minimally invasive insertion techniques. In one particular aspect, the system facilitates absorbing energy between members forming a joint such as between articulating bones.

12 Claims, 60 Drawing Sheets

(51) Int. Cl.
*A61B 17/64* (2006.01)
*A61B 17/56* (2006.01)

(56) References Cited

U.S. PATENT DOCUMENTS

| | | |
|---|---|---|
| 3,242,922 A | 3/1966 | Thomas |
| 3,648,294 A | 3/1972 | Shahrestani |
| 3,681,786 A | 8/1972 | Lynch |
| 3,779,654 A | 12/1973 | Horne |
| 3,875,594 A | 4/1975 | Swanson |
| 3,902,482 A | 9/1975 | Taylor |
| 3,988,783 A | 11/1976 | Treace |
| 4,054,955 A | 10/1977 | Seppo |
| 4,187,841 A | 2/1980 | Knutson |
| 4,246,660 A | 1/1981 | Wevers |
| 4,308,863 A | 1/1982 | Fischer |
| 4,353,361 A | 10/1982 | Foster |
| 4,501,266 A | 2/1985 | McDaniel |
| 4,570,625 A | 2/1986 | Harris |
| 4,576,158 A | 3/1986 | Boland |
| 4,621,627 A | 11/1986 | DeBastiani et al. |
| 4,637,382 A | 1/1987 | Walker |
| 4,696,293 A | 9/1987 | Ciullo |
| 4,759,765 A | 7/1988 | Van Kampen |
| 4,776,851 A | 10/1988 | Bruchman et al. |
| 4,846,842 A | 7/1989 | Connolly et al. |
| 4,863,471 A | 9/1989 | Mansat |
| 4,871,367 A | 10/1989 | Christensen et al. |
| 4,873,967 A | 10/1989 | Sutherland |
| 4,883,486 A | 11/1989 | Kapadia et al. |
| 4,923,471 A | 5/1990 | Morgan |
| 4,942,875 A | 7/1990 | Hlavacek et al. |
| 4,943,053 A | 7/1990 | Smith |
| 4,959,065 A | 9/1990 | Arnett et al. |
| 4,988,349 A | 1/1991 | Pennig |
| 5,002,574 A | 3/1991 | May et al. |
| 5,011,497 A | 4/1991 | Persson et al. |
| 5,019,077 A | 5/1991 | De Bastiani et al. |
| 5,026,372 A | 6/1991 | Sturtzkopf et al. |
| 5,037,426 A | 8/1991 | Goble et al. |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,282,867 A * | 2/1994 | Mikhail ............... 623/13.12 |
| 5,314,478 A | 5/1994 | Oka et al. |
| 5,318,567 A | 6/1994 | Vichard |
| 5,352,190 A | 10/1994 | Fischer |
| 5,375,823 A | 12/1994 | Navas |
| 5,405,347 A | 4/1995 | Lee et al. |
| 5,415,661 A | 5/1995 | Holmes |
| 5,443,518 A | 8/1995 | Insall |
| 5,456,722 A | 10/1995 | McLeod et al. |
| 5,540,688 A | 7/1996 | Navas |
| 5,564,437 A | 10/1996 | Bainville et al. |
| 5,575,819 A | 11/1996 | Amis |
| 5,578,038 A | 11/1996 | Slocum |
| 5,601,553 A | 2/1997 | Trebing et al. |
| 5,624,440 A | 4/1997 | Huebner |
| 5,662,648 A | 9/1997 | Faccioli et al. |
| 5,662,650 A | 9/1997 | Bailey et al. |
| 5,681,313 A | 10/1997 | Diez |
| 5,695,496 A | 12/1997 | Orsak et al. |
| 5,716,357 A | 2/1998 | Rogozinski |
| 5,803,924 A | 9/1998 | Oni et al. |
| 5,830,216 A | 11/1998 | Insall et al. |
| 5,873,843 A | 2/1999 | Draper |
| 5,928,234 A | 7/1999 | Manspeizer |
| 5,976,125 A | 11/1999 | Graham |
| 5,976,136 A | 11/1999 | Bailey |
| 6,036,691 A | 3/2000 | Richardson |
| 6,080,196 A | 6/2000 | Bertin |
| 6,113,637 A | 9/2000 | Gill et al. |
| 6,132,433 A | 10/2000 | Whelan |
| 6,139,550 A | 10/2000 | Michelson |
| 6,162,223 A | 12/2000 | Orsak et al. |
| 6,176,860 B1 | 1/2001 | Howard |
| 6,193,225 B1 | 2/2001 | Watanabe |
| 6,205,411 B1 | 3/2001 | DiGioia, III et al. |
| 6,206,880 B1 | 3/2001 | Karladani |
| 6,264,696 B1 | 7/2001 | Reigner et al. |
| 6,277,124 B1 | 8/2001 | Haag |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,395,005 B1 | 5/2002 | Lovell |
| 6,402,750 B1 | 6/2002 | Atkinson et al. |
| 6,409,729 B1 | 6/2002 | Martinelli et al. |
| 6,482,232 B1 | 11/2002 | Boucher et al. |
| 6,494,914 B2 | 12/2002 | Brown et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,599,322 B1 | 7/2003 | Amrich et al. |
| 6,620,332 B2 | 9/2003 | Amrich |
| 6,623,486 B1 | 9/2003 | Weaver et al. |
| 6,663,631 B2 | 12/2003 | Kuntz |
| 6,692,497 B1 | 2/2004 | Tormala et al. |
| 6,692,498 B1 | 2/2004 | Niiranen et al. |
| 6,726,684 B1 | 4/2004 | Woloszko |
| 6,752,831 B2 | 6/2004 | Sybert et al. |
| 6,884,242 B2 | 4/2005 | LeHuec et al. |
| 6,966,910 B2 | 11/2005 | Ritland |
| 6,972,020 B1 | 12/2005 | Grayson et al. |
| 6,997,940 B2 | 2/2006 | Bonutti |
| 7,018,418 B2 | 3/2006 | Amrich et al. |
| 7,029,475 B2 | 4/2006 | Panjabi |
| 7,097,662 B2 | 8/2006 | Evans, III et al. |
| 7,104,996 B2 | 9/2006 | Bonutti |
| 7,128,744 B2 | 10/2006 | Weaver et al. |
| 7,141,073 B2 | 11/2006 | May et al. |
| 7,153,327 B1 | 12/2006 | Metzger |
| 7,188,626 B2 | 3/2007 | Foley et al. |
| 7,201,728 B2 | 4/2007 | Sterling |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,247,157 B2 | 7/2007 | Prager et al. |
| 7,252,670 B2 | 8/2007 | Morrison et al. |
| 7,261,739 B2 | 8/2007 | Ralph et al. |
| 7,273,481 B2 | 9/2007 | Lombardo et al. |
| 7,276,070 B2 | 10/2007 | Muckter |
| 7,282,065 B2 | 10/2007 | Kirschman |
| 7,285,134 B2 | 10/2007 | Berry et al. |
| 7,288,094 B2 | 10/2007 | Lindemann et al. |
| 7,288,095 B2 | 10/2007 | Baynham et al. |
| 7,291,150 B2 | 11/2007 | Graf |
| 7,306,605 B2 | 12/2007 | Ross |
| 7,322,983 B2 | 1/2008 | Harris |
| 7,322,984 B2 | 1/2008 | Doubler et al. |
| 7,341,589 B2 | 3/2008 | Weaver et al. |
| 7,361,196 B2 | 4/2008 | Fallin et al. |
| 2001/0020143 A1 | 9/2001 | Stark et al. |
| 2002/0095154 A1 | 7/2002 | Atkinson et al. |
| 2002/0107570 A1 | 8/2002 | Sybert et al. |
| 2002/0151903 A1 | 10/2002 | Takei et al. |
| 2002/0151978 A1 | 10/2002 | Zacouto et al. |
| 2003/0149436 A1 | 8/2003 | McDowell |
| 2003/0216809 A1 | 11/2003 | Ferguson |
| 2004/0019382 A1 | 1/2004 | Amirouche et al. |
| 2004/0039395 A1 | 2/2004 | Coon et al. |
| 2004/0044295 A1 | 3/2004 | Reinert et al. |
| 2004/0078042 A1 | 4/2004 | Masini |
| 2004/0152970 A1 | 8/2004 | Hunter et al. |
| 2004/0260302 A1 | 12/2004 | Manspeizer |
| 2004/0267179 A1 | 12/2004 | Lean |
| 2005/0049708 A1 | 3/2005 | Atkinson et al. |
| 2005/0056979 A1 | 3/2005 | Studer et al. |
| 2005/0085815 A1 | 4/2005 | Harms et al. |
| 2005/0101966 A1 | 5/2005 | Lavallee |
| 2005/0113927 A1 * | 5/2005 | Malek ............... 623/17.16 |
| 2005/0119744 A1 | 6/2005 | Buskirk et al. |

(56) References Cited

U.S. PATENT DOCUMENTS

| | | | |
|---|---|---|---|
| 2005/0154390 A1 | 7/2005 | Biedermann et al. |
| 2005/0192674 A1 | 9/2005 | Ferree |
| 2005/0197569 A1 | 9/2005 | McCombs |
| 2005/0251065 A1 | 11/2005 | Henning et al. |
| 2005/0251080 A1 | 11/2005 | Hyde |
| 2005/0261680 A1 | 11/2005 | Draper |
| 2006/0036240 A1 | 2/2006 | Colleran et al. |
| 2006/0064169 A1 | 3/2006 | Ferree |
| 2006/0178744 A1 | 8/2006 | de Villiers et al. |
| 2006/0189983 A1 | 8/2006 | Fallin et al. |
| 2006/0282023 A1 | 12/2006 | Leitner |
| 2007/0043356 A1 | 2/2007 | Timm et al. |
| 2007/0106299 A1 | 5/2007 | Manspeizer |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0198088 A1 | 8/2007 | Biedermann et al. |
| 2007/0198091 A1 | 8/2007 | Boyer et al. |
| 2007/0244483 A9 | 10/2007 | Winslow et al. |
| 2007/0244488 A1 | 10/2007 | Metzger et al. |
| 2007/0244565 A1 | 10/2007 | Stchur |
| 2007/0288014 A1 | 12/2007 | Shadduck et al. |
| 2008/0015591 A1 | 1/2008 | Castaneda et al. |
| 2008/0015592 A1 | 1/2008 | Long et al. |
| 2008/0015593 A1 | 1/2008 | Pfefferle et al. |
| 2008/0044449 A1 | 2/2008 | McKay |
| 2008/0071373 A1 | 3/2008 | Molz et al. |
| 2008/0071375 A1 | 3/2008 | Carver et al. |
| 2008/0097434 A1 | 4/2008 | Moumene et al. |
| 2008/0097441 A1 | 4/2008 | Hayes et al. |
| 2008/0132954 A1 | 6/2008 | Sekhon et al. |
| 2008/0154378 A1 | 6/2008 | Pelo |
| 2009/0228045 A1 | 9/2009 | Hayes et al. |

FOREIGN PATENT DOCUMENTS

| | | |
|---|---|---|
| EP | 0383419 | 8/1990 |
| EP | 0953317 | 4/1999 |
| EP | 1770302 | 4/2007 |
| EP | 1429675 | 10/2007 |
| EP | 1682020 | 10/2007 |
| EP | 1847228 | 10/2007 |
| EP | 1847229 | 10/2007 |
| EP | 1005290 | 2/2008 |
| EP | 1468655 | 5/2008 |
| GB | 1507953 | 4/1978 |
| GB | 2223406 | 4/1990 |
| GB | 2250919 | 10/1993 |
| JP | 59-131348 | 7/1984 |
| JP | 7-100159 | 4/1995 |
| JP | 2532346 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007-170969 | 7/2007 |
| RU | 578063 | 11/1977 |
| RU | 578957 | 11/1977 |
| RU | 624613 | 8/1978 |
| RU | 640740 | 1/1979 |
| RU | 704605 | 12/1979 |
| RU | 719612 | 3/1980 |
| RU | 741872 | 7/1980 |
| RU | 1186204 | 10/1985 |
| RU | 1251889 | 8/1986 |
| RU | 1316666 | 6/1987 |
| RU | 1588404 | 8/1990 |
| RU | 1699441 | 12/1991 |
| RU | 1769868 | 10/1992 |
| RU | 2085148 | 7/1997 |
| RU | 2217105 | 11/2003 |
| RU | 2241400 | 9/2004 |
| SU | 1251889 | 8/1986 |
| WO | WO91/07137 | 5/1991 |
| WO | WO94/06364 | 3/1994 |
| WO | WO96/19944 | 7/1996 |
| WO | WO2004/019831 | 3/2004 |
| WO | WO2004/024037 | 3/2004 |
| WO | WO2007/056645 | 5/2005 |
| WO | WO2006/045091 | 4/2006 |
| WO | WO2006/049993 | 5/2006 |
| WO | WO2006/110578 | 10/2006 |
| WO | WO2007/090009 | 8/2007 |
| WO | WO2007/090015 | 8/2007 |
| WO | WO2007/090017 | 8/2007 |
| WO | WO2007/106962 | 9/2007 |
| WO | WO2007/109132 | 9/2007 |
| WO | WO2007/109140 | 9/2007 |
| WO | WO2007/109417 | 9/2007 |
| WO | WO2007/109436 | 9/2007 |
| WO | WO2007/114769 | 10/2007 |
| WO | WO2007/117571 | 10/2007 |
| WO | WO2008/006098 | 1/2008 |

OTHER PUBLICATIONS

Larionov d. Yu, et al., "Medical Devices", Scientific and Technical Bimonthly Journal, May-Jun. 2008.
Lapinskaya, V.S., et al., "An Endoapparatus for Restoration of the Hip Joint", Writers Collective, 2008, UDK 615.472.03:616,728.2-089.28.
Lentsner, A.A., et al., "Device for Functional Relief of Hip Joint in Cotyloid Cavity Fracture Cases", Ortop Travmatol Protez. Apr. 1990 (4) 44-6.
Orthofix; "Gentle Limb Deformity Correction", website pages, http://www.eight-plate.com/, 2008.
Perry, Clayton R. et al.; "Patellar Fixation Protected with a Load-Sharing Cable: A Mechanical and Clinical Study": Journal of Orthopaedic Trauma, 1988, vol. 2, No. 3, pp. 234-240.
Pilliar et al., Bone ingrowth and Stress Shielding with a Porous Surface Coated Fracture Fixation Plate, Journal of Biomedical Materials Research, vol. 13, 799-810 (1979).
Pollo, Fabian E. et al.; "Reduction of Medical Compartment Loads With Valgus Bracing of the Osteoarthritic Knee"; American Journal Sports Medicine, vol. 30, No. 3, 2002; pp. 414-421.
Repicci, John A., M.D. et al. "Minimally invasive unicondylar knee arthroplasty for the treatment of unicompartmental osteoarthritis: an outpatient bypass procedure"; Orthopaedic Clinics of North America, 35 (2004), pp. 201-216.
Sharma, Leena et al.; "The Mechanism of the Effect of Obesity in Knee Osteoarthritis—The Mediating Role of Malalignment"; Arthritis & Rheumatism, vol. 43, No. 3, Mar. 2000, pp. 568-575.
Sharma, Leena, M.D. et al.; "The Role of Knee Alignment in Disease Progression and Functional Decline in Knee Osteoarthritis"; JAMA, Jul. 11, 2001, vol. 286, No. 2, pp. 188-196.
Sommerkamp, G. et al.; "Dynamic external fixation of unstable reatures of the distal part of the radius"; The Journal of Bone and Joint Surgery; 1994, vol. 76-A, No. 8, pp. 1149-1161.
Tencer, Allan F. et al. "Fixation of the Patell (Chap, 9.3)"; in: Biomechanics in Orthopedic Trauma Bone Fracture and Fixation, 1994.
Thakur, A.J.; "Tension Band Wiring"; in; The Elements of Fracture Fixation 1997.
Uchikura, C. et al.; "Comparative study of nonbridging and bridging external fixators for unstable distal radius fractures"; Journal of Orthopaedic Science, 2004, vol. 9, pp. 560-565.
Weisstein, Jason S., M.D. et al.; "Oncologic Approaches to Pediatric Limb Preservation"; Journal of the American Academy of Orthopaedic Surgeons; vol. 13, No. 8, Dec. 2005.
Van Der Esch, M. et al.; "Structural joint changes, malalignment, and laxity in osteoarthritis of the knee"; Scand J. Rheumatol 2005; 34: 298-301.
Wilke, Hans-Joachim et al., "Biomechanical Evaluation of a New Total Posterior-Element Replacement System"; Spine, 2006, vol. 31, No. 24, pp. 2790-2796.

(56) References Cited

OTHER PUBLICATIONS

Yamamoto, Ei et al.; "Effects of Stress Shielding on the Transverse Mechanical Properties of Rabbit Patellar Tendons"; Journal of Biomechanical Engineering, 2000, vol. 122, pp. 608-614.

Andriacchi, Thomas P., Ph.D. et al. "Methods for evaluating the progression of osteoarthritis"; Journal of Rehabilitation Research and Development, vol. 37, No. 2, Mar./Apr. 2000, pp. 163-170.

Arendt, Elizabeth, M.D.; Anatomy and Malalignment of the Patellofemoral Joint—It's Relation to Patellofemoral Arthrosis; Clinical Orthopaedics and Related Research; 2005, No. 436, pp. 71-75.

Benzel, Edward; "Qualititive Attributes of Spinal Implants"; in: Biomechanics of Spine Stabilization, 1995.

Buckwalter, Joseph A,: "Joint distraction for osteoarthritis"; The Lancet, Department of Orthopaedic Surgery, University of Iowa Hospitals and Clinics, vol. 347, Feb. 3, 1996, pp. 279-280.

Coathup, M.J. et al.; "Osseo-mechanical induction of extro-cortiacal plates with references to their surfact properties and goemoetic designs", Elsevier, Biomaterials 20 (1999) 793-800.

Deie, Masataka, M.D. et al.; "A new Articulated Distraction Arthrosplasty Device for Treatment of the Osteoarthritic Knee Joint: A Preliminary Report"; Arthroscopy: The Journal of Arthoscopic and Related Surgery; vol. 23, No. 8 (August), 2007: pp. 833-838.

Dienst, M. et al.; "Dynamic external fixation for distal radius fractures"; Clinical Orthopaedics and Related Research, 1997, vol. 338, pp. 160-171.

Gunther, Klaus-Peter, M.D.; "Surgical approaches for osteoarthritis"; Best Practice and Research Clinical Rheumatology, vol. 15, No. 4, pp. 627-643, 2001.

Hall, J. et al.; "Use of a hinged external fixator for elbow instability after severe distal humeral fracture"; Journal of Orthopaedic Trauma, 2000, vol. 14, No. 6 pp. 442-448.

Krakauer, J. et al.; "Hinged device for fractures involving the proximal interphalangeal joint"; Clinical Orthopaedics and Related Research, 1996, vol. 327, pp. 29-37.

Lafeber et al., Unloading Joints to Treat Osteoarthritis, Including Joint Distraction, Current Opinion in Rheumatology 2006, 18; 519-525.

Leon, Hariberto Ojeda, M.D. et al.; "Minimally Invasive Selective Osetotomy of the Knee: A New Surgical Technique"; Arthroscopy: The Journal of Arthroscopic and Related Surgery, vol., 17, No. 5 (May-June), 2001: pp. 510-516.

Madey, S. et al; Hinged external fixation of the elbow: optimal axis alignment to minimize motion resistance; Journal of Orthopaedic Trauma, 2000, vol. 14, No. 1, pp. 41-47.

Neel, Michael D. M.D. et al.; "Early Multicenter Experience With a Noninvasive Expandable Prosthesis"; Clinical Orthopaedics and Related Research, 2003, No. 415, pp. 72-81.

Neel, Michael D., M.D.; "Repiphysis—Limb Salvage System for the Skeletally Immature"; Wright Medical Techology, Repiphysis Limb Salvage System, 2001, pp. 1-8.

Nockels, Russ P.; "Dynamic Stabilization in the Surgical Management of Painful Lumbar Spinal Disorders"; Spine, 2005, vol. 30, No. 16S, pp. S68-S72.

Orthofix; "Xcaliber Articulated Ankle"; advertising brochure, May 2004.

Supplemental European Search Report for European Patent App. No. 08772484.5 (Jul. 25, 2014).

* cited by examiner

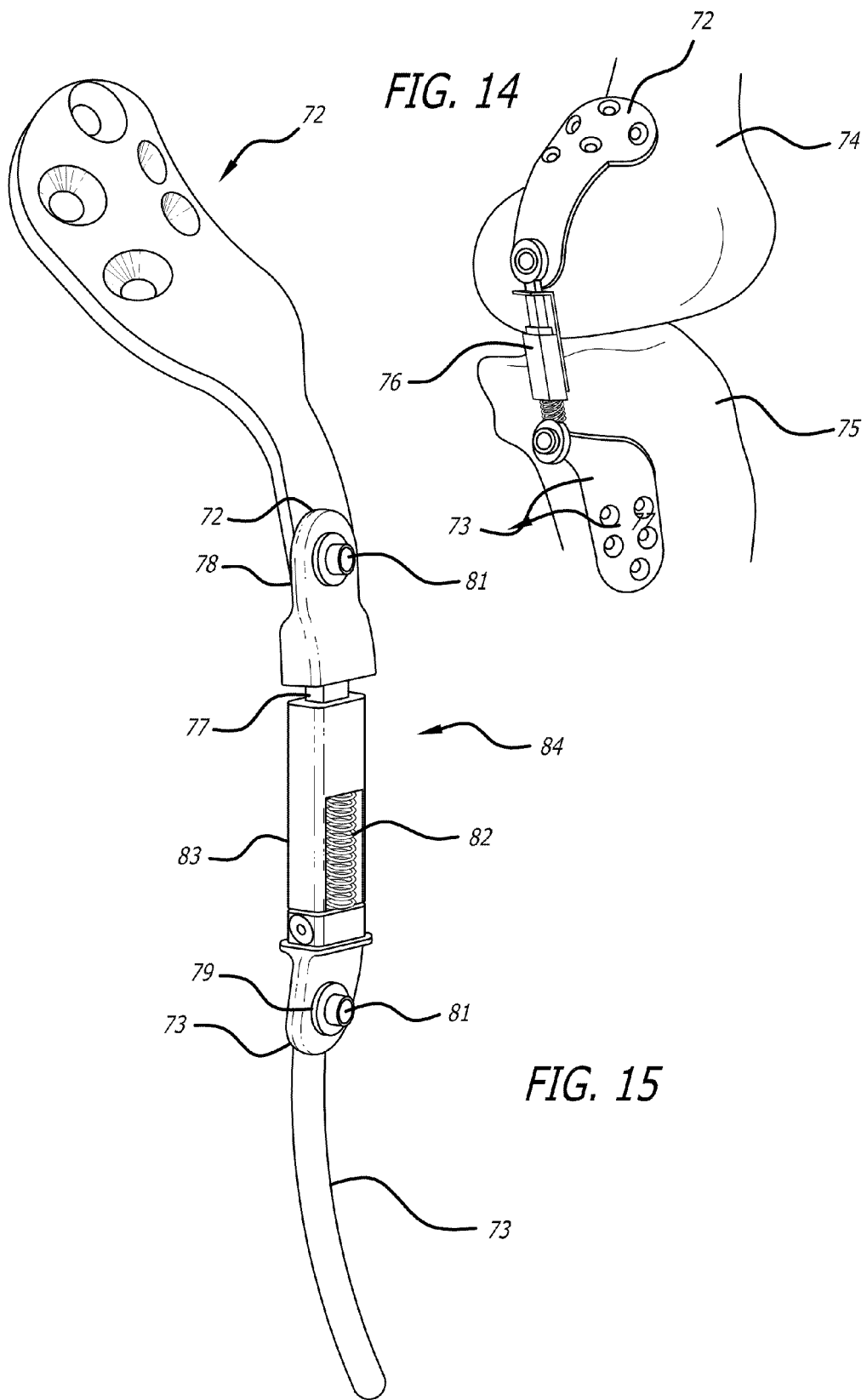

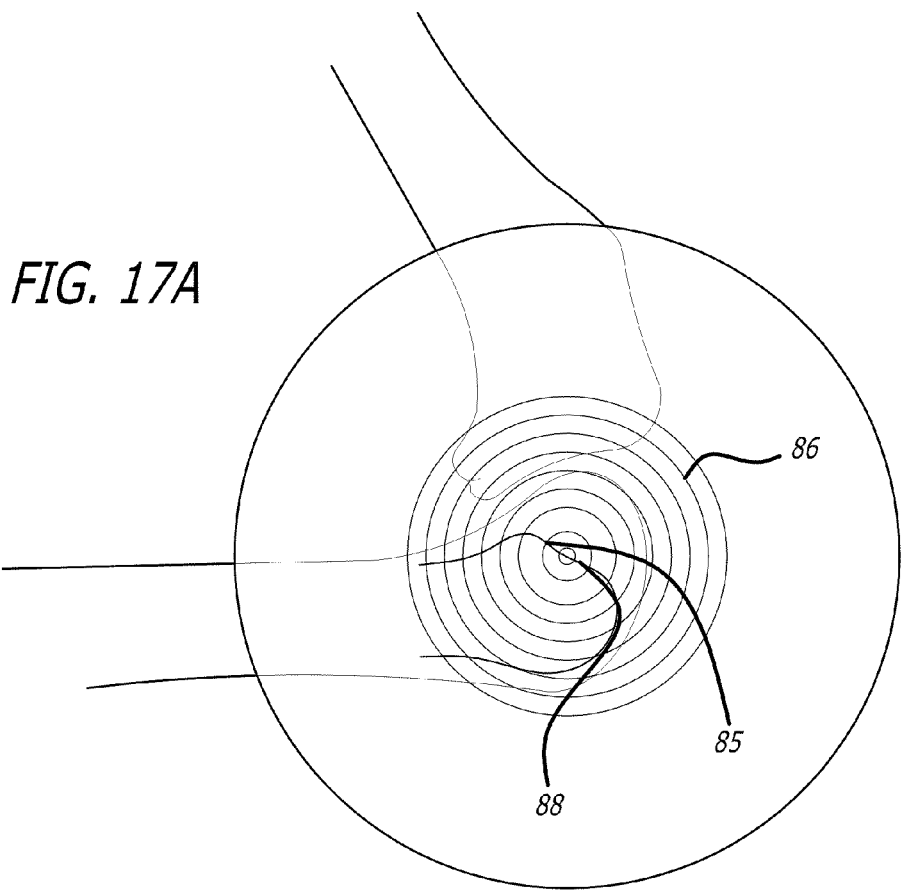
FIG. 17A
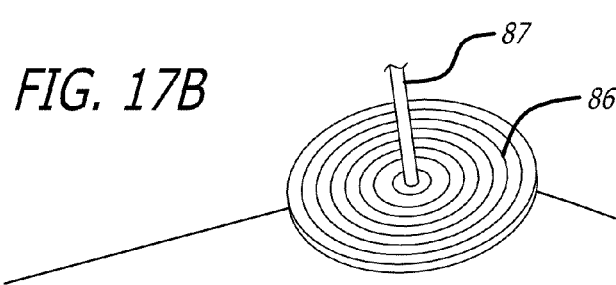
FIG. 17B
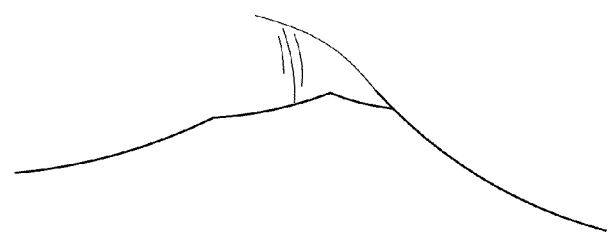

FIG. 19
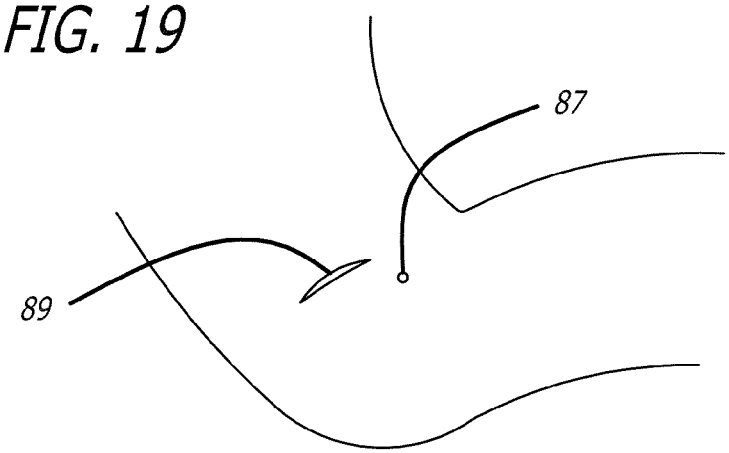
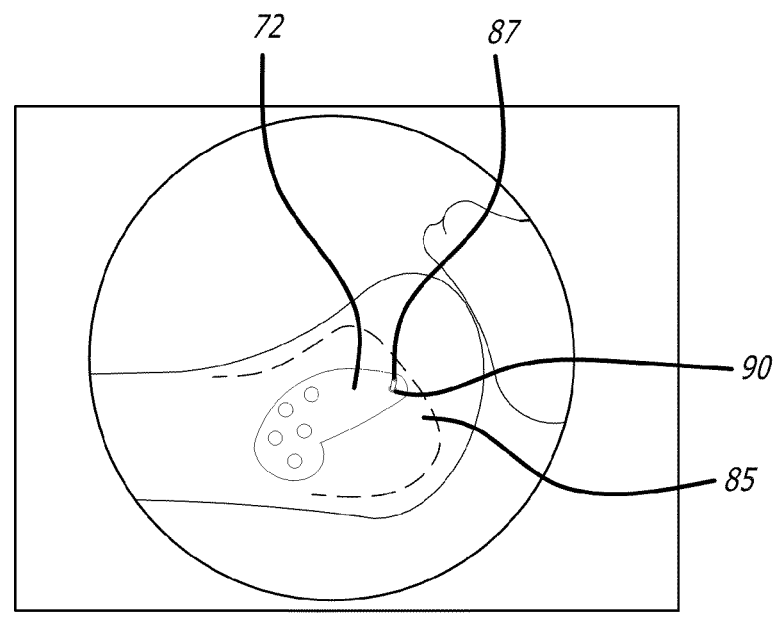
FIG. 20

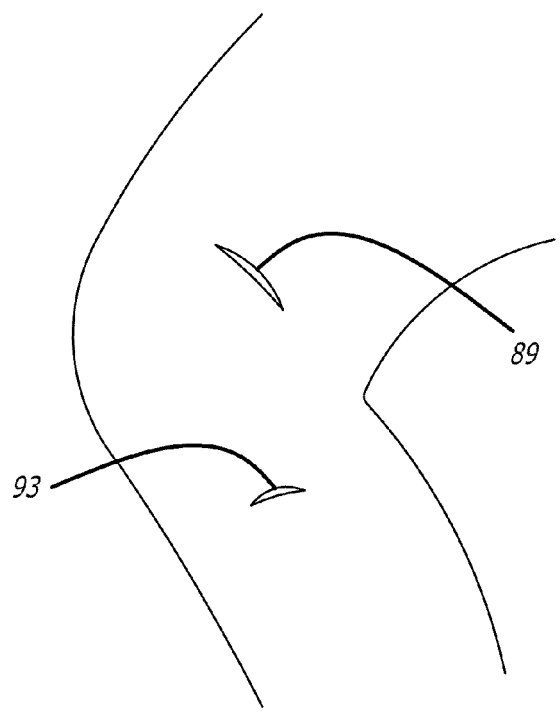
FIG. 23
FIG. 24
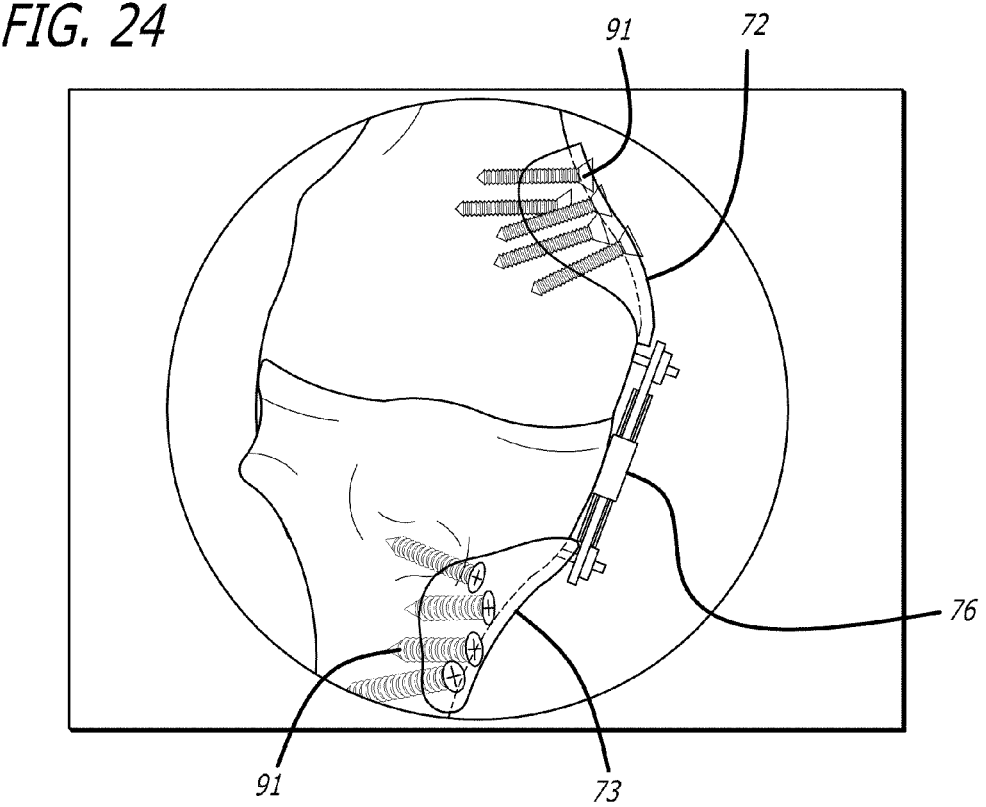

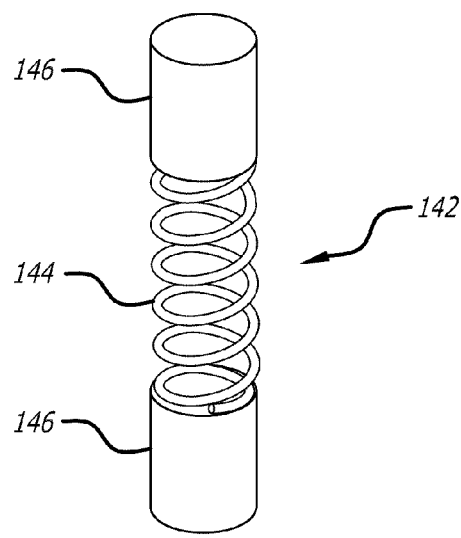
FIG. 39
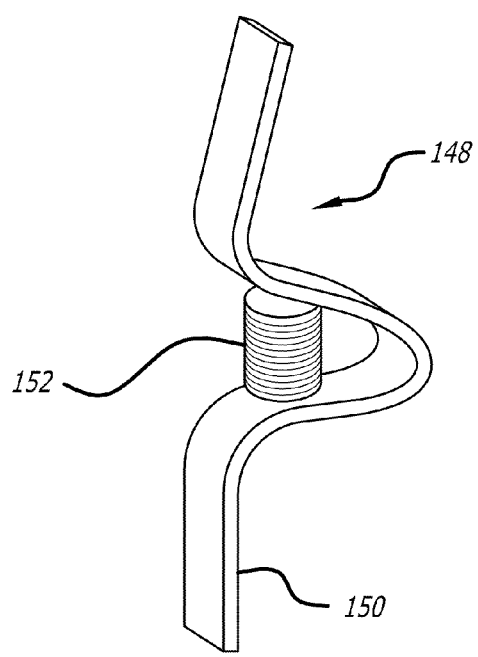
FIG. 40
FIG. 41

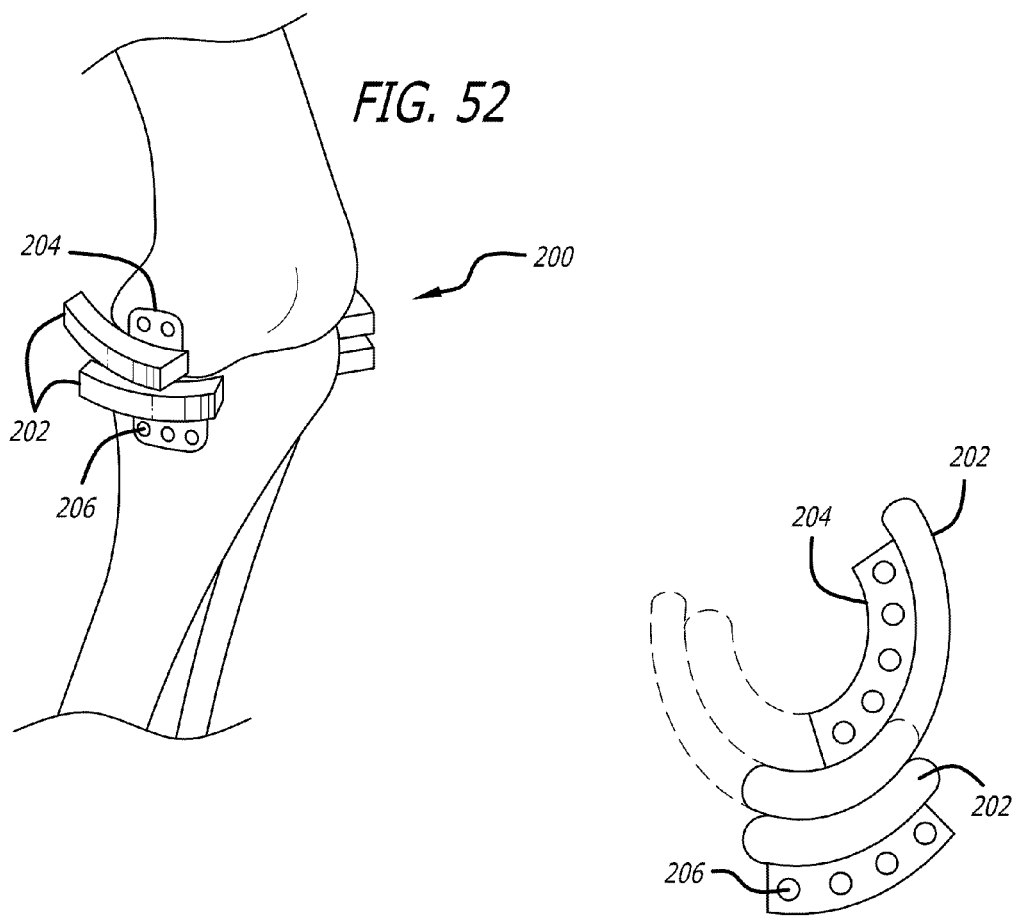
FIG. 52
FIG. 53
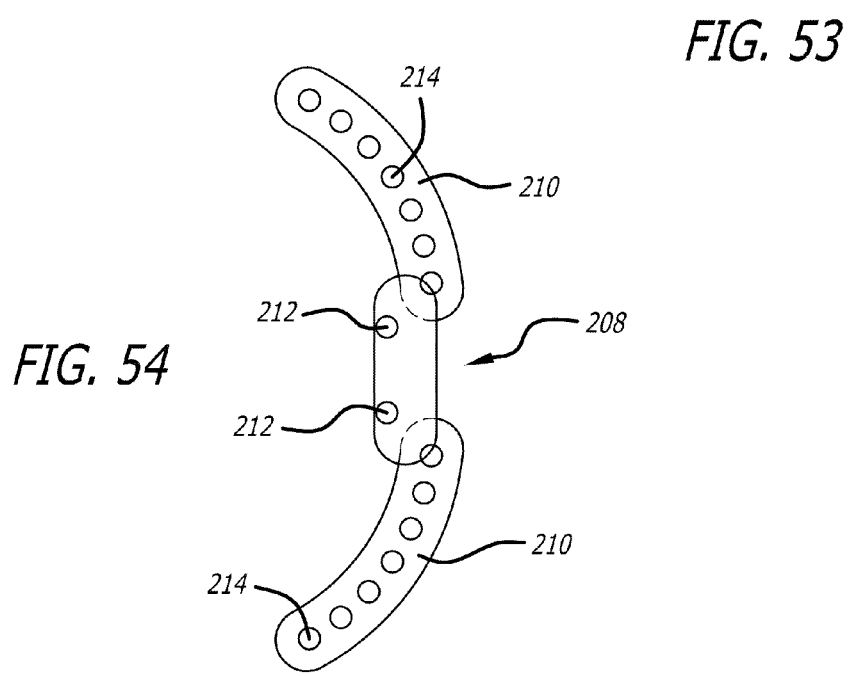
FIG. 54

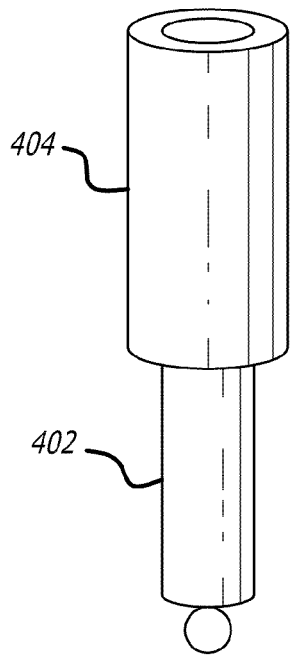 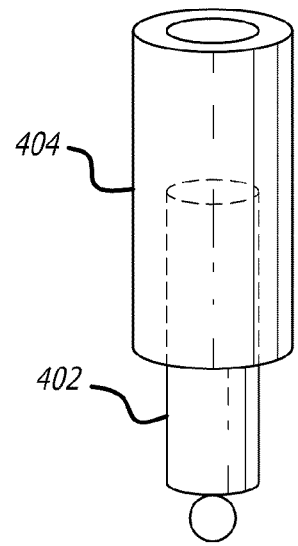
FIG. 90          FIG. 91
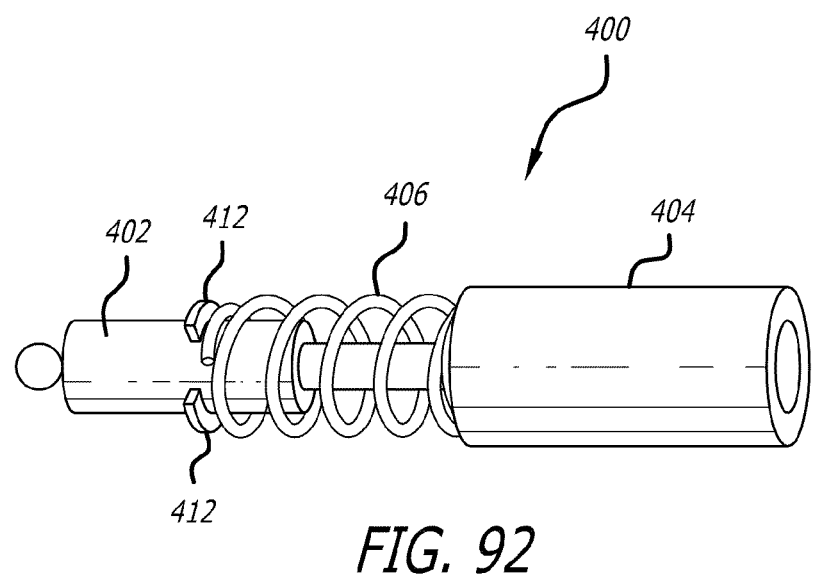
FIG. 92

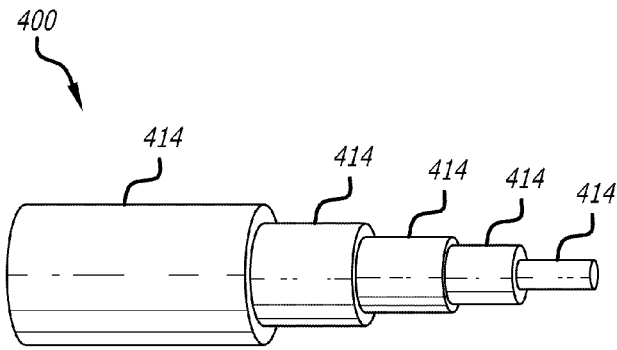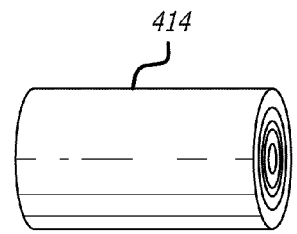
FIG. 93    FIG. 94
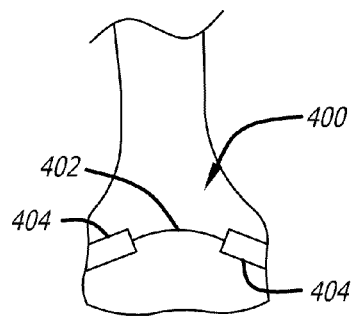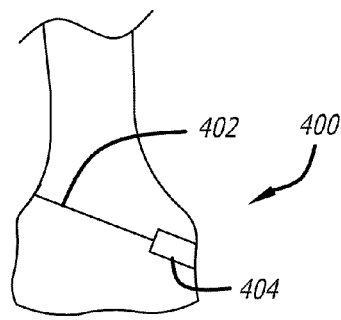
FIG. 95    FIG. 96
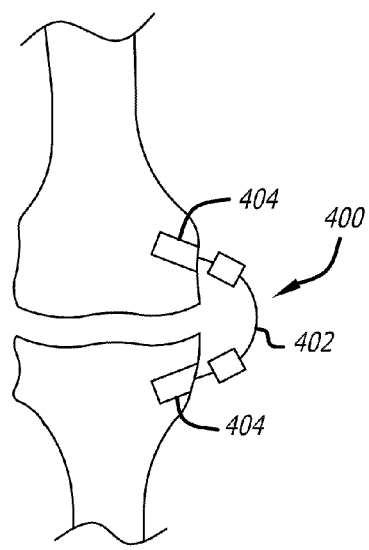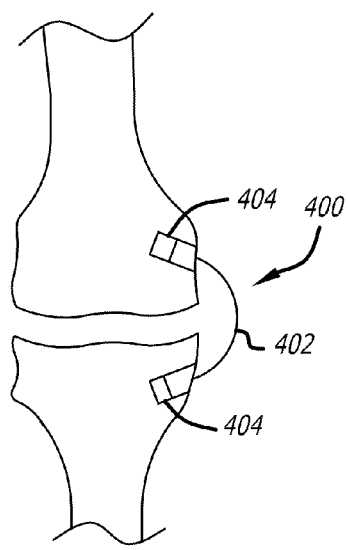
FIG. 97    FIG. 98

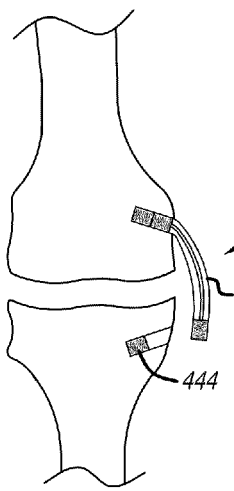 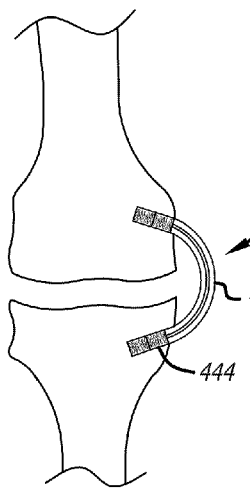 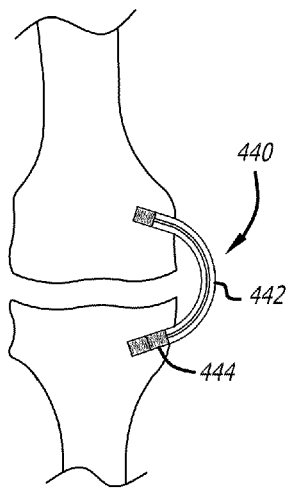
FIG. 104    FIG. 105    FIG. 106
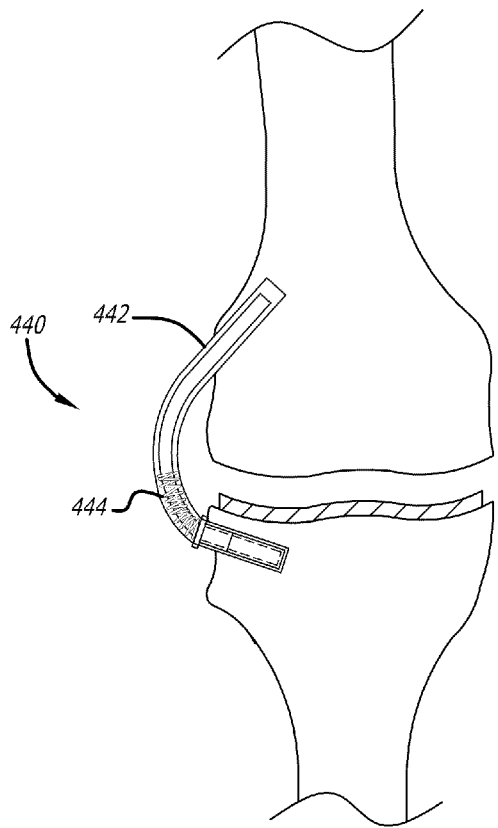
FIG. 107

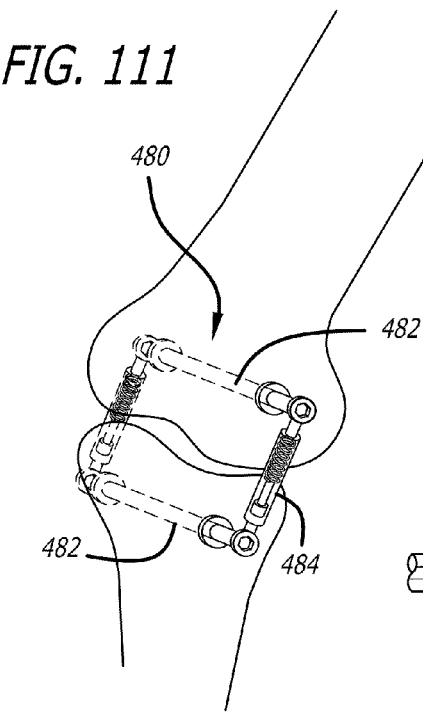
FIG. 111
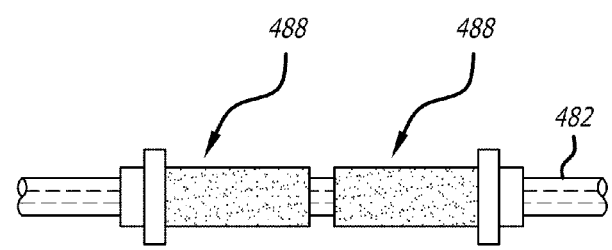
FIG. 112
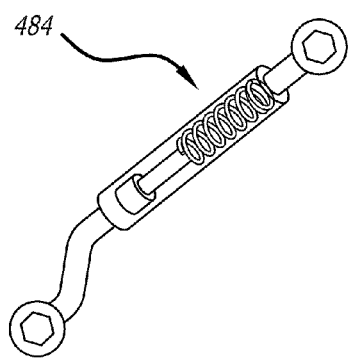
FIG. 113
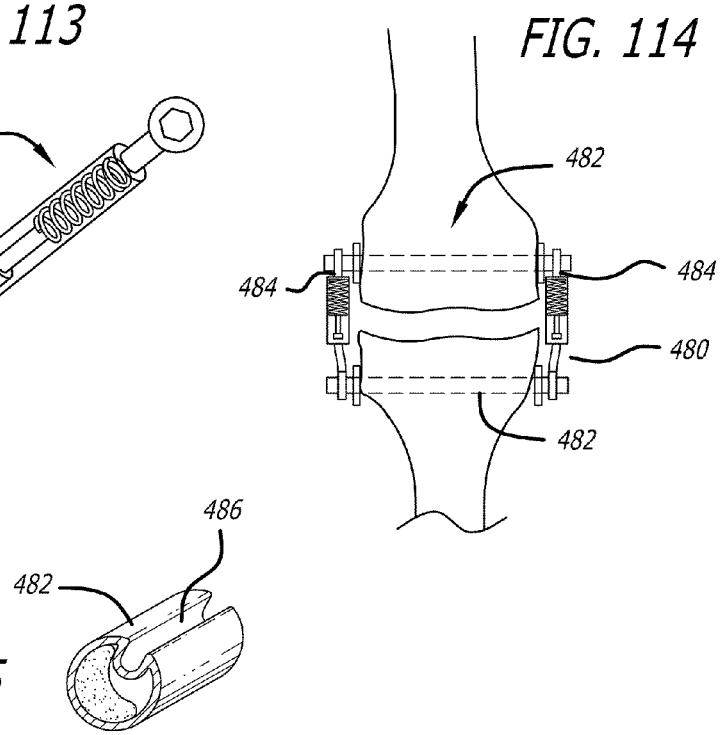
FIG. 114
FIG. 115

EXTRA-ARTICULAR IMPLANTABLE MECHANICAL ENERGY ABSORBING SYSTEMS AND IMPLANTATION METHOD

CROSS-REFERENCES TO RELATED APPLICATIONS

This application is a continuation of U.S. Ser. No. 11/775,139, filed on Jul. 9, 2007, the entire disclosure of which is expressly incorporated herein by reference.

BACKGROUND OF THE INVENTION

The present invention is directed towards systems and methods for treating tissue of a body and more particularly, towards approaches designed to reduce mechanical energy transferred between members forming a natural joint.

Both humans and other mammals belong to the subphylum known as vertebrata. The defining characteristic of a vertebrate is considered the backbone or spinal cord, a brain case, and an internal skeleton. In biology, the skeleton or skeletal system is the biological system providing physical support in living organisms. Skeletal systems are commonly divided into three types—external (an exoskeleton), internal (an endoskeleton), and fluid based (a hydrostatic skeleton).

An internal skeletal system consists of rigid (or semi-rigid) structures, within the body, moved by the muscular system. If the structures are mineralized or ossified, as they are in humans and other mammals, they are referred to as bones. Cartilage is another common component of skeletal systems, supporting and supplementing the skeleton. The human ear and nose are shaped by cartilage. Some organisms have a skeleton consisting entirely of cartilage and without any calcified bones at all, for example sharks. The bones or other rigid structures are connected by ligaments and connected to the muscular system via tendons.

A joint is the location at which two or more bones make contact. They are constructed to allow movement and provide mechanical support, and are classified structurally and functionally. Structural classification is determined by how the bones connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/Immovable bones are connected by dense connective tissue, consisting mainly of collagen. The fibrous joints are further divided into three types:
  sutures which are found between bones of the skull;
  syndesmosis which are found between long bones of the body; and
  gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Synovial joints have a space between the articulating bones for synovial fluid. This classification contains joints that are the most mobile of the three, and includes the knee and shoulder. These are further classified into ball and socket joints, condyloid joints, saddle joints, hinge joints, pivot joints, and gliding joints.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. hinge—such as the elbow; 3. pivot—such as the radius and ulna; 4. condyloidal (or ellipsoidal)—such as the wrist between radius and carps, or knee; 5. saddle—such as the joint between carpal thumbs and metacarpals; and 6. gliding—such as between the carpals.

Synovial joints (or diarthroses, or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Cartilage is a type of dense connective tissue and as shown above, it forms a critical part of the functionality of a body joint. It is composed of collagenous fibers and/or elastin fibers, and cells called chondrocytes, all of which are embedded in a firm gel-like ground substance called the matrix. Articular cartilage is avascular (contains no blood vessels) and nutrients are diffused through the matrix. Cartilage serves several functions, including providing a framework upon which bone deposition can begin and supplying smooth surfaces for the movement of articulating bones. Cartilage is found in many places in the body including the joints, the rib cage, the ear, the nose, the bronchial tubes and between intervertebral discs. There are three main types of cartilage: hyaline, elastic and fibrocartilage.

Chondrocytes are the only cells found in cartilage. They produce and maintain the cartilaginous matrix. Experimental evidence indicates that cells are sensitive to their mechanical (stress-strain) state, and react directly to mechanical stimuli. The biosynthetic response of chondrocytes was found to be sensitive to the frequency and amplitude of loading (Wong et al., 1999 and Kurz et al., 2001). Recent experimental studies further indicate that excessive, repetitive loading may induce cell death, and cause morphological and cellular damage, as seen in degenerative joint disease (Lucchinetti et al., 2002 and Sauerland et al., 2003). Islam et al. (2002) found that continuous cyclic hydrostatic pressure (5 MPa, 1 Hz for 4 hours) induced apoptosis in human chondrocytes derived from osteoarthritic cartilage in vitro. In contrast, cyclic, physiological-like loading was found to trigger a partial recovery of morphological and ultra-structural aspects in osteoarthritic human articular chondrocytes (Nerucci et al., 1999).

Cancellous bone (also known as trabecular, or spongy) is a type of osseous tissue which also forms an important aspect of a body joint. Cancellous bone has a low density and strength but very high surface area, that fills the inner cavity of long bones. The external layer of cancellous bone contains red bone marrow where the production of blood cellular components (known as hematopoiesis) takes place. Cancellous bone is also where most of the arteries and veins of bone organs are found. The second type of osseous tissue is known as cortical bone, forming the hard outer layer of bone organs.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

The main symptoms of osteoarthritis is chronic pain, causing loss of mobility and often stiffness. "Pain" is generally described as a sharp ache, or a burning sensation in the associated muscles and tendons. OA can cause a crackling noise (called "crepitus") when the affected joint is moved or touched, and patients may experience muscle spasm and contractions in the tendons. Occasionally, the joints may also be filled with fluid. Humid weather increases the pain in many patients.

OA commonly affects the hand, feet, spine, and the large weight-bearing joints, such as the hips and knees, although in theory, any joint in the body can be affected. As OA progresses, the affected joints appear larger, are stiff and painful, and usually feel worse, the more they are used and loaded throughout the day, thus distinguishing it from rheumatoid arthritis. With progression in OA, cartilage looses its viscoelastic properties and it's ability to absorb load.

Generally speaking, the process of clinical detectable osteoarthritis is irreversible, and typical treatment consists of medication or other interventions that can reduce the pain of OA and thereby improve the function of the joint. According to an article entitled *Surgical approaches for osteoarthritis* by Klaus-Peter Günther, MD, over recent decades, a variety of surgical procedures have been developed with the aim of decreasing or eliminating pain and improving function in patients with advanced osteoarthritis (OA). The different approaches include preservation or restoration of articular surfaces, total joint replacement with artificial implants, and arthrodeses.

Arthrodeses are described as being reasonable alternatives for treating OA of small hand and foot joints as well as degenerative disorders of the spine, but were deemed to be rarely indicated in large weight-bearing joints such as the knee due to functional impairment of gait, cosmetic problems and further side-effects. Total joint replacement was characterized as an extremely effective treatment for severe joint disease. Moreover, recently developed joint-preserving treatment modalities were identified as having a potential to stimulate the formation of a new articular surface in the future. However, it was concluded that such techniques do not presently predictably restore a durable articular surface to an osteoarthritic joint. Thus, the correction of mechanical abnormalities by osteotomy and joint debridement are still considered as treatment options in many patients. Moreover, patients with limb malalignment, instability and intra-articular causes of mechanical dysfunction can benefit from an osteotomy to provide pain relief. The goal being the transfer of weight-bearing forces from arthritic portions to healthier locations of a joint.

Joint replacement is one of the most common and successful operations in modern orthopaedic surgery. It consists of replacing painful, arthritic, worn or diseased parts of the joint with artificial surfaces shaped in such a way as to allow joint movement. Such procedures are a last resort treatment as they are highly invasive and require substantial periods of recovery. Joint replacement sometimes called total joint replacement indicating that all joint surfaces are replaced. This contrasts with hemiarthroplasty (half arthroplasty) in which only one bone's joint surface is replaced and unincompartmental arthroplasty in which both surfaces of the knee, for example, are replaced but only on the inner or outer sides, not both. Thus, arthroplasty as a general term, is an operative procedure of orthopaedic surgery performed, in which the arthritic or dysfunctional joint surface is replaced with something better or by remodeling or realigning the joint by osteotomy or some other procedure. These procedures are also characterized by relatively long recovery times and their highly invasive procedures. The currently available therapies are not condro-protective. Previously, a popular form of arthroplasty was interpositional arthroplasty with interposition of some other tissue like skin, muscle or tendon to keep inflammatory surfaces apart or excisional arthroplasty in which the joint surface and bone was removed leaving scar tissue to fill in the gap. Other forms of arthroplasty include resection(al) arthroplasty, resurfacing arthroplasty, mold arthroplasty, cup arthroplasty, silicone replacement arthroplasty, etc. Osteotomy to restore or modify joint congruity is also an arthroplasty.

Osteotomy is a related surgical procedure involving cutting of bone to improve alignment. The goal of osteotomy is to relieve pain by equalizing forces across the joint as well as increase the lifespan of the joint. This procedure is often used in younger, more active or heavier patients. High tibial osteotomy (HTO) is associated with a decrease in pain and improved function. However, HTO does not address ligamentous instability—only mechanical alignment. HTO is associated with good early results, but results deteriorate over time.

Other approaches to treating osteoarthritis involve an analysis of loads which exist at a joint. Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. There is also a level of load at which the skeleton will fail catastrophically. Accordingly, it has been concluded that the treatment of osteoarthritis and other conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there has been identified a need for devices which facilitate the control of load on a joint undergoing treatment or therapy, to thereby enable use of the joint within a healthy loading zone.

Certain other approaches to treating osteoarthritis contemplate external devices such as braces or fixators which control the motion of the bones at a joint or apply cross-loads at a joint to shift load from one side of the joint to the other. Various of these approaches have had some success in alleviating pain but suffer from patient compliance or lack an ability to facilitate and support the natural motion and function of the diseased joint. Notably, the motion of bones forming a joint can be as distinctive as a finger print, and thus, each individual has his or her own unique set of problems to address. Therefore, mechanical approaches to treating osteoarthritis have had limited applications.

Prior approaches to treating osteoarthritis have also been remiss in acknowledging all of the basic functions of the various structures of a joint in combination with its unique movement. That is, in addition to addressing loads at a joint and joint movement, there has not been an approach which also acknowledges the dampening and energy absorption functions of the anatomy, and taking a minimally invasive approach in implementing solutions. Prior devices designed to reduce the load transferred by the natural joint typically describe rigid body systems that are incompressible. Mechanical energy is the product of force (F) and displacement distance (s) of a given mass (i.e., $E=Fxs$, for a given mass M). These systems have zero displacement within their working body ($s=0$). Since there is no displacement within the device it is reasonable to say that there is no energy storage or absorption in the device. Such devices act to transfer and not absorb energy from the joint. By contrast the natural joint is not a rigid body but is comprised of elements of different compliance characteristics such as bone, cartilage, synovial fluid, muscles, tendons, ligaments, etc. as described above. These dynamic elements act to both transfer and absorb energy about the joint. For example cartilage compresses under applied force and therefore the resultant force displacement product represents the energy absorbed by cartilage. In addition cartilage has a non linear force displacement behavior and is considered viscoelastic. Such systems not only absorb and store, but additionally act to dissipate energy.

Therefore, what is needed and heretofore lacking in prior attempts to treat joint pain is an implantation method and implant device which addresses both joint movement and varying loads as well as dampening forces and energy absorption provided by an articulate joint.

The present invention satisfies these and other needs.

SUMMARY OF THE INVENTION

Briefly and in general terms, the present invention is directed towards treating diseased or mal-aligned body components. In one aspect, the present invention is embodied in methods and devices for treating and preserving body joints.

In one approach to a method of device implantation, a pre-operative session is performed to assess the need at a joint and to map the articulation of the members forming the joint. Attachment sites are also assessed pre-operatively. During surgical intervention, a first rotation point location is identified along a first member of a joint. Next, access is gained to an area proximate the first pivot link location and a first base component is fixed upon the first member in a manner maintaining use of the first rotation point location. A second rotation point location is then identified along a second member of a joint and surgical access is obtained proximate the second rotation point location. Subsequently, a second base component is fixed along the second member while maintaining use of the second rotation point location. A subcutaneous channel is provided between the first and second rotation point locations and an energy manipulator is inserted within the channel. The energy manipulator is thereafter mounted to the bases. A tissue barrier is placed about the energy manipulator to protect joint anatomy.

In a contemplated method, the energy manipulation assembly of the present invention can be initially configured to off-load or manipulate loads to a desired degree, and to be later altered as patient needs are better determined or change. Accordingly, post-operative alterations are contemplated. In this regard, it is also contemplated there be no initial off-loading or load manipulation until the interventional site heals and the device is firmly implanted. Moreover, as needs change, the method can involve removal or replacement of one or more components of the energy manipulation assembly. Further, various degrees of non-invasive approaches can be employed as is practical for a given interventional procedure.

In one aspect of treating and preserving body joints, the present invention is embodied in methods and devices implanted under the patient's skin for relieving joint pain that do not require modification of articular cartilage. In a preferred aspect, the device is implanted under the patient's skin but outside of the joint capsule. In a particular aspect, the joint pain is caused by osteoarthritis.

In one embodiment, the present invention addresses the pain associated with joint disease and mal-alignment. In presently contemplated embodiments, a minimally invasive approach is taken to alleviate pain while preserving full motion of the bones forming a joint. The devices of the present invention accomplish one or more of: absorbing energy during normal gait, reducing load on at least a portion of the natural joint, load transferring or bypassing, energy cushioning, and load sharing or redistribution. In addition, both energy dampening and shock absorption are considered in effecting such load manipulations. Further, the particular anatomy of a patient is considered in the contemplated approaches in that loads on desired portions of anatomy are manipulated without overloading healthy surfaces. It is believed that employing the approaches of the present invention can slow the progression of disease affecting the joint and can further improve alignment, stability, or support or enhance medial collateral ligament (MCL) or lateral collateral ligament (LCL) function.

In a preferred embodiment, the present invention adds an energy absorber to the joint to reduce energy transferred through the natural joint.

The present invention can be used unilaterally, bilaterally or multi-laterally around a body joint.

The present invention has the capacity to absorb energy in addition to transfer energy from the joint. The simplest embodiment of the present invention incorporates a linear elastic spring. The energy absorption of the spring can be expressed as the product of force and displacement. In addition to a linear spring element, non linear spring members can be employed to alter the energy absorption behavior under the same loading or displacement conditions. Although actual springs are used to show various embodiments of the present invention, these elements could also be substituted with a material or other device with spring-like characteristics (e.g., an elastomeric member). Such elastomers include thermoplastic polyurethanes such as Tecoflex, Tecothane, Tecoplast, Carbothene, Chronthane and Chrono-Flex (grades AR, C, AL). Moreover, materials such as Pebax, C-flex, Pellathane and silicone and silicone foam can also be employed.

In other embodiments, spring systems may be coupled with dampening devices such as dash pots. In these embodiments, the spring element is a storage or absorber device while the dashpot acts to dissipate the energy from the spring. Such embodiments alter the velocity of displacement of the spring, thereby altering the energy absorption behavior. Although more traditional dampening devices are used to show various embodiments of the present invention, these elements could also be substituted with a material or other device with dampening characteristics (e.g., a small pore sponge).

The operations of these embodiments and the prior art rigid systems can be described graphically using force versus displacement diagrams (mass is assumed constant). Thus a rigid body system that allows no displacement, no energy absorbed by the device, can be compared with a simple linear spring system of the present invention where energy is absorbed in proportion to a spring constant (i.e., stiffness of the spring) as well to spring and dampener combination systems where the energy absorbed is a function of the spring constant and the dampener.

One particular beneficial aspect of the energy absorption systems of the present invention are that they are capable of absorbing a constant amount of energy from the joint independent of joint kinematics or loading conditions. In contrast, the rigid body systems of the prior art (such as a cam system) are based on the physician separating (i.e., distracting) the natural joint a given distance in the unloaded state and attaching the rigid body system. The rigid body system then maintains this distance/distraction throughout the gait cycle and through bending of the joint. To maintain this distraction, the rigid body must transfer a wide range of forces directly depending on joint kinematics.

Another particularly beneficial aspect of the energy absorption system of the present invention is that the absorption system may be designed to absorb, dissipate and/or transfer energy at different rates or positions in the gait cycle thereby enabling customization of the system to the specific need. Considering the knee joint by way of example, if a spring system is coupled to a dampener to create a viscoelastic body, the system may be designed to absorb severe sudden impact loads (such as jumping) and dissipate these loads after the impact event. This mode of operation is akin to the natural role of cartilage. Conversely, the system can be designed to behave primarily as an energy transfer unit during high rates of knee motion (e.g. sprinting/running) but act as an energy absorber during normal rates of motion (e.g. walking).

Yet another particularly beneficial aspect of the energy absorption system of the present invention is that the absorption system may also be tuned to occur at particular points in the gait or flexion cycle depending on the disease state. For example an individual with concentrated loading at heel strike may only require absorption at this phase of knee motion so the system may be adjusted to act only during this region of the gait cycle. Alternatively an individual may have focal loss of cartilage on the posterior aspect of the femoral condyle and so stair climbing or kneeling becomes painful or problematic. In this scenario the system would be adjusted to absorb energy in the kinematic positions necessary and thereby maintaining the normal knee energy transfer outside of supporting the diseased locations.

In another beneficial aspect of the present invention, components of the system are designed for easy removal and, if necessary, replacement while others are intended for permanent fixation. The permanent components are fixation base components which can have bony ingrowth promoting surfaces and are responsible for fixation of the system to the skeletal structure. The removable components include the mobile elements of the system such as the energy manipulation members and/or the pivots or ball joints.

Various joints of the body can be treated employing the systems and methods of the present invention. In particular, articulating bones involved in synovial joints can benefit from the present invention. Accordingly, there are contemplated applications to the joints in the knee, ankle, shoulder, hip, hand and wrist. Further, the present invention can have applications in treating cartilaginous joints such as those found in the spine.

In a further aspect, the present invention seeks to accomplish 1 to 40% energy or load reduction while maintaining full motion of the body parts. A 5 to 20% energy or load reduction has been postulated to be desirable in certain circumstances to accomplish the alleviation of pain without approaching undesirable load shielding. The devices of the present invention further provide greater energy manipulation during junctures of highest loads placed between body parts as well as less energy manipulation when loads between members decrease. In this way, the present invention complements the action of body parts such as those found at joints.

In some joints, it is desirable that 100% of the energy be absorbed by the device(s), such joints may be those in the hands or upper extremity. In such cases, it may be desirable to have the devices placed bilaterally on either side of the joint. In the lower extremity, in severe cases, 100% energy absorption is achievable, however this may expose the device to more wear and shorter life. Some patients may accept this if the device is able to bridge the patient through a difficult period and it is easily replaced or removed without impacting the patients ability to receive a total joint replacement later.

In another embodiment of the present invention, an energy absorption device is implanted at a diseased joint to restore cyclic, physiological-like loading thereby protecting chondrocytes from load induced apoptosis.

In yet another embodiment of the present invention, an energy absorption device is implanted at a diseased joint to facilitate at least a partial recovery of morphological and ultra-structural aspects in osteoarthritic articular chondrocytes.

In another embodiment of the present invention, an energy absorption device is implanted adjunctively with a cartilage repair procedure such as mosaicplasty, osteochondral allograft transfer, autologous chondrocyte implantation or microfracture. Such an adjunctive procedure would enable less strict rehabilitation regimes while simultaneously protecting the graft and stimulating it with appropriate motion.

In another embodiment of the present invention, an energy absorption device is implanted in conjunction with a uni-compartmental joint replacement prosthesis or total joint replacement prosthesis. Such combination procedure will reduce wear rates by reducing the loads and contact forces between surfaces of the joint prosthesis.

Rotation point location of the energy manipulation member on the femur is determined in part by the mechanism of the device. The inventors of the present invention have discovered regions on the femoral chondyl in which a rotation point on the device relative to a tibial rotation point along a line normal to the ground from the femoral rotation point will either have minimal displacement, lengthening of the device or shortening of the device as the joint moves from full extension to flexion. Therefore, if the desired device is to function by elongation its rotation point will be located in the appropriate region. Conversely, if the desired device is to function by compression its rotation point will be located in a different appropriate region.

In one specific embodiment, the present invention is embodied in a device utilizing an element, or elements functioning as a unit, which responds to bending or changes in elongation. In an application to a knee joint, this device forms a bending spring that is to span the tibiofemoral joint and be anchored into the tibia and femur. Further, the device is used to take on some of the loading experienced by the articular surfaces of the tibiofemoral joint, thus unloading the joint. In one embodiment, the device is designed to off load the joint during knee extension. Unloading in this phase is governed by the compression of the device—increased compression yields increased joint un-loading. The device is anchored in a position which ensures device elongation resulting from knee flexion. As the knee moves into flexion, the device is un-compressed and will cause little to no joint off-loading. The device may have other features which ensure correct device alignment, and prevent against buckling, as the device transitions into a compressed state. The device can also be configured to provide off-loading during flexion.

In another specific approach, the present invention is embodied in a cam engagement assembly utilizing contacting elements, at least one of which having an eccentric contacting surface. The element, or elements, possessing the eccentric surface define a cam. Again in an application to the knee joint, one element is anchored to the femur and the other to the tibia. Implanted, the device will span the tibiofemoral joint. The degree, duration, and instance of elemental contact is dictated by the profile of the cam element or elements. In one embodiment, the cam is designed to cause increased contact stress between the device elements which span the joint when the knee is in extension. During instances of increased contact stress, the normal energy experienced by the articular surfaces of the tibiofemoral joint will be absorbed and taken on, in part, by the device. During instances of knee flexion, the cam profile will ensure little or no engagement leading to joint off-loading. Thus, the amount of energy absorption will be controlled by a spring element which backs the cam element. The spring element can be adjusted, or exchanged, to tune the amount of energy absorption across the joint.

In yet another specific approach, a segmented support assembly is employed to address joint needs. This concept utilizes multiple elements that align to provide columnar support at desired phases of knee movement. In one application, the device is designed to provide columnar support during phases of knee extension. That is, each element is constrained by the adjacent element in a variable fashion—least constrained during states of elongation and most constrained during states of compression. The variable motion constraint, or tolerance which increases with elongation, is designed so that the cumulative effect is to accommodate the complex motion of the tibiofemoral joint for example as it transitions from extension into flexion. The device is anchored, via mounting components, in a way that dictates device elongation during knee flexion and device compression during knee extension. During the state of device compression, the device will experience part of the energy normally taken on by the articular surfaces of the tibiofemoral joint—thus reducing the energy absorbed by the joint by a desired amount. The amount of energy absorption can be adjusted, via the mounting components, to a desired and measurable amount. The assembly will accommodate the transition from an unloaded to a loaded state by the use of elements, possessing either spring or dampening characteristics, either in the device mounting components or in between the mating surfaces of the device elements.

In a further approach, the invention is embodied in a piston support assembly. This approach employs a spring loaded piston mechanism to absorb energy normally experienced by the anatomical joint. The piston is comprised of an axially mobile member or rod moving in a defined path. Depending on the axial position of the rod, a compressible spring is engaged thereby transferring load through the mechanism. When the spring is not engaged no absorbing or load transfer occurs. The device may utilize rigid and coaxial elements that ride into or through each other. Load transfer and energy absorption occurs when the spring is engaged. For this system to function without hindering the range of motion of the knee for example, the fixation or attachment points between bone and piston mechanism are free to revolve about an axis (possibly multiple axes). In addition, the piston is capable of rotating about its longitudinal axis to facilitate rotational along the axis of the anatomical joint.

The present invention also includes a staged procedure. In this aspect, the energy absorption system is comprised of permanent fixation base components and removable energy absorption. The permanent fixation base components incorporate a bone ingrowth promoter on their bone contacting surface (e.g. porous surface, calcium phosphate coating, textured surface etc.). It is important to stimulate this interface using moderate loads to ensure the creation of a bony interface, however overloading the interface prematurely may prevent bone ingrowth. To facilitate bony ingrowth, it is possible that the system will be implanted in a mode of operation whereby it is absorbing small amounts of load to create a moderate load condition at the interface. A subsequent simple procedure will be completed at an appropriate time post implantation to adjust the energy absorption settings to absorb higher amounts of load.

In one particular aspect, three dimensional (3D) navigation is employed to accomplish placement of a peri-articular joint. The joint in question is scanned with natural or added landmarks thereat using CT, MRI or other remote imaging techniques. This data is imputted into a 3D navigational software and tracker system. Tracker technology could employ RF, optical or electromagnetic imaging. Further, the tracker can be self-powered or it may be passive. In combination with a reference tool, the tracker then facilitates accurate placement of an energy manipulating system across the target joint.

The present invention also contemplates intra-articular drug delivery in combination with joint energy and load manipulation. In one contemplated approach, a drug release device is loaded with a drug and a sustained released drug carrier, and placed at a target area within or near a diseased or malaligned joint, such as on or in the device of the present invention. Various drugs and mechanisms for sustained release are also contemplated.

Moreover, in certain aspects, the present invention also contemplates employing sensors to provide information on performance. For example, pressure sensors can be placed within or adjacent the device or anatomy to indicate aspects of function and loads. Sensors in the implant may allow for non-invasive telemetry and capture of information regarding joint motion. Telemetry may be usable to control various settings in the device.

The present invention also contemplates that the components are compatible with joint diagnostic techniques such as magnetic resonance imaging and computed tomography.

Additionally, the present invention contemplates post-operative percutaneous adjustability and tuning of the implant's characteristics in response to patient feedback. It may be desirable to detect the internal tension and/or dampening setting of the device while it is being accessed percutaneously or alternatively have those features easily detectable using x-ray or another non-invasive modality such as ultrasound.

In one contemplated approach, a core shaft of the energy manipulation assembly can be ribbed like a ratchet about which is configured a moveable piston mounted on a collar equipped with a pair of spaced buttons. Depression of the buttons cause complementary structure on inside of the collar to become disengaged from the ribs of the core shaft so that adjustments can be made. The assembly can be further configured so that the adjustment can be made only when the joint is in flexion and only when both buttons are deliberately pressed.

Another aspect of some embodiments of the present invention is to enclose at least a part of the energy manipulating device in a sheath. The sheath allows the tendons and soft tissue to avoid being abraded by the presence of the implant in that region during movement. By allowing the tissue to form a capsule around the sheath of the implant, the tissue will be strengthened and the likelihood of erosion will be reduced. The sheath also allows for easy replaceability, in some embodiments of the link components because they can be inserted into the sheath once the original components are removed without causing any additional tissue disruption.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 14 is a perspective view, depicting the base components of FIG. 13 with an energy manipulation assembly attached therebetween;

FIG. 15 is a perspective view partially in cross-section, depicting one preferred embodiment of an energy manipulation;

FIG. 17A is an elevation view; depicting a first step in an implantation procedure;

FIG. 17B is a perspective view, depicting a second step in an implantation procedure;

FIG. 19 is a perspective view, depicting a third step in an implantation procedure;

FIG. 20 is an elevation view, depicting positioning of a proximal base component in an implantation site;

FIG. 23 is a perspective view, depicting the formation of a second access hole of the implantation procedure;

FIG. 24 is an elevation view, depicting a completely implanted energy manipulation device;

FIG. 39 is a perspective view, depicting a yet further bending spring assembly with a central spring;

FIG. 40 is a perspective view, depicting a bending spring assembly including a stop member;

FIG. 41 is a perspective view, depicting the bending spring assembly of FIG. 40 in its compressed configuration;

FIG. 52 is a perspective view, depicting a energy manipulation assembly incorporating cam engagement structure;

FIG. 53 is a side view, depicting the load bearing assembly shown in FIG. 52;

FIG. 54 is a perspective view, depicting yet another embodiment of a energy manipulation assembly;

FIG. 90 is a perspective view, depicting still yet another embodiment of a piston support subassembly;

FIG. 91 is a perspective view, depicting the assembly of FIG. 90 in a compressed configuration;

FIG. 92 is a perspective view, depicting a further embodiment of a energy manipulation assembly incorporating piston support structure;

FIG. 93 is a perspective view, depicting a telescoping arrangement of a piston support subassembly;

FIG. 94 is a perspective view, depicting the assembly of FIG. 69 in a compressed configuration;

FIG. 95 is a cross-sectional view, depicting a energy manipulation assembly substantially completely imbedded within body tissue;

FIG. 96 is a cross-sectional view, depicting another approach to a energy manipulation assembly substantially completely imbedded within body tissue;

FIG. 97 is a cross-sectional view, depicting a first step in the implantation of a energy manipulation assembly incorporating piston support;

FIG. 98 is a cross-sectional view, depicting a second step in the implantation of the assembly shown in FIG. 97;

FIG. 104 is a cross-sectional view, depicting a first step in the implantation of a sheathed energy manipulation assembly;

FIG. 105 is a cross-sectional view, depicting a second step in an implantation approach of the assembly depicted in FIG. 80;

FIG. 106 is a cross-sectional view, depicting the assembly of FIG. 105 fully implanted;

FIG. 107 is a cross-sectional view, depicting an enlarged view of an implanted energy manipulation assembly including piston support;

FIG. 111 is a perspective view, depicting a energy manipulation assembly including lateral substructure spanning a width of treated body tissue;

FIG. 112 is an enlarged view, depicting substructure of the device depicted in FIG. 111;

FIG. 113 is an enlarged view, depicting substructure of the device depicted in FIG. 111;

FIG. 114 is a cross-sectional front view, depicting the assembly of FIG. 111;

FIG. 115 is a cross-sectional view, depicting yet another component of the assembly depicting in FIG. 111;

FIG. 116 is a perspective view, depicting a further embodiment of a energy manipulation assembly incorporating piston support;

FIG. 117 is a cross-sectional view, depicting substructure of the assembly depicted in FIG. 116;

FIG. 118 is a cross-sectional view, depicting other substructure of the assembly depicted in FIG. 116;

FIG. 119 is a back view, depicting yet another approach for an energy manipulation assembly;

FIG. 120 is a perspective view, depicting the approach shown in FIG. 119;

FIG. 121 is a side view, depicting a further embodiment of an energy manipulation assembly of the present invention;

FIG. 122 is a perspective view, depicting a bilateral approach of the present invention;

FIG. 123 is a perspective view, depicting another bilateral approach of the present invention;

FIG. 124 is a perspective view, depicting an embodiment of the present invention where the body anatomy is aligned;

FIG. 125 is a perspective view, depicting the embodiment of FIG. 124 with the body anatomy in an articulated configuration;

FIG. 126 is a perspective view, depicting an embodiment of the present invention incorporating pivoting and disengaging structure;

FIG. 127 is a perspective view, depicting the embodiment of FIG. 126 with the anatomy in an articulated position;

Figure 128:
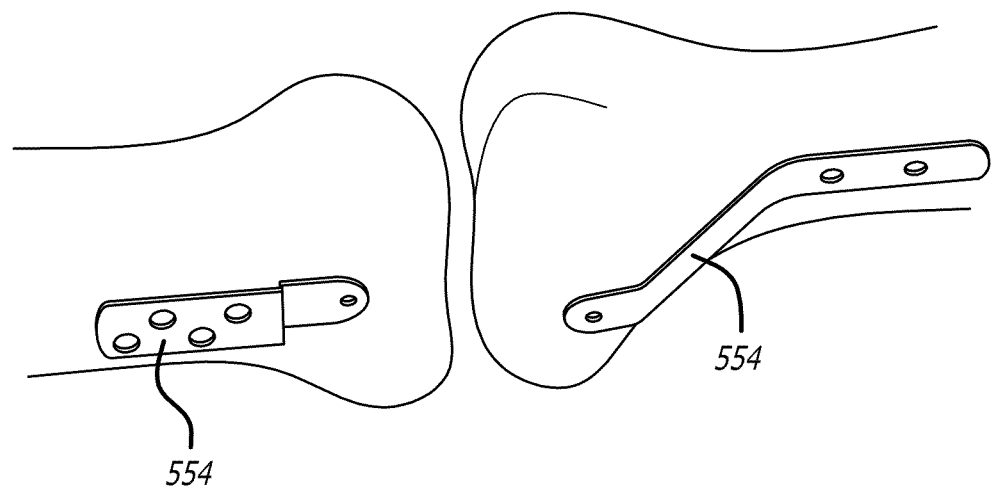
Figure 129:
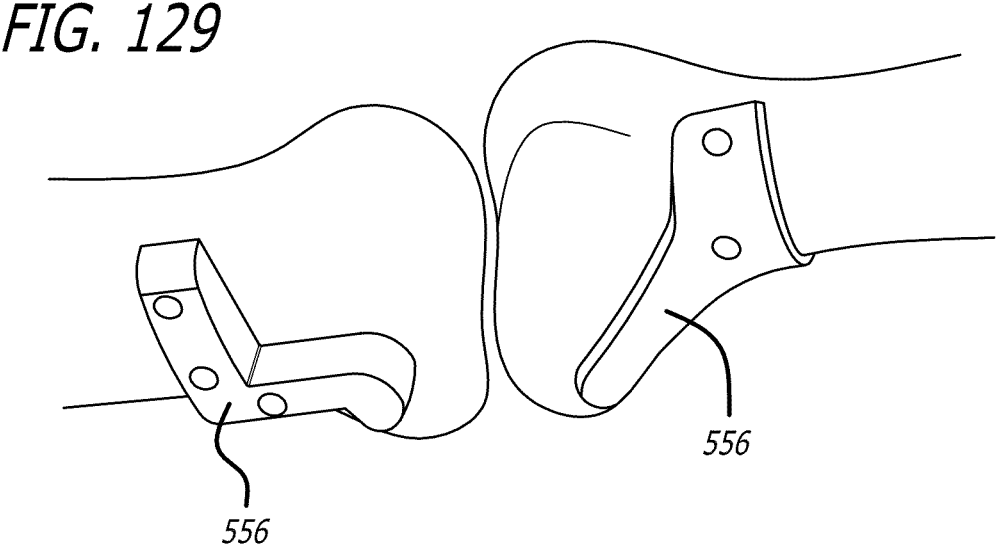
Figure 130:
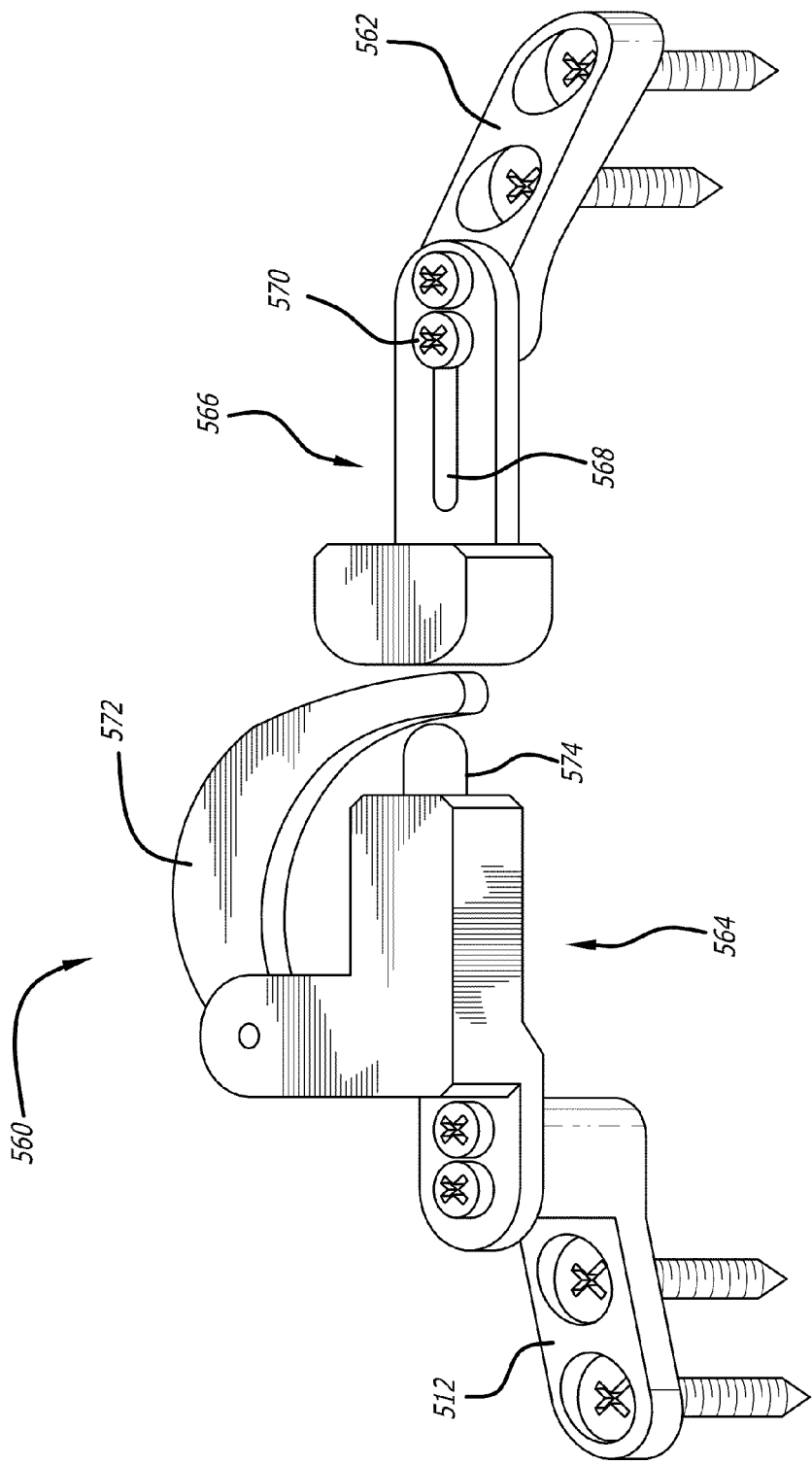
Figure 131:
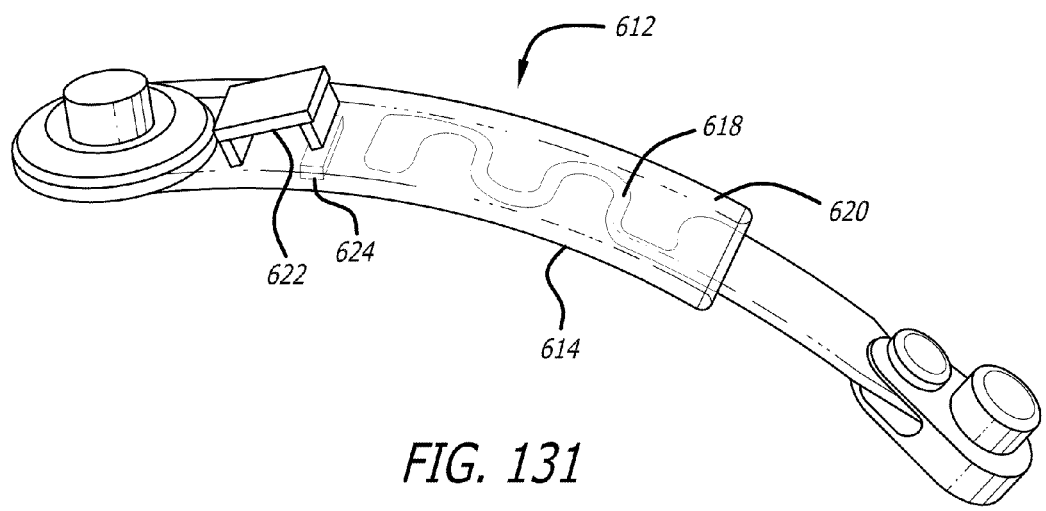

FIG. 128 is a perspective view, depicting yet another embodiment of mounting structures attached to body anatomy;

FIG. 129 is a perspective view, depicting still yet another embodiment of mounting structure attached to body anatomy;

FIG. 130 is a perspective view, depicting yet another approach to an energy manipulation assembly;

FIG. 131 is an isometric view, depicting another energy manipulation assembly of the present invention.

Figure 132:
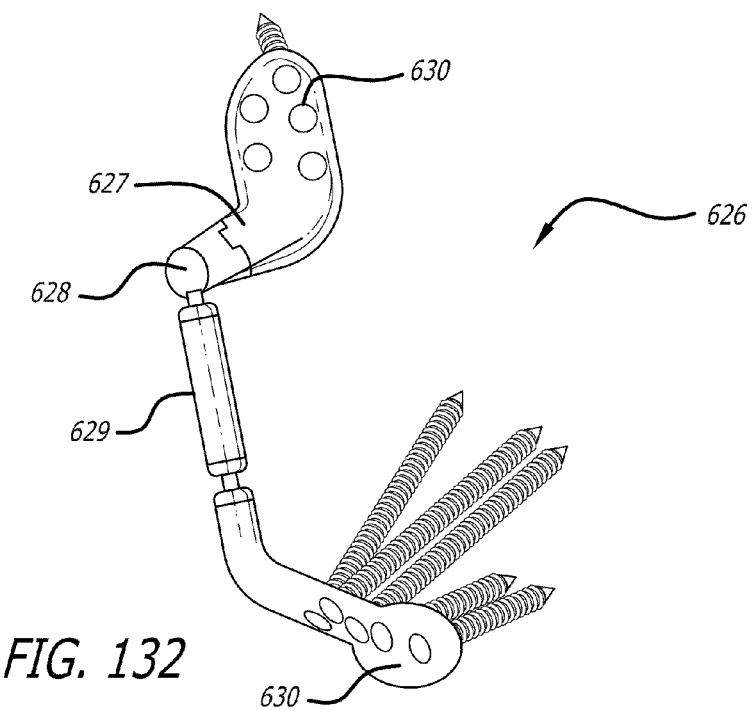
Figure 133:
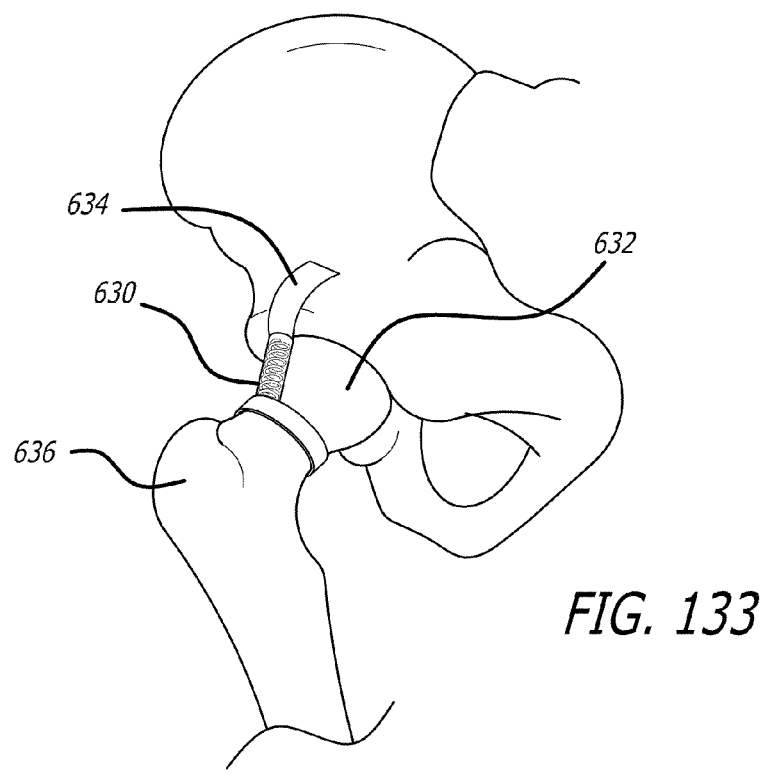
Figure 134:
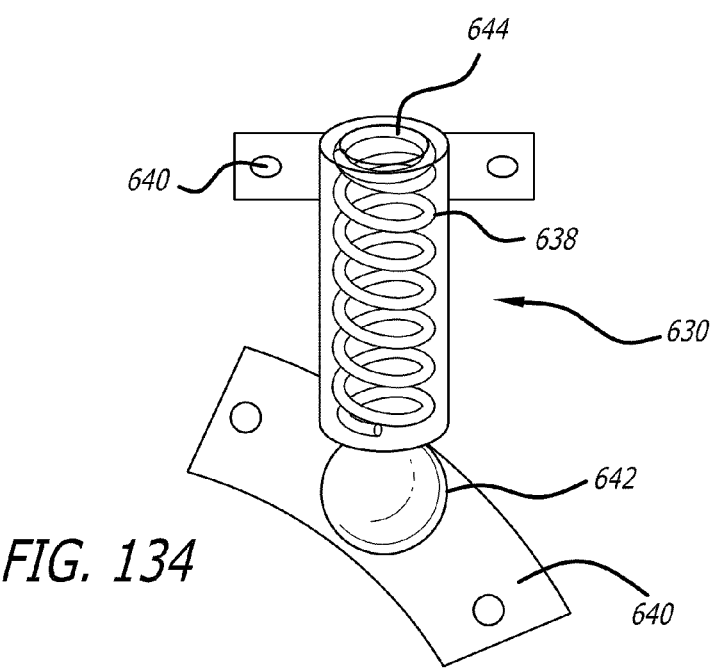
Figure 135:
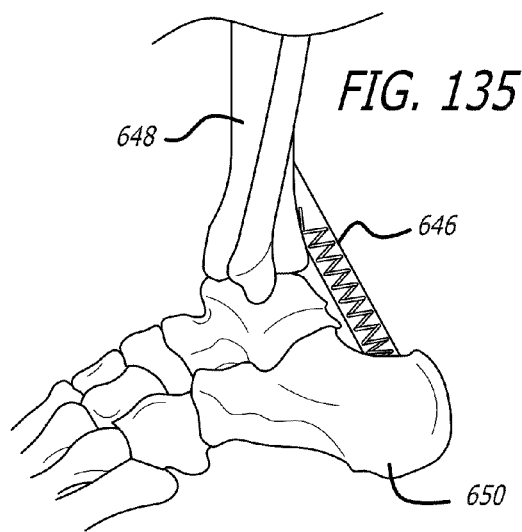
Figure 136:
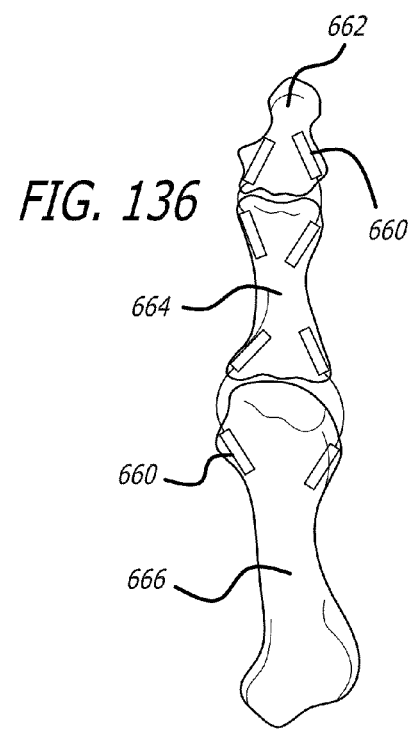
Figure 137:
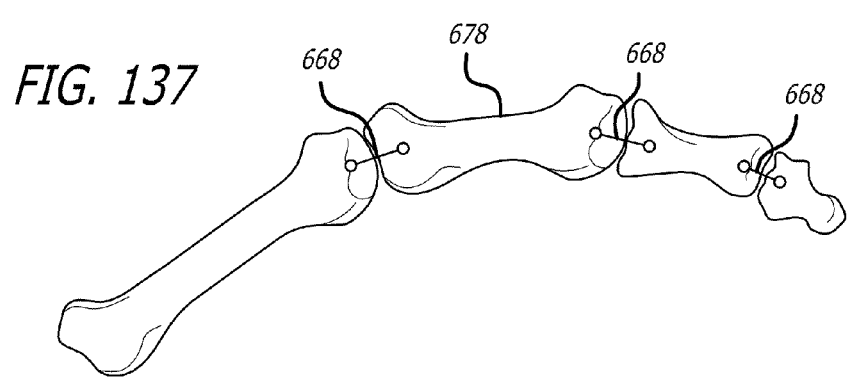
Figure 138:
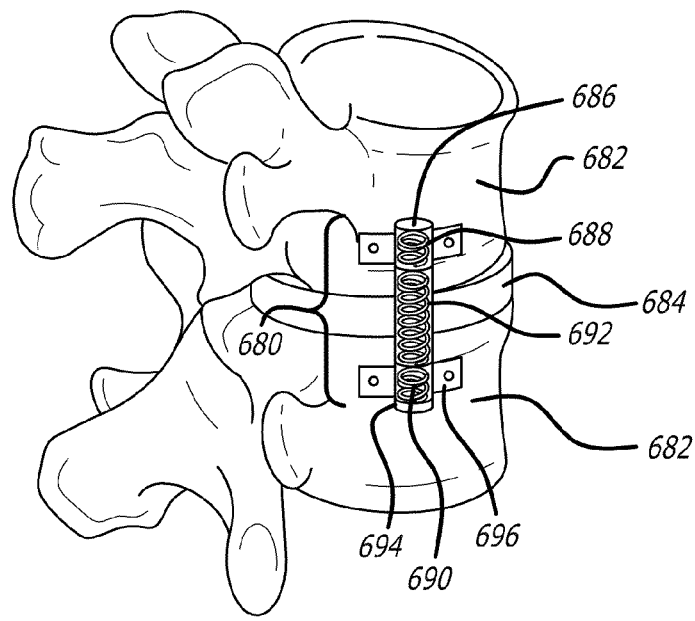
Figure 139:
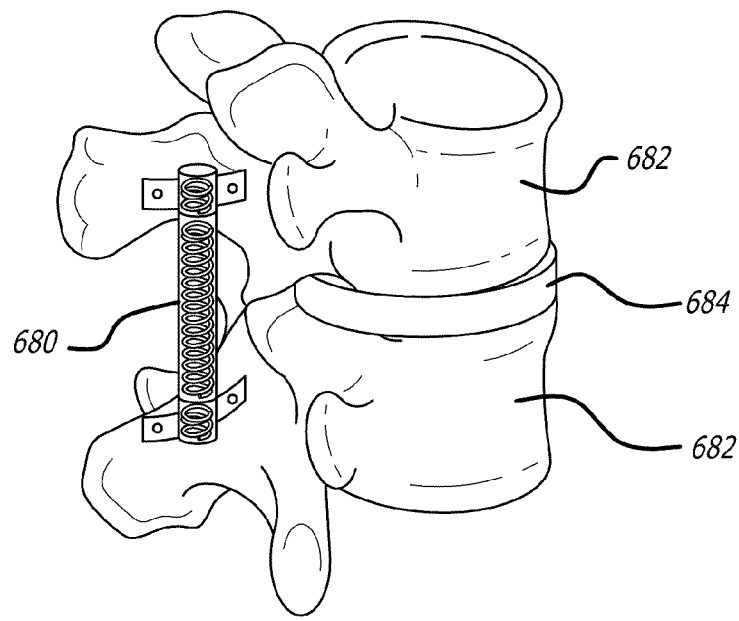

FIG. 132 is a perspective view partially in cross-section, depicting still yet another embodiment of the present invention;

FIG. 133 is a perspective view, depicting the application of the present invention to another body joint;

FIG. 134 is an enlarged view, depicting the energy manipulation assembly of FIG. 132;

FIG. 135 is a side view, depicting the application of the present invention to a foot joint;

FIG. 136 is a top view, depicting the application of the present invention to a finger joint;

FIG. 137 is a side view, depicting an alternate to the approach shown in FIG. 135;

FIG. 138 is a perspective view, depicting the application of the present invention to a spinal joint; and FIG. 139 is a perspective view, depicting another application of the present invention to a spinal joint.

DETAILED DESCRIPTION OF THE PREFERRED EMBODIMENTS

Referring now to the drawings, which are provided by way of example and not limitation, the present invention is directed towards apparatus and methods for treating body tissues. In applications relating to the treatment of body joints, the present invention seeks to alleviate pain associated with the function of diseased or malaligned members forming a body joint. Whereas the present invention is particularly suited to address issues associated with osteoarthritis, the energy manipulation accomplished by the present invention lends itself well to broader applications. Moreover, the present invention is particularly suited to treating synovial joints such as the knee and shoulder. However, it is also contemplated that the apparatus and method of the present invention can be employed to treat the spine facet joints and spine vertebral joints as well as other synovial and various other joints of the body such as those of the hand and feet.

In one particular aspect, the present invention seeks to permit and complement the unique articulating motion of the members defining a body joint of a patient while simultaneously manipulating energy being experienced by both cartilage and osseous tissue (cancellous and cortical bone). Approaches involving varying energy absorption and transfer during the pivoting of the joint and selecting a geometry for the energy absorption assembly to provide necessary flexibility are implemented into various embodiments of the present invention. Certain of the embodiments include geometry which accomplishes variable energy absorption designed to minimize and complement the dampening effect and energy absorption provided by the anatomy of the body, such as that found at a body joint. It has been postulated that to minimize pain, off-loading or absorption of 1-40% of forces, in varying degrees, may be necessary. Variable off-loading or absorption in the range of 5-20% can be a target for certain applications. In certain specific applications, distraction is employed in the energy manipulation approach.

Conventional or surgical or minimally invasive approaches are taken to gain access to a body joint or other anatomy requiring attention. Arthroscopic approaches are thus contemplated when reasonable to both implant the energy manipulation assembly as well as to accomplish adjusting an implanted assembly. Moreover, biologically inert materials of various kinds can be employed in constructing the energy manipulation assemblies of the present invention.

In one particular approach, a bending spring assembly is contemplated to manipulate or absorb forces between body parts. Thus, an assembly utilizing an element or elements which respond to bending or changes in elongation may be desirable to treat afflictions such as osteoarthritis. Certain of the assemblies can incorporate features which insure correct device alignment and prevent against buckling as the member transitions between compressed and uncompressed states.

Figure 3:
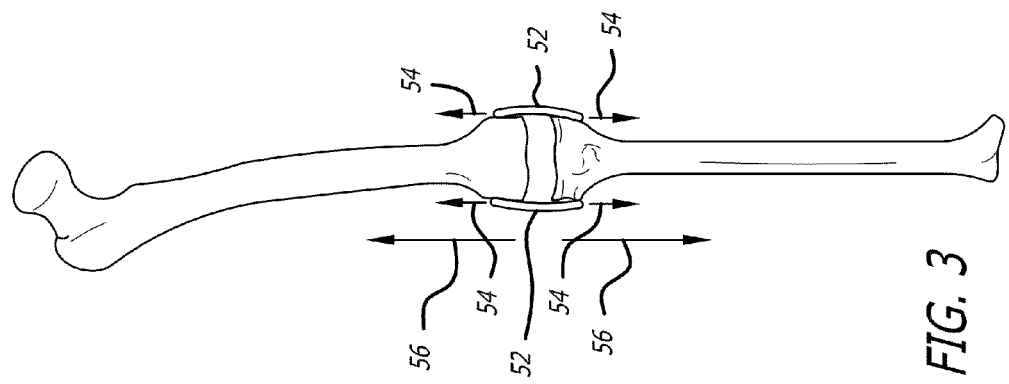
FIG. 3 is a front view, depicting the effect an energy manipulating assembly of the present invention has on the joint shown in FIGS. 1 and 2.
Figure 2:
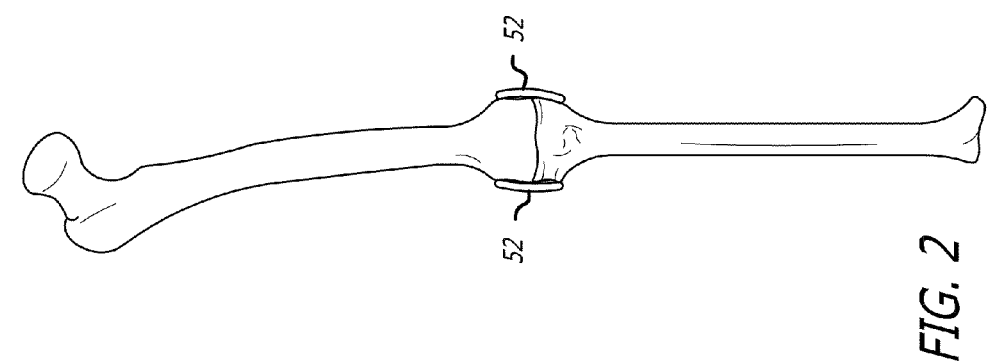
FIG. 2 is a front view, depicting the present invention incorporated into the joint shown in FIG. 1.
Figure 1:
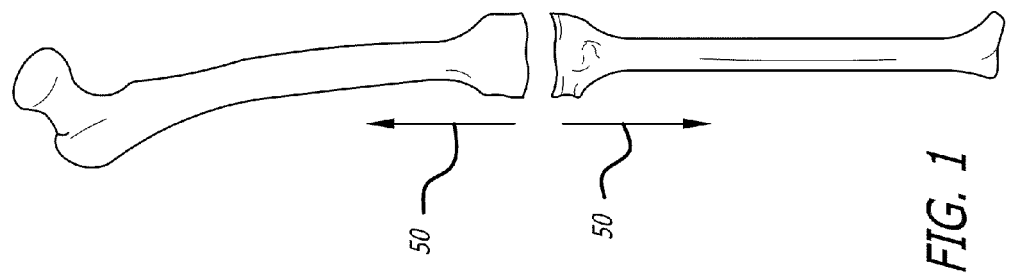
FIG. 1 is a front view, depicting the normal forces existing in a joint.

Turning now to FIGS. 1-3, the forces occurring between body joints is discussed. The arrows of FIG. 1 depict the forces occurring between adjacent members of a body joint lacking an energy manipulation assembly of the present invention. However, in body anatomy incorporating the present invention, less forces are transferred to the bones and cartilage of the members defining the joint. Where the body joint is treated with the foregoing described energy manipulating assemblies of the present invention, a degree of the forces between body members is absorbed by the energy manipulating assembly (depicted as arrows 54). Accordingly, less force 56 is placed on natural body anatomy.

Figure 4:
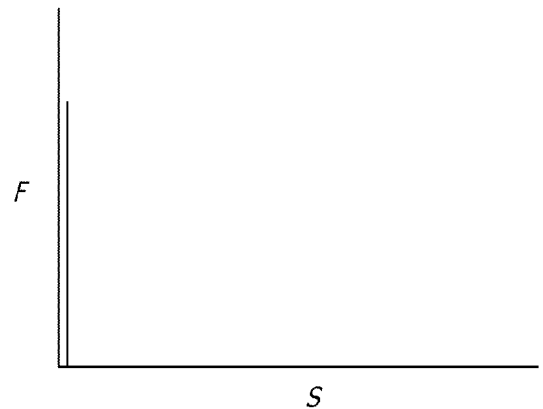
FIG. 4 is a graph, illustrating the energy characteristics of a prior art rigid structure applied across a joint.
Figure 5:
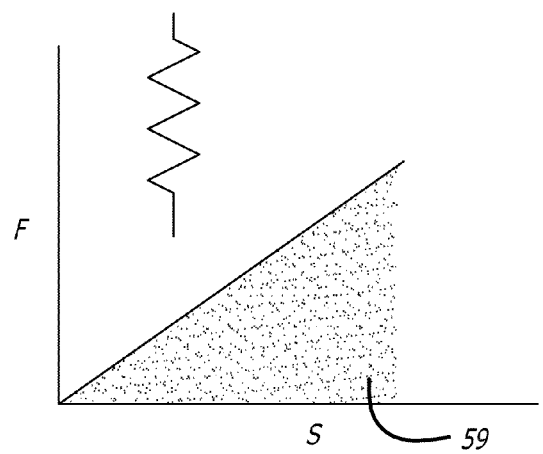
FIG. 5 is a graph, illustrating the energy characteristics of a linear spring system of the present invention.
Figure 6:
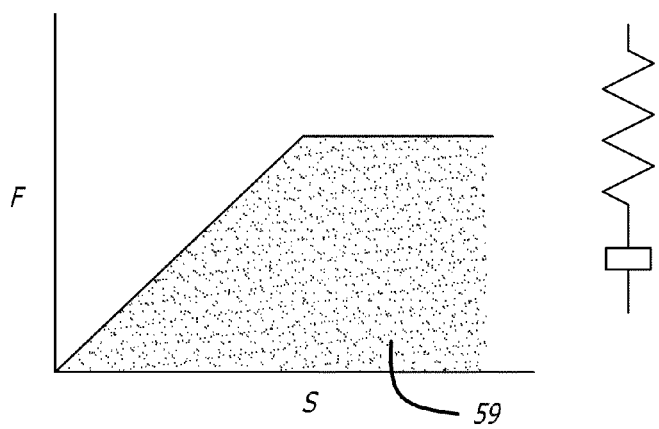
FIG. 6 is a graph, illustrating the energy characteristics of a spring and dampening system of the present invention.
Figure 7:
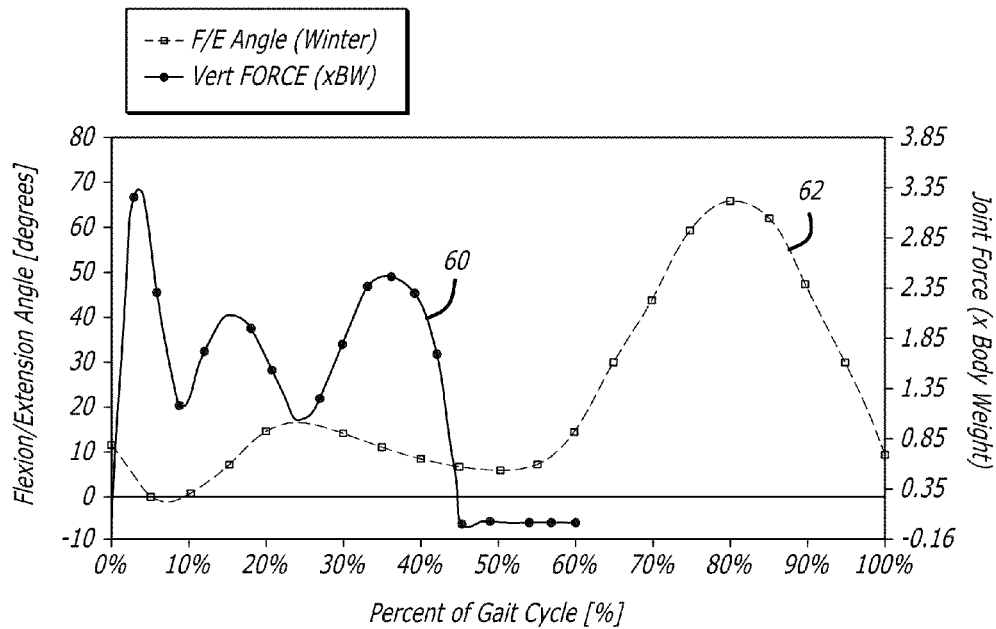
FIG. 7 is a graph, illustrating the flexion/extension angle and joint force existing in a gait cycle.
Figure 8:
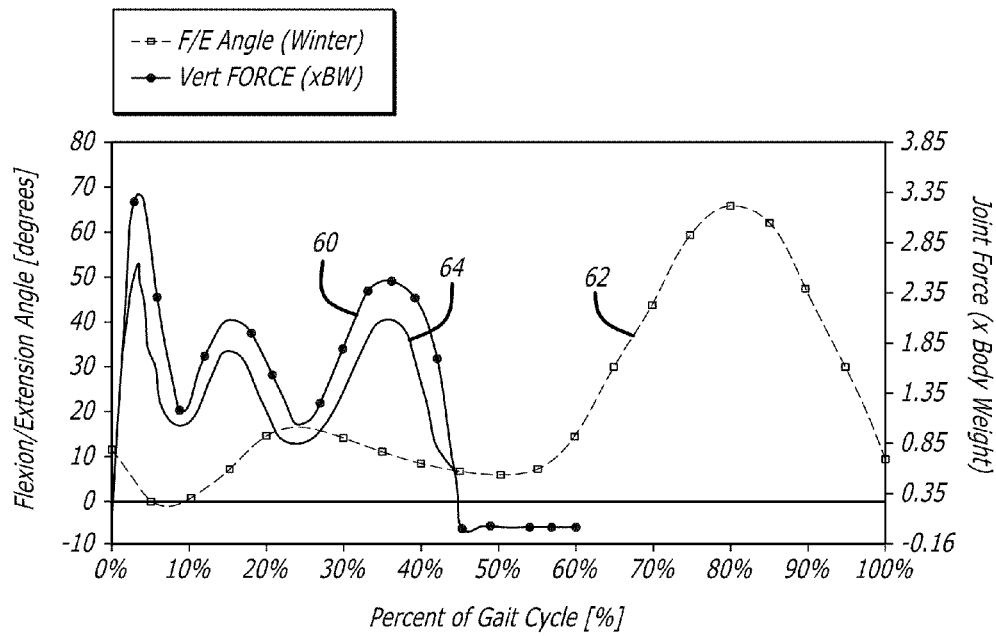
FIG. 8 is a graph, illustrating one approach to energy absorption on a gait cycle.

FIGS. 4-6 depicts the relation between force (F) and displacement (S) between members of a body joint (where mass is constant). In a rigid body system (FIG. 4) which does not incorporate aspects of the present invention, there is no displacement and no energy absorption. In an energy manipulating system incorporating a single linear spring (FIG. 5), energy is absorbed in proportion to a spring constant (spring stiffness). The energy absorbed is represented by the shaded area 59 below the curve. As shown in FIG. 6, where a spring and dampener is used in combination, the energy absorbed 59 is a function of the spring constant and the dampener. It is these relationships which are considered in developing desired energy manipulating characteristics.

Figure 9:
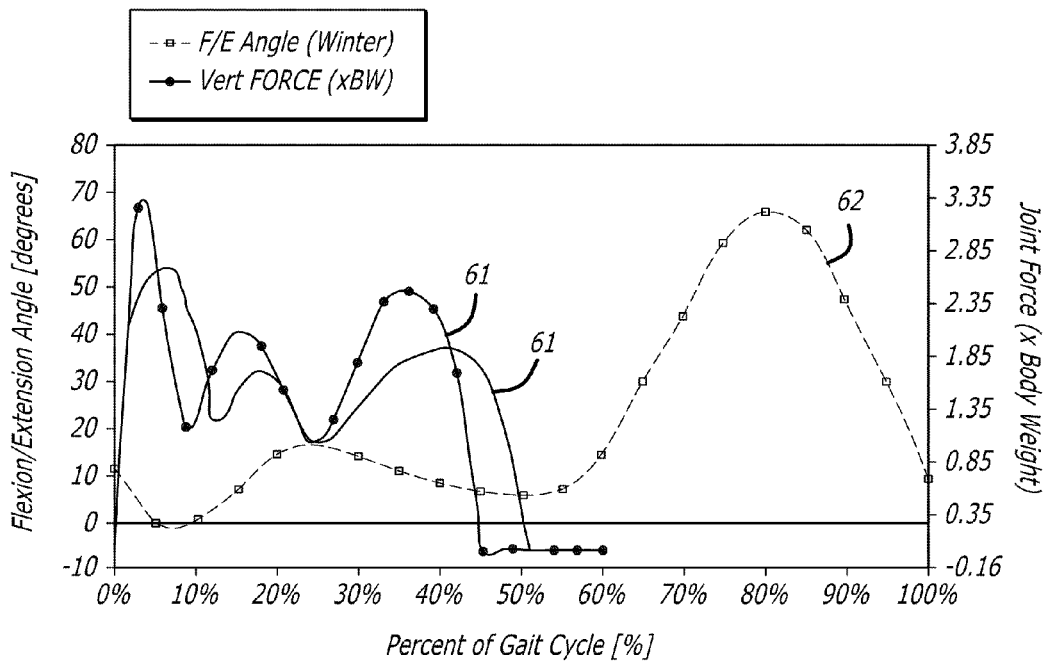
FIG. 9 is a graph, illustrating a second approach to energy absorption on a gait cycle.
Figure 10:
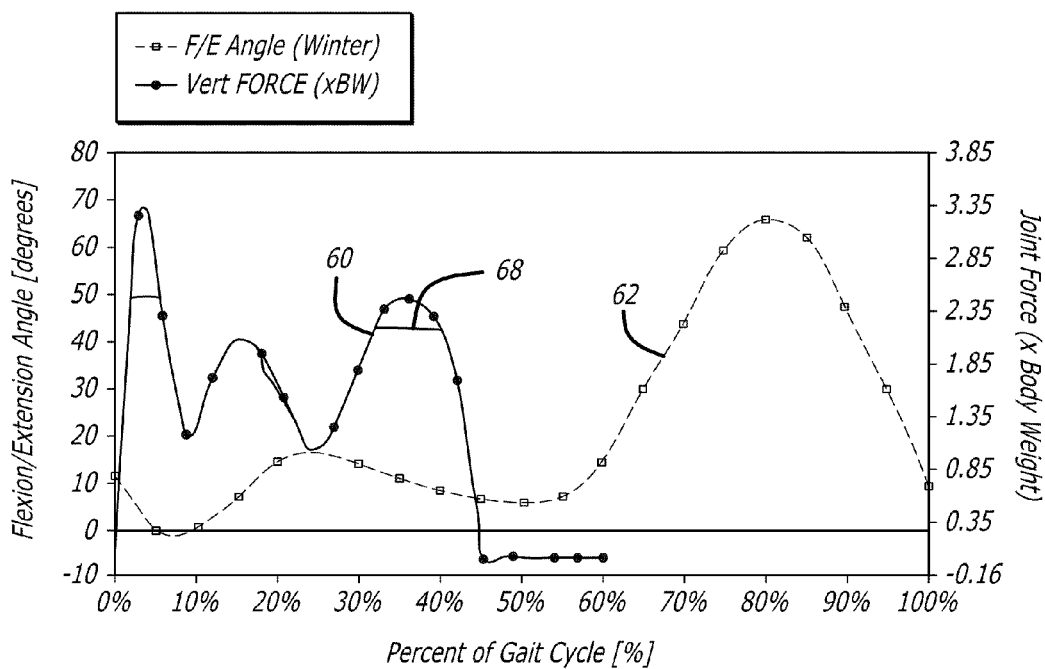
FIG. 10 is a graph, illustrating a third approach to energy absorption on a gait cycle.
Figure 11:
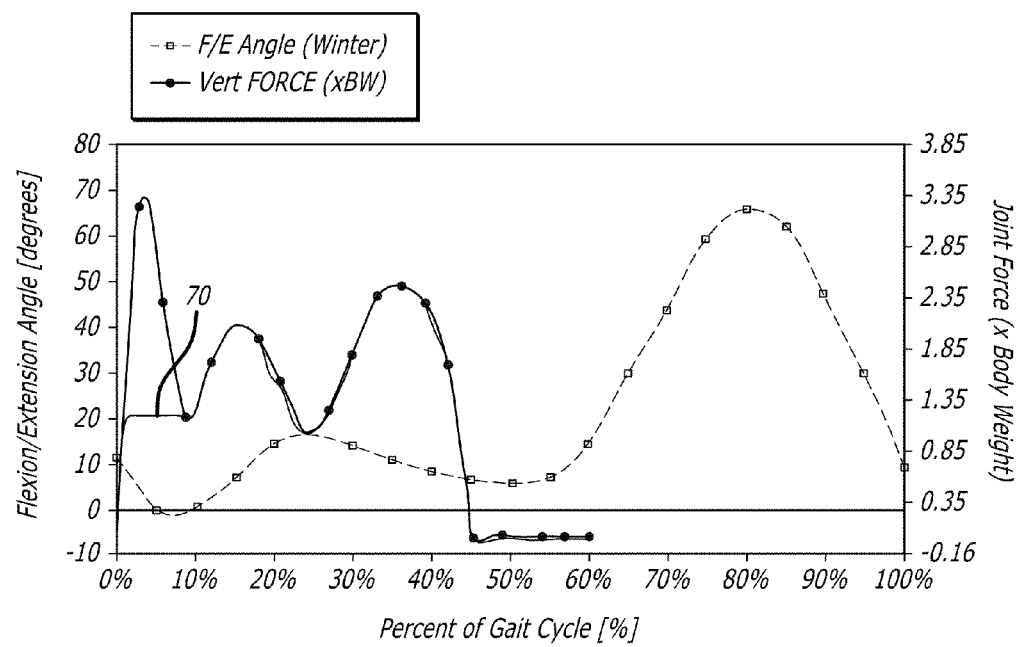
FIG. 11 is a graph, illustrating a fourth approach to energy absorption on a gait cycle.
Figure 118:
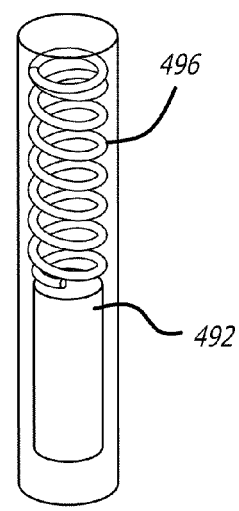
Figure 119:
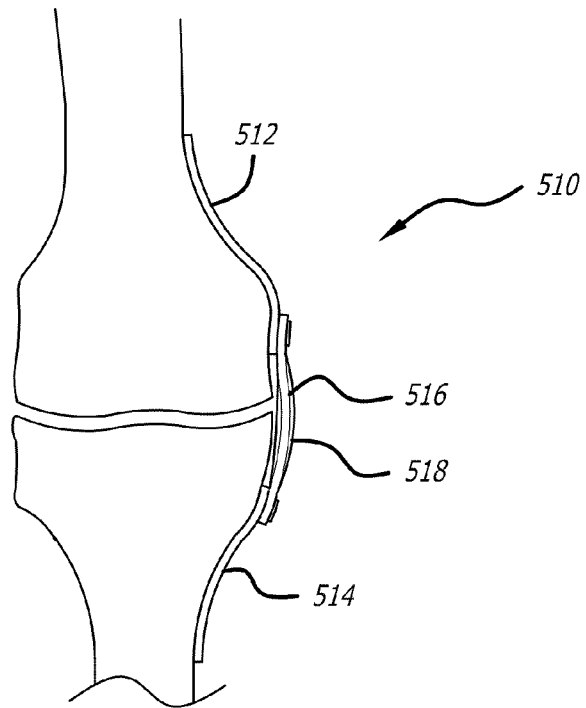
Figure 120:
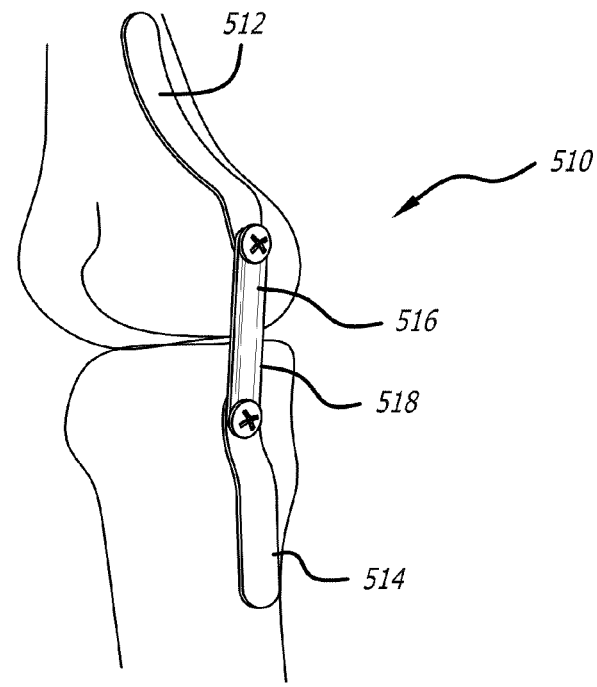
Figure 121:
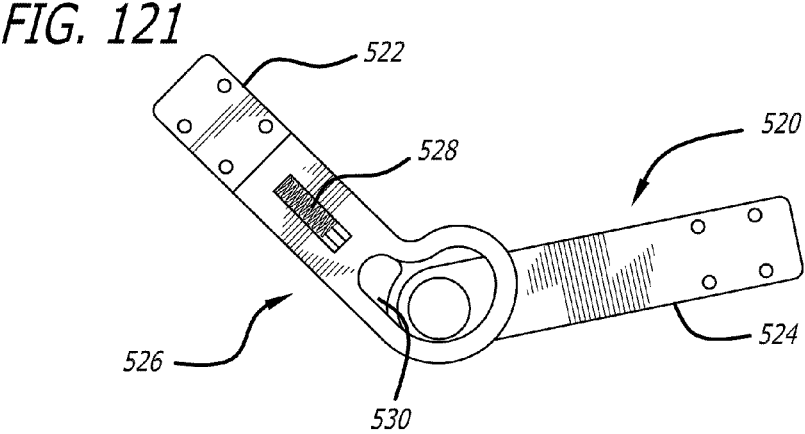

Also considered are the forces existing through the flexion and extension through an articulation cycle of anatomy to be treated. Using the gait cycle of the legs of a human as an example, both the joint force and flexion/extension angle in degrees can be plotted versus the percentage of the gait cycle completed. A normal or expected relationship 60 of vertical forces generated through the gait cycle is depicted in each of FIGS. 7-11. Also depicted in the FIGS. is the flexion/extension angle 62. The expected relationship 60 of vertical forces during the gait cycle can be altered using certain of the embodiments of the energy manipulation assemblies of the present invention. As shown in FIG. 118, the energy manipulation assemblies can absorb energy by a fixed proportion during a portion of the gait cycle. This is reflected by curve 64. Moreover, energy can be both absorbed and dampened as represented by curve 66 of FIG. 9 or alternatively, energy can be absorbed only above a fixed value as represented by curve 68 of FIG. 10. Additionally, as reflected by curve 70 of FIG. 11, energy can be absorbed in a fixed range of motion. It is to be recognized, however, that each of or one or more of these types of energy absorption can be combined in a desired system.

Figure 12:
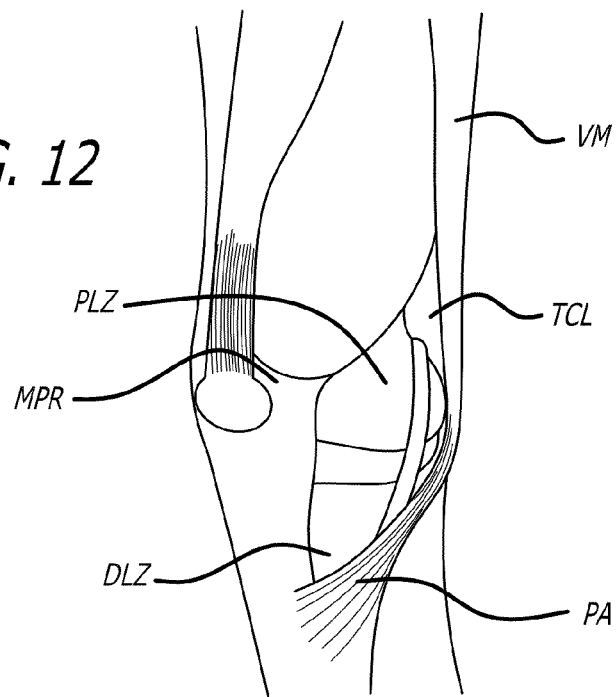
FIG. 12 is a perspective view, depicting anatomy of a typical knee joint.

Referring now to FIG. 12, the medial side anatomy of a typical knee joint is presented in a manner relating to an implantation procedure. Such a procedure could ultimately involve the implantation of devices such as those described below. Although the knee joint is being described here, it is contemplated these devices can also be placed at other joints throughout the body.

In a procedure seeking to off-load or manipulate forces at a knee joint, a proximal attachment site (PAS) for a base component of an energy manipulation device must be identified. Similarly, a distal attachment site (PAS) must also be selected. In a contemplated approach the medial proximal attachment site (PAS) can be located on a femur in a space bounded by the medial patellar retinaculum (MPR), the vastus medialis (VM) and the tibial collateral ligament (TCL). The distal attachment site (DAS) can be located on the tibia in a space between the medical patellar retinaculum (MPR) and the pes anserinus (PA).

Figure 13:
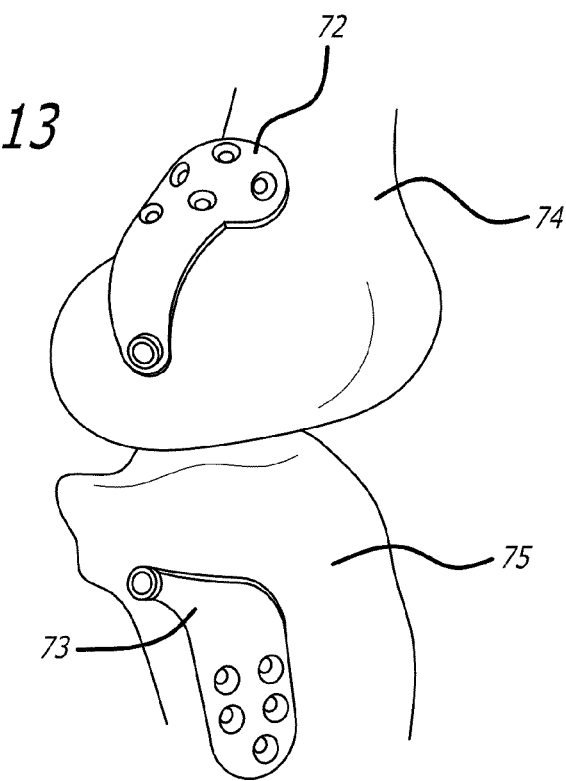
FIG. 13 is a perspective view, depicting proximal and distal base components mounted at a joint.

Turning now to FIG. 13, there is shown proximal 72 and distal 73 base components positioned upon first 74 and second 75 members, respectively of a typical body joint.

Here, the terminal end portions of the femur and tibia are depicted without surrounding tissue. It is noted that the base components 72 and 73 are contoured to match potential mounting surfaces of the femur and tibia. FIG. 14 further shows one embodiment of an energy manipulation device 76 configured between and mounted to the base components 72, 73.

Figure 16:
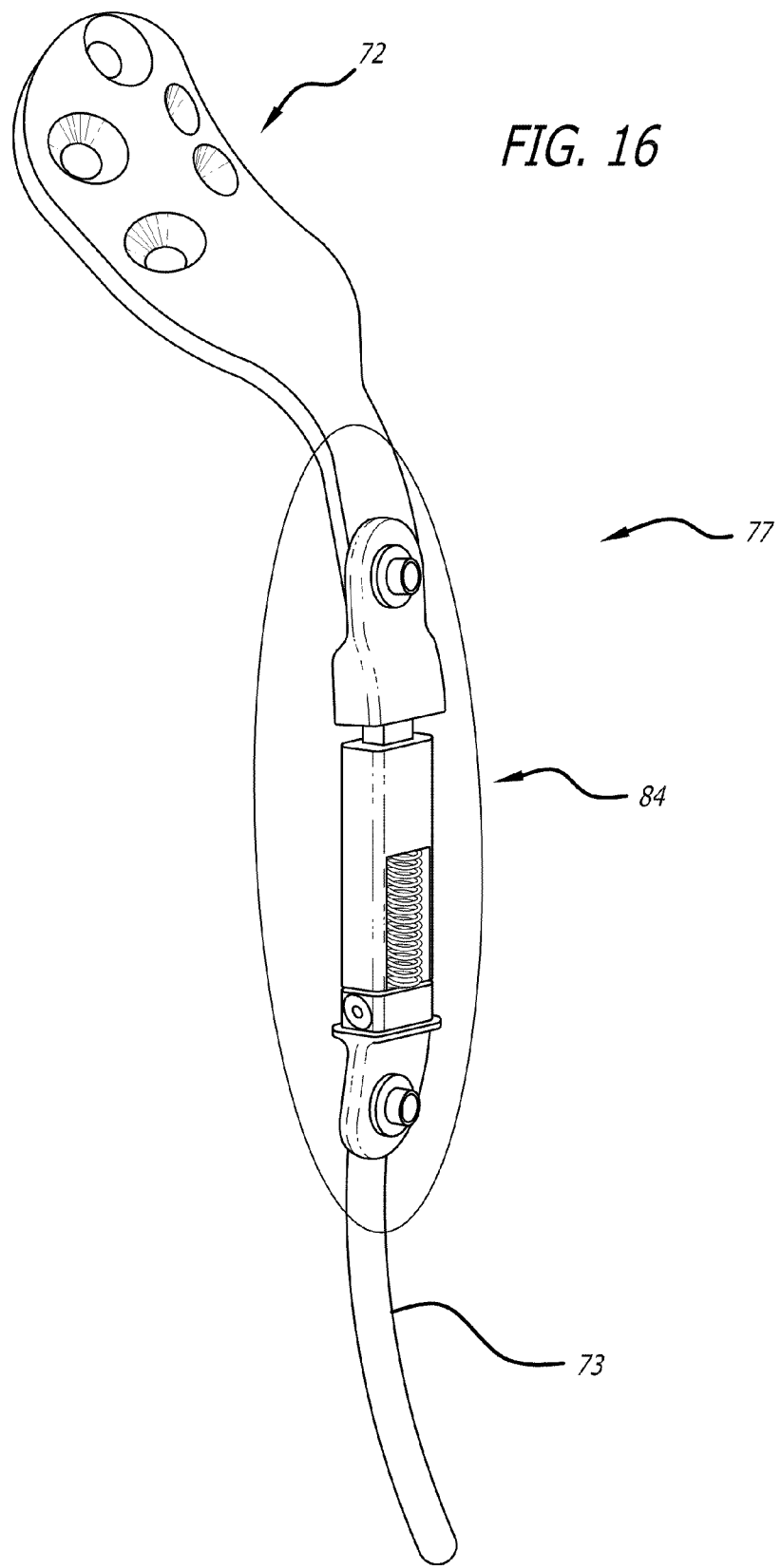
FIG. 16 is a perspective view, depicting the assembly of FIG. 15 including a tissue barrier.

One preferred embodiment of an energy manipulation system 77 is shown in FIGS. 15 and 16. This system includes a proximal base anchor 78 attached to a proximal base component 72 and a distal base anchor 79 attached to a distal base component 73. Articulation surfaces 81 are further provided at a junction between the base anchors 78, 79 and the base components 72, 73. Articulation surfaces 81 allow multiple degrees of freedom between the base anchors and energy absorber assembly 82. Configured between the base anchors 78, 79 is an energy absorber assembly 82 including energy absorbing sub-structure such as a spring, configured within a stabilizer, here shown as sliding sleeves 83. With particular reference to FIG. 16, the system 77 can further include a subcutaneous tissue barrier in the form of a sheath 84, preferably ePTFE, which encloses various parts of the system and excludes surrounding tissue. It is contemplated that the subcutaneous tissue barrier can be formed from or coated alternatively with a tissue in-growth substance or for that matter, substances which inhibit such in-growth. For example, it may be desirable that one or more sides or portions of the energy manipulation system 77 enclosed by the sheath 84 be affixed to surrounding tissue whereas it may be advantageous that other portions of the system be free to move with respect to surrounding tissue. The energy manipulation system 77 itself would be left to move relative to the sheath 84.

With reference now to FIGS. 17-24, aspects of a contemplated implantation approach are described. With the anatomy of the knee joint in mind, a pre-operative session with the patient is conducted. By employing two-dimensional or three dimensional static or motion imaging techniques which are available, such as x-ray, MRI or CT scans, the anatomy of the interventional site is examined. A dynamic assessment can be performed to map the articulating motion of the members defining the particular joint.

The data collected during the pre-operative session is logged and then compared to data sets developed by the physician and/or the organization utilized to store actual patient data as well as tested theoretical data independently developed. Easily accessible and convenient to use programs or charts can be developed and employed to automate the comparison of a particular patient's condition with previously collected data. From this comparison, a specific treatment modality is selected for the patient. Moreover, an expected device selection or multiple device selections are made from the various devices contemplated to treat the patient.

The pre-operative session or an intra-operative session further includes the collection of three-dimensional information concerning an expected proximal attachment site (PAS) and a distal attachment site (DAS). This lends itself to the selection of the proper base components.

Once the surgical intervention date is set and as it approaches, the patient's health is continued to be closely monitored. On the day of the procedure, the patient is prepared for surgery in the conventional manner. In a particular application, spinal anesthesia or general anesthesia can be used as a step to prepare the patient.

Next, the knee or other joint being treated is imaged using fluoroscopy (See FIG. 17) or along with three-dimensional navigational software such as that available from Striker or Brainlab. The members defining the joint are placed in a full lateral position and perpendicularly to the receiver of the imaging device. The proximal joint member is then fixed using a vacuum splint/sandbag (not shown) or similarly effective device. In a preferred procedure to treat the knee joint, the Blumensaat's line 85 of the femur bone 86 is used as a landmark for locating the various components of an energy manipulation device as it has been found to provide a convenient initial position marker for ultimately achieving proper rotational positioning of the device. Other referencing points can additionally be used and of course are required when treating other joints.

Accordingly, it is further contemplated that other regions can represent possible locations of a femoral rotation point on the medial chondyle. In order to select such an alternative point, the surface area of the medial chondyle is mapped to determine regions corresponding to changes in device length of a potentially implanted energy manipulation assembly while the joint is moved from full extension to full flexion. Areas of device increasing length and decreasing length are mapped. Moreover, areas are also identified where there is an initial device length increase then followed by a length decrease, and where there is an initial length decrease followed by increasing length. Mapping of areas of overlap between these various areas represent transitions from one region to a next. An area representing minimal displacement is also identified. This information is then employed to identify the various points of rotation best suited for a particular energy manipulation implant. As length change is contemplated to be insensitive to a tibial rotation point, the tibia point therefore remains fixed.

Furthermore, an approach to proper implant placement can involve observing changes in device length at 90° flexion relative to a fully extended length. These length changes are measured relative to a femoral rotation point at a midpoint of the Blumensaat's line shown in full lateral view of the medial side. The device and rotation point is then selected based upon desired measurement changes. The tibial rotation point is then identified by selecting a point directly inferior to the femur rotation point.

Figure 18:
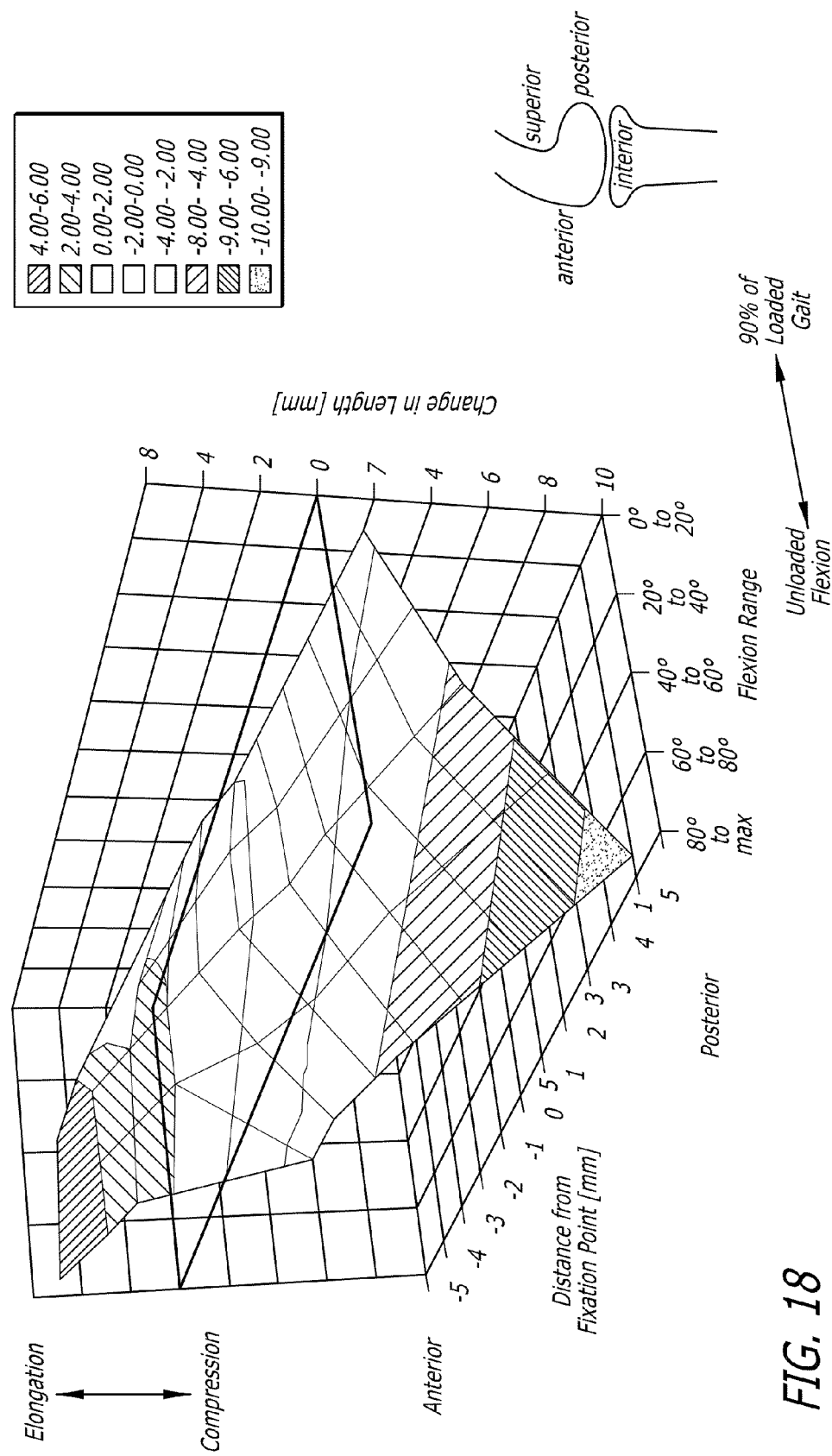
FIG. 18 is a diagrammatic view, depicting motion patterns and selected fixation points for energy manipulation devices.

In at least the first described approach, a circle guide is then placed over the joint with the center thereof configured at a midpoint of the Blumensaat's line (FIGS. 17A and 17B). As shown in FIG. 18, it has been found that when considering device elongation and compression, along with anterior and posterior device positioning as well as flexion degrees during a patient's gait, that +/−5 mm from a center point of a Blumensaat's line can be a starting reference point. At this point, it is confirmed that the tibial plateau at 90° flexion is 1-2 rings outside of an initial matching circle at 0° flexion, if the device selected for the patient is only meant to extend during flexion. At a mid-point of the Blumensaat's line and perpendicularly thereto, the physician will then insert a rigid guide or K-wire 87 through a center guide hole 88 of the circle guide 86 that has been previously locked in place. The K-wire 87 includes a sharp terminal tip for entering bone and thus the K-wire 87 can either be drilled into the bone or tapped in by force. After the K-wire 87 has been fixed perpendicularly to the bone, the circle guide 86 is removed and the K-wire is shortened leaving approximately one inch of wire protruding through the skin. A proximal base component mount hole is then configured over the K-wire placed adjacent the leg to estimate proper placement while using remote image techniques.

With specific reference to FIGS. 19 and 20, an incision 89 is made superior to the K-wire 87. Fascia and tissue are then manipulated to expose bone periostium in the region of anticipated base component attachment. The periostium is next displaced to promote osteointegration. The proximal base component 72 is inserted within the incision 89 and a mounting hole of the proximal base component 72 is placed over the K-wire 87. In order to do so, the skin will require retracting beyond and away from the K-wire 87 to place the mounting hole 90 of the proximal base component 72 over the K-wire 87. The proximal base component 72 is then positioned to optimize fit and bone screws 91 are employed to fix the base component 72 to the bone. An intermediate step can include loosely attaching the base component 72 prior to completely turning down the bone screws 91 so that a most advantageously placement is achieved. It is to be further recognized that various angles of insertion of the bone screws 91 can be used to aid in providing attachment support in a multitude of directions. Moreover, bi-cortical penetration of the bone screws is contemplated for certain applications.

In one approach, it is contemplated that bicortical screws can be polyaxial because their trajectory will be fixed by the bicortical purchase. Their trajectories can either diverge or converge by about 15 to 30 degrees to improve pull out strength but the exact angle is probably not important so the technique can be simplified by letting them rotate in a small cone. Further, the unicortical screws can have fixed trajectories. This will increase their stability that they may lack because of the unicortical purchase. The trajectories should either converge or diverge as above but the angles will be set. Moreover, it is contemplated that none of the screws "lock" to the plate via a second set of threads. This may reduce the ability to generate compression between the bone and the porous coatings and as there may be a need to reduce/eliminate as many gaps as possible. It may further be desirable to use a resorbable bone void filler under the plate to eliminate gaps and prevent ingrowth of fibrous tissues. This might also provide some leeway when the plate shapes are not exact. Finally, an anti back-out feature is contemplated for the screws in certain applications.

Figure 21:
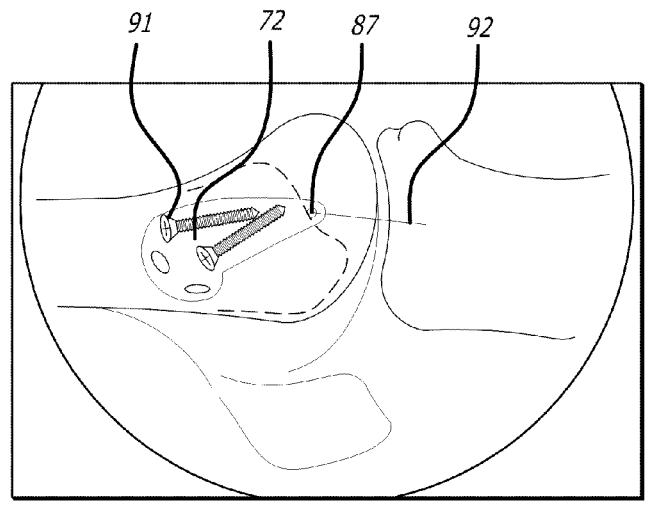
FIG. 21 is an elevation view, depicting yet a further step in an implantation procedure.
Figure 22:
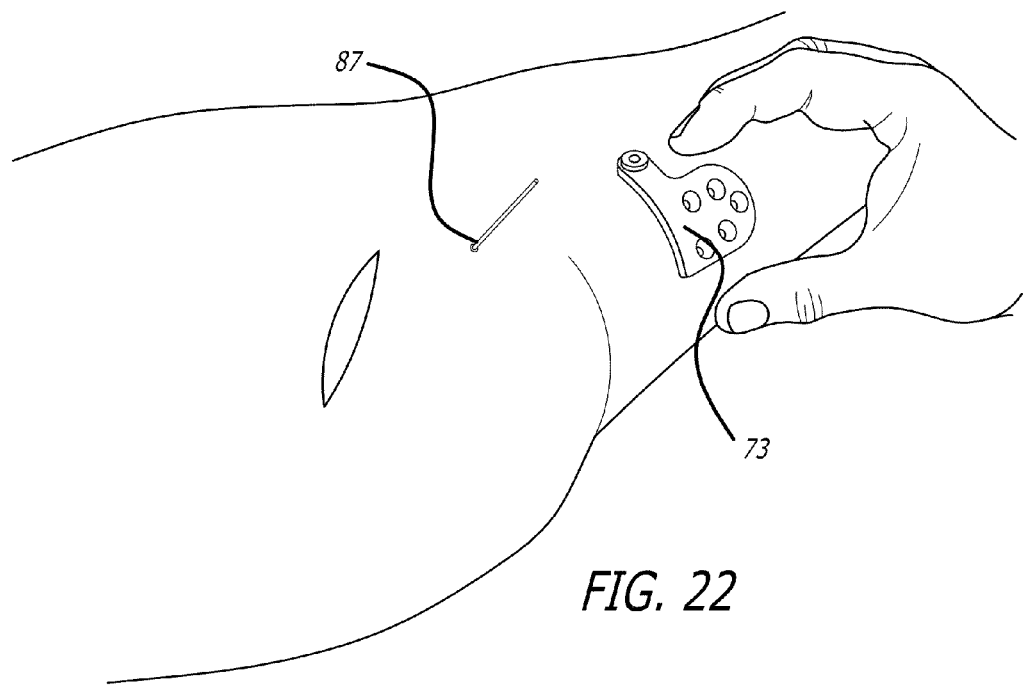
FIG. 22 is a perspective view, depicting yet still a further implantation procedure step.
Figure 25A:
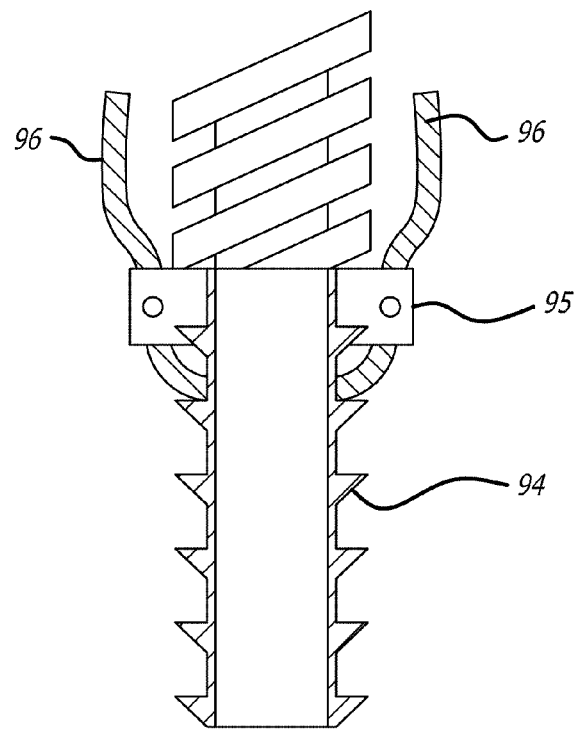
FIG. 25A is a partial cross-sectional view, depicting one embodiment of adjustment sub-structure.
Figure 25B:
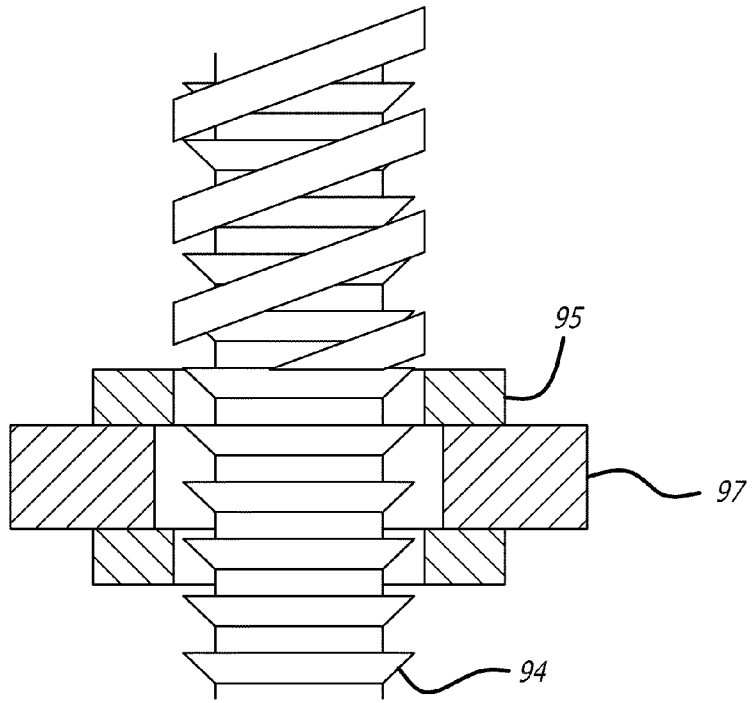
FIG. 25B is a partial cross-sectional view, depicting another embodiment of adjustment sub-structure.
Figure 25D:
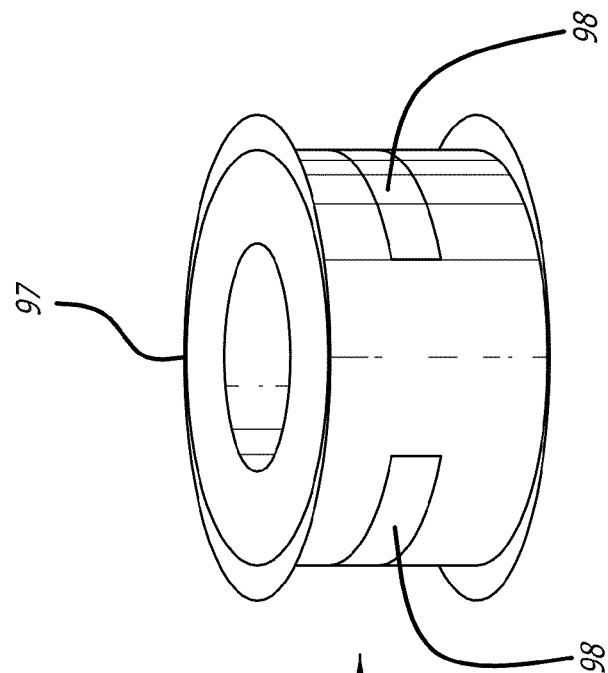
FIG. 25D is an enlarged view, depicting the adjustment ring of FIG. 25C in a ratchet release state.
Figure 25C:
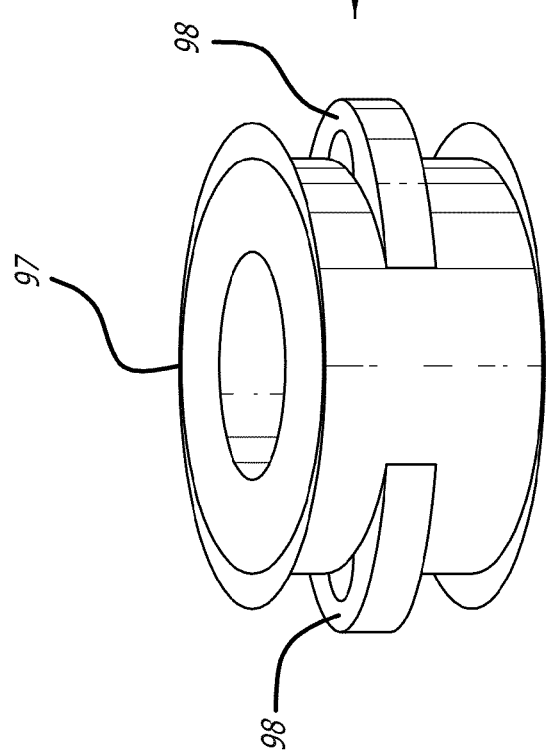
FIG. 25C is an enlarged view, depicting an adjustment ring of FIG. 25B shown in a ratchet engaged state.

Turning now to FIGS. 21-24, the location and fixation of a distal base component 73 is described. With the joint members, here the femur and tibia, placed in a fully extended position, a vertical line is taken down from the mounting hole 90 of the proximal base component 72 to a distance approximately 45 mm-55 mm along the tibia. The circle guide 86 can again be used to aid in this step. Alternatively, as shown in FIG. 21, a tibial guide cross-bar device 92 can be placed to engage the K-wire 87 at one end and using remote imaging, arranged so that a guide cross bar thereof is perpendicular to a top of the tibial surface. The location of the distal base component 73 is then estimated both visually on the outside of the skin as well as remotely such as by using fluoroscopy or other techniques.

The skin is then incised 93 along the distal joint member or in the present application, along the tibia. Alternatively, the first incision can be used to access the distal joint member via a subcutaneous channel. In this regard, one long incision can alternatively be used extending across the joint members. Also, a single small incision can be made at the center of the joint or on either side of a joint from which a tunnel is formed to access a target site on either side of the joint. The fascia and tissue in the area is manipulated to expose bone periostium in the target region and the bone is displaced to again promote bone in-growth into a subsequently placed distal base component 73. The distal base component 73 is then positioned to optimize fit and bone screws 91 are inserted to affix the component to the bone.

Again, prior to completely turning the screws to fix the base component, further adjustment is contemplated.

Subsequent to forming a subcutaneous channel between the base components, the energy absorber sub-assembly 76 of the energy manipulation device is then attached to the base components 72, 73. Although various embodiments of the energy manipulation device are contemplated, in general, the device will include replaceable and adjustable proximal and distal articulate structure (e.g., ball and socket joints, U-joints/limbs) attached to the base components 72, 73 as well as a replaceable and adjustable mid-section accomplishing the energy manipulation. A sheath is further provided about these structures to protect the surrounding tissue. The sheath can form part of this sub-assembly or be added later. In attaching such structure to the base components 72, 73, the members defining the joint are placed in full flexion in order to minimize spring force.

Once the energy manipulation device is completely implanted, the incisions are closed and allowed to heal. Subsequent post-operative steps are taken to verify proper placement and to accomplish any necessary adjustment. In this regard, two or three-dimensional states of motion image techniques can be used to observe effectiveness. That is, in one approach, it is desired that the spring or other energy manipulation sub-structure be compressed 80-90% at full extension of the joint members. It also may be desired to configure the implant so that no loads are initially placed thereon. Once it is determined that the implant has completely attached to the bone and the area has healed, it is then adjusted to achieve load manipulation. Multiple subsequent adjustments or component replacement are also contemplated as well as percutaneous approaches to the same.

In an alternative related approach to implantation, a scan of the target joint is performed. Natural or added landmarks can be employed during the scanning step for orientation purposes and the patient's need are accessed and documented. The data extracted during the scanning procedure is then imported into a three dimensional (3D) navigational software and associated tracker. The tracker can employ RF, optical, or electromagnetic energies and can be self-powered or be passively powered. A guidewire delivery tool is then attached to the tracker. Software is activated to automatically manipulate the tracker into a desired position relative to the landmarks. A reference tool is then imported to the area for guidewire delivery on bases proximal and distal to a target joint. Next, orientation of a guidewire trajectory point is performed based upon pre-calculated ideal points as determined by desired functional needs of the periarticular joint.

Once guidewires are placed on the members defining the joint, a proper base component can be selected based upon three dimensional data gathered concerning the anatomy of the target joint. After gaining access to the bones and completing other preliminary steps described above, the base components can be fixed to the bones employing screws or the like. Thereafter, rotation points are attached to the base components and the tracker is again employed to perform fine adjustments as to fine tune locations of the structures. Finally, the energy manipulation substructure is placed between and connected to the rotation point assemblies.

The fact that the implant will be relatively superficial presents the opportunity to allow interaction with it through the skin without puncture. The concept is that the height of the piston (or other energy manipulation structure) engagement would be adjustable by squeezing the device on either side when the device is completely unloaded (flexed position). It is contemplated that a core shaft of an implant can be ribbed like a ratchet, and the movable piston (or other sub-structure) is mounted on a collar that has two relative large "buttons" on either side. Depression of the buttons causes the teeth on the inside of the collar to disengage when the device is completely unloaded. Compression on only one button does not release either of the teeth—only both buttons releases the teeth. Further, due to the morphology of the teeth and the ratchet, the assembly can be arranged so that even depression of both teeth when the device is loaded will not release the collar. Thus, inadvertent release during loading could not occur. Every time the collar is moved up or down while the buttons are being depressed in the unloaded position there can be an audible click. Accordingly, without x-ray the doctor can adjust the device in the office and a table can be provided for the significance of the clicks with respect to un-loading. Firm finger pressure on the device in the unloaded position would be enough to disengage the collar and relocate it to a new position. Local anesthetic on the skin and a pincher tool can be used while employing fluoroscopy to find the buttons, depress them and relocate the housing to a new position.

Turning now to FIGS. 25A-D, there is shown approaches to adjusting an energy absorber assembly. In the approaches depicted, the assemblies include a ratchet core 94 including outwardly projecting and angled teeth. A spring-biased collar piston assembly 95 is further provided and configured in a lockable arrangement with the ratchet core 94. In a first approach (FIG. 25A), the collar/piston assembly 95 is further provided with spring biased button 96 (here shown biased in a closed position by an elastomeric ring) having a distant terminal end. As the buttons are each depressed inwardly, this engagement with the teeth of the ratchet core disengages, thereby allowing the assembly 95 to move up or down. As the assembly 95 is so translated an audible sound is made between the detents of the buttons and the ratchet core 94.

In a second approach (See FIGS. 25 B-D), the spring-biased collar/piston assembly 95 is equipped with a two piece collar spring 97 which can assume both ratchet engaged (FIG. 25C) and ratchet released (FIG. 25D) configurations. Thus, by pressing on the spring arms 98 of this embodiment of the spring-biased collar/piston assembly 95, the collar disengages from the ratchet core 94 and is permitted to be translated longitudinally. As a safety measure, it is to be appreciated that the angle and length of the teeth formed on the ratchet core 94 and corresponding engaging structures of the collar assemblies can be configured to only allow translation if two points of the collar are sufficiently pressed.

Figure 26A:
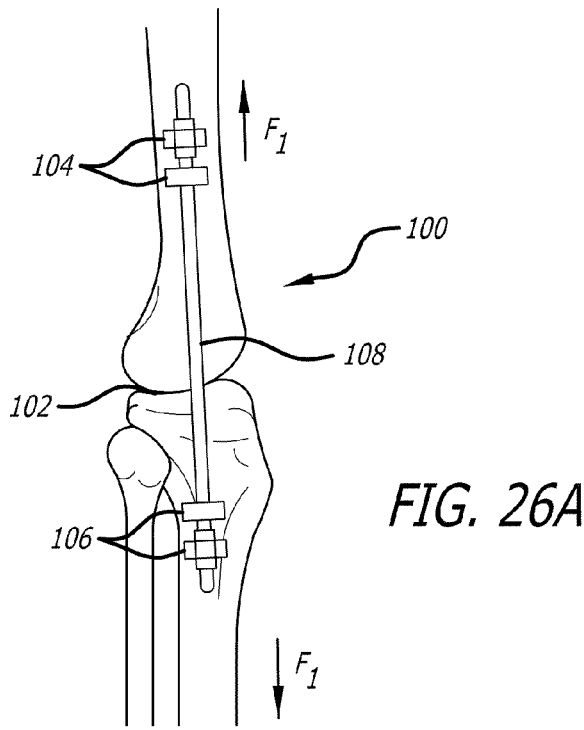
FIG. 26A is a side view, depicting an energy manipulation assembly of the present invention.
Figure 26B:
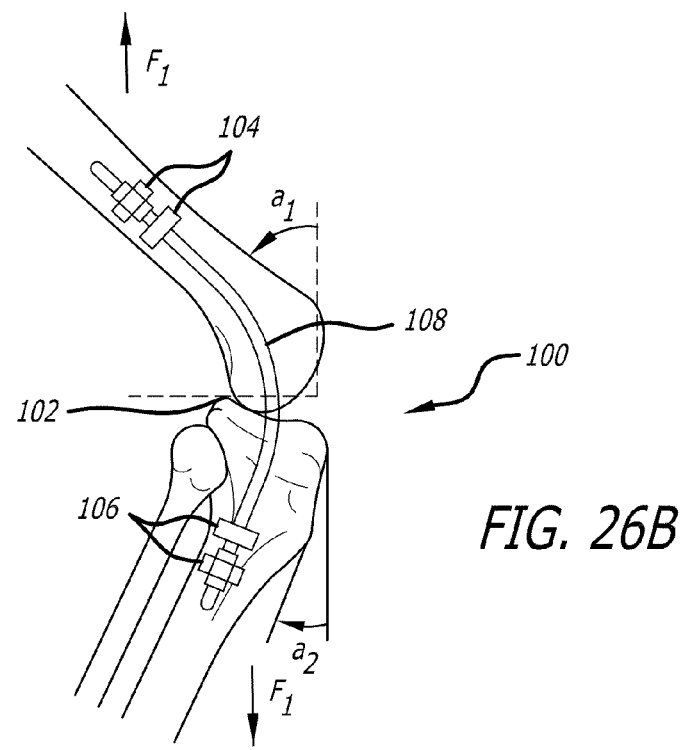
FIG. 26B is a side view, depicting the assembly of FIG. 26A after articulation of body members.

As shown in FIGS. 26A and B, one embodiment of a bending spring assembly 100 can be configured along members forming a body joint 102. The bending spring assembly 100 includes one or more attachment structures 104, 106 and a energy absorbing member 108. The attachment structures 104, 106 are anchored to the members or bones forming the body joint 102. The energy absorbing member 108 is in the form of a bending spring and is attached to each of the attachment structures 104, 106. While the members defining the joint 102 are generally longitudinally arranged, the energy absorbing member 108 absorbs and/or transfers forces being bared by the members of the joint. In a simplified approach, the energy absorbing member 108 can also apply lateral forces to the member of the joint 102 during flexion.

Figure 27:
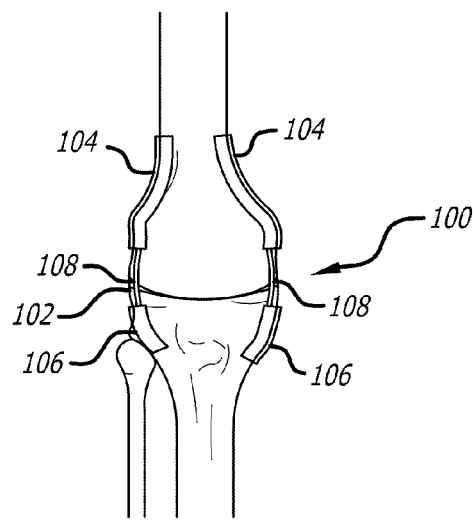
FIG. 27 is a front view, depicting a bi-lateral (or lateral and medial) application of a lower manipulation assembly of the present invention.

As shown in FIGS. 26A and B, a bending spring assembly can be affixed to either a lateral or medial side of a body joint 102. Furthermore, as depicted in FIG. 27, and as well as with each of the disclosed embodiments, bending spring assemblies can additionally be placed on both lateral and medial (or bilateral) surfaces of a body joint 102. Moreover, the energy manipulation achieved by a system of a plurality of bending spring assemblies 100 can be configured to provide different energy manipulation on opposing sides of a joint 100 to thereby accomplish a more complex energy absorption curve and where desired variable off-loading, while permitting and complementing the unique path of motion of the members of a joint of a particular patient.

Figure 28:
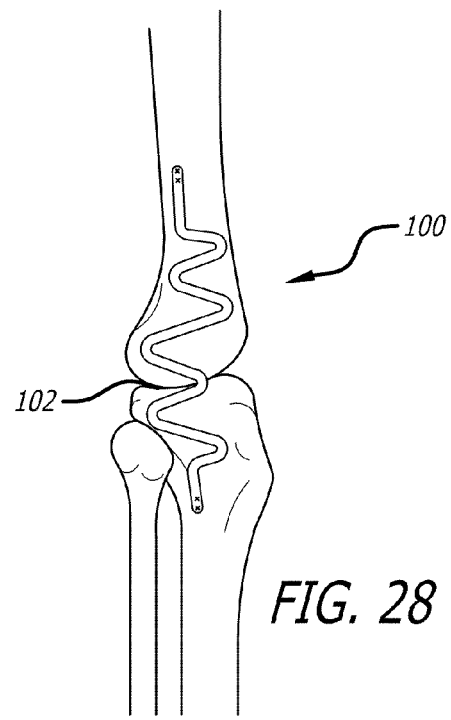
FIG. 28 is a side view, depicting a bending spring energy manipulation assembly of the present invention.
Figure 29:
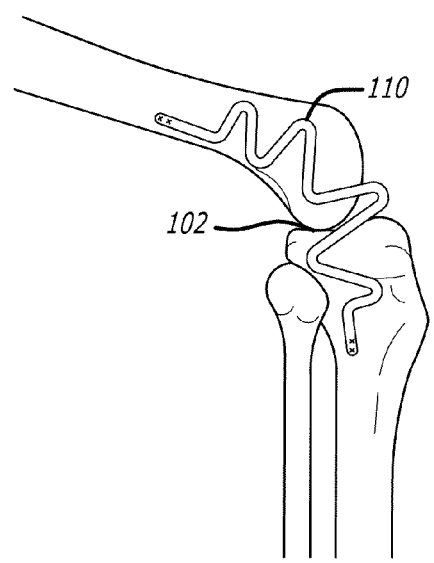
FIG. 29 is a side view, depicting the assembly of FIG. 28 after articulation of body members.
Figure 30:
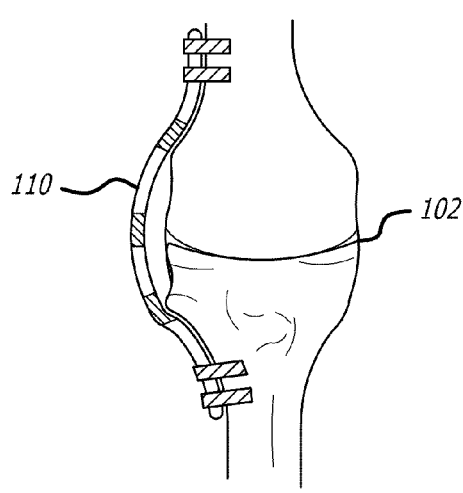
FIG. 30 is a front view, depicting the energy manipulation assembly of FIG. 28.

One particular approach to providing variable energy manipulation while complementing the unique motion of members defining a joint is depicted in FIGS. 28-30. A energy absorbing assembly including an undulating spring member 110 having a variable path can be attached to members defining a body joint 102. The variability of the path is selected to provide additional dampening and/or energy absorption to thus off-load one or more of the cartilage or osseous bones of the joint. Moreover, the energy absorbing spring assembly 110 can be configured to provide such energy manipulation during extension and to become less active during flexion of the members of a joint 102.

Figure 31:
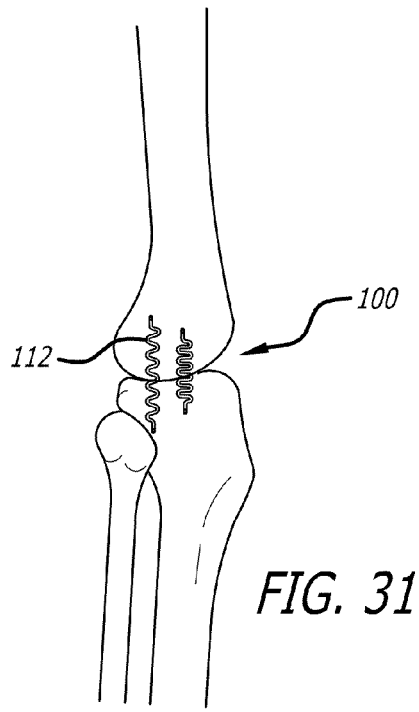
FIG. 31 is a side view, depicting a energy manipulation assembly including a pair of springs.
Figure 32:
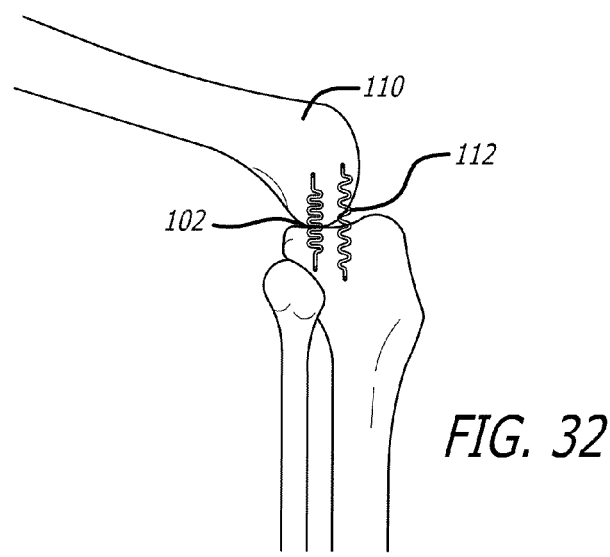
FIG. 32 is a side view, depicting the assembly of FIG. 31 after articulation of body members.
Figure 33:
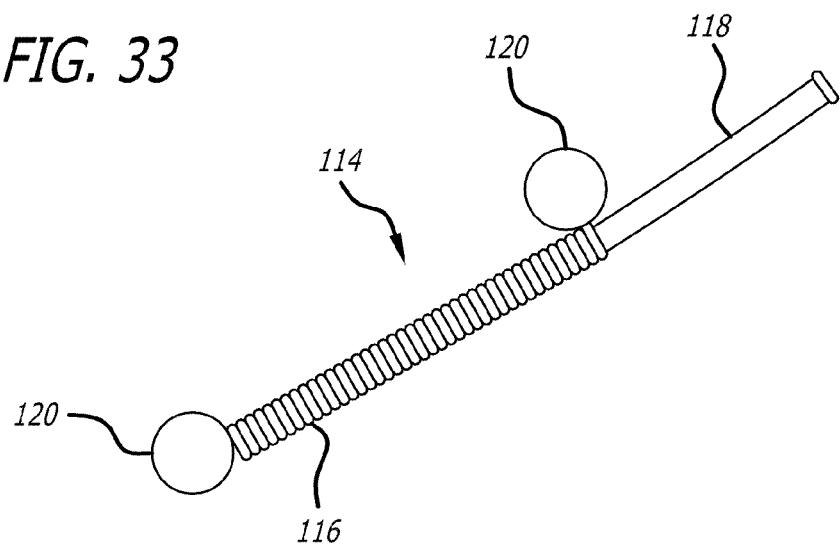
FIG. 33 is a perspective view, depicting a bending spring energy manipulation assembly including a guide shaft.

Turning now to FIGS. 31 and 32, there is shown another approach to energy manipulation employing a bending spring approach. Here, the bending spring assembly 112 includes a pair of springs attached on the same side of a body joint 102. In this approach, the springs can provide energy manipulation in both flexion and in extension. As shown in FIG. 31, the compressed spring provides central off-loading in a direction normal to joint structure and the extended spring is uncompressed so as to not distract a posterior section of the joint. When the members of the joint are in flexion (FIG. 32), the posterior spring provides energy manipulation normal to the direction of the lateral member of the joint while the centrally located spring provides no off-loading. Other combinations of bend spring assemblies 112 are further contemplated to accomplish other energy manipulation scenarios which may be useful in minimizing joint pain.

Further specific geometries of bending spring assemblies are depicted in FIGS. 33-41. Each of these devices contemplate approaches to energy manipulation which complement the unique motion of a joint of a particular patient. In a first embodiment, the bending spring assembly 114 includes a helical spring 116 configured about a guiding member 118. The helical spring 116 is further configured between anchor points 120 which are affixed to a patient's anatomy. As the members defining a body joint articulate, the anchor points 120 move with respect to each other, the guiding member 118 providing a controlled path for the spring 116 and the spring 116 thereby provides the desired energy absorption and/or load transfer.

Figure 34:
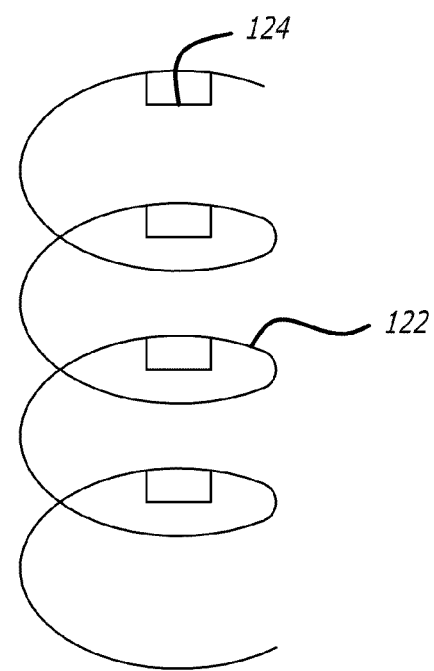
FIG. 34 is a side view, depicting a energy manipulation assembly including locking structure.

As shown in FIG. 34, a helical spring 122 of a bending spring assembly can include interlocking structure 124 which alters the function of the spring 122. For example, the interlocking structure can be adapted to prevent rotation of the spring 122 at a predetermined amount of compression or extension of the spring 122. Thus, a variable energy manipulation can be provided by this structure. Moreover, such structure can alternatively or additionally be employed to prevent or control joint rotation at a given degree of extension or flexion.

Figure 35:
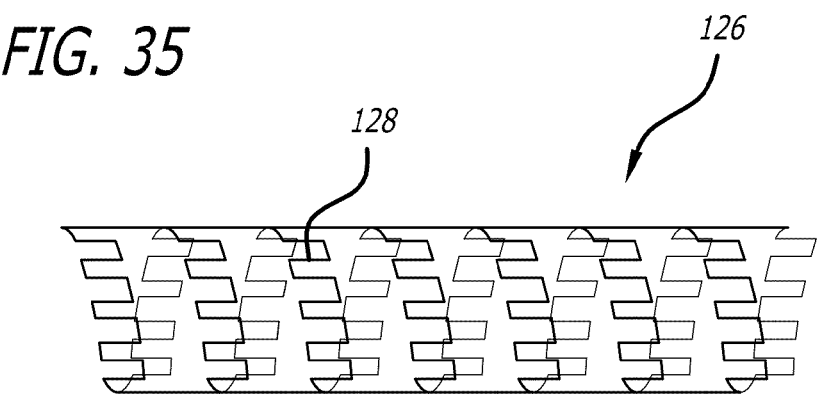
FIG. 35 is a side view, depicting an energy absorbing spring assembly including undulations configured along a helical path.
Figure 36:
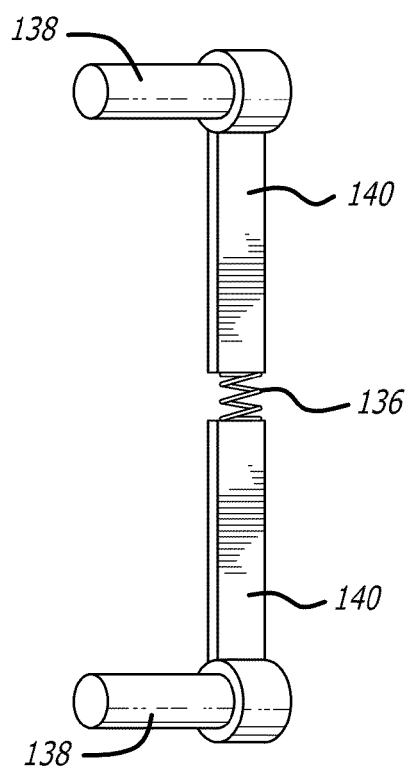
FIG. 36 is a perspective view, depicting a energy manipulation assembly including load bearing members and a central spring.
Figure 37:
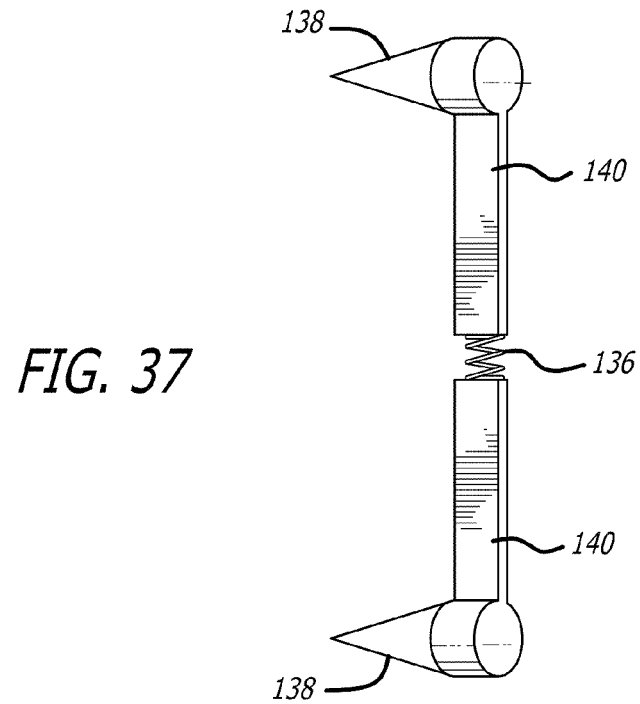
FIG. 37 is a perspective view, depicting another embodiment of a bending spring assembly with a midsection spring.
Figure 38:
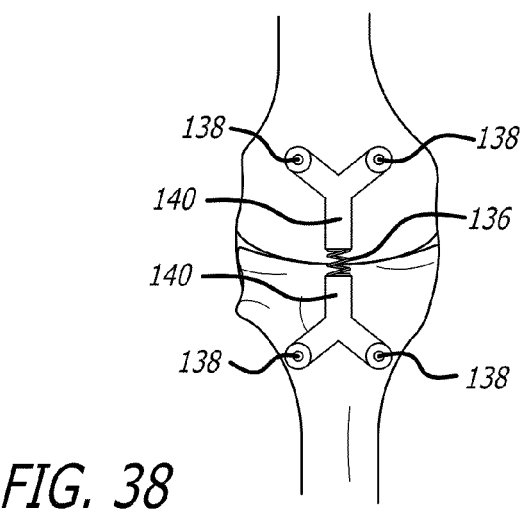
FIG. 38 is a front view, depicting yet another energy manipulation assembly including a central spring.

A spring assembly 126 having an overall helical configuration is depicted in FIG. 35. This spring assembly 126 further includes undulations 128 configured along the general helical framework as well as sections with varying thickness. In these ways, the spring assembly 126 can provide a varying energy absorption profile which matches the needs of a particular body joint, providing energy manipulation during certain pre-determined phases of articulation of members defining the joint. Similarly, a spring assembly can include spring portions divided by a center section including an elastomeric sleeve (not shown) which provides the device with desired energy manipulation characteristics. Moreover, the elastomeric sleeve can be used in affixing the assembly at the joint requiring treatment.

In related approaches (FIGS. 36-38), a mid-section of the bending spring assembly includes a spring member 136. Opposing ends of the assembly include bone anchors 138. As shown, the opposing ends can include one or more attachment structures or bone anchors 138. Configured between the bone anchor structure 138 and on opposing sides of the central spring 136 are load transfer beams 140. By way of a pivot configured between the bone anchors 140 and beams 140, the load transfer beams 140 can be made to rotate with respect to the bone anchors 138 and each other.

The bending spring assembly 142 depicted in FIG. 39 also includes a centrally located spring 144 configured between a pair of load transfer beams 146. As with previous embodiments, the spring 144 can assume various profiles characterized by varying widths and pitches to thereby provide the desired energy manipulation profile.

FIGS. 40 and 41 depict yet another embodiment of a bending spring assembly 148. In this embodiment, the energy is absorbed initially by an undulating beam 150. Upon near complete compression of the beam 150, curved portions thereof engage a centrally located stop member 152. The stop member 152 can be formed of rigid or non-rigid material depending on the energy manipulation that is desired in the application at hand.

Figure 42:
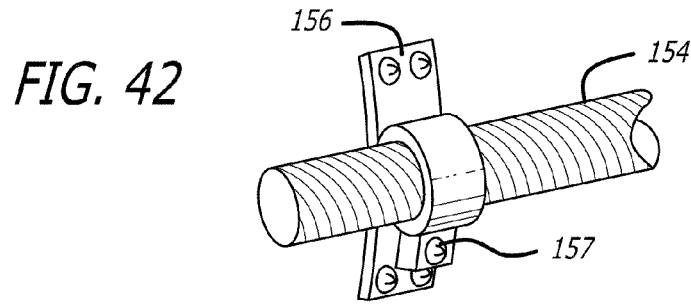
FIG. 42 is a perspective view, depicting adjustable attachment structure of a energy manipulation assembly.
Figure 43:
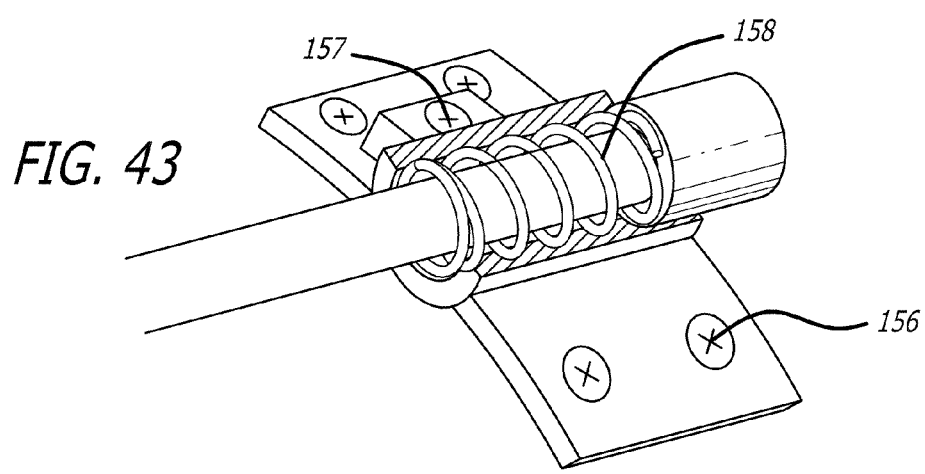
FIG. 43 is a partial cross-sectional view, depicting dampening structure of an attachment assembly.
Figure 44:
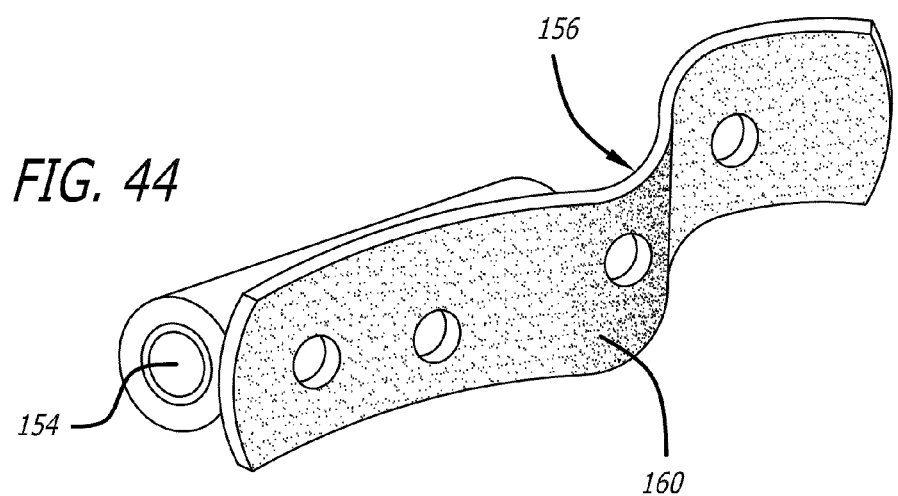
FIG. 44 is a perspective view, depicting another embodiment of an attachment structure of a load bearing member.
Figure 45:
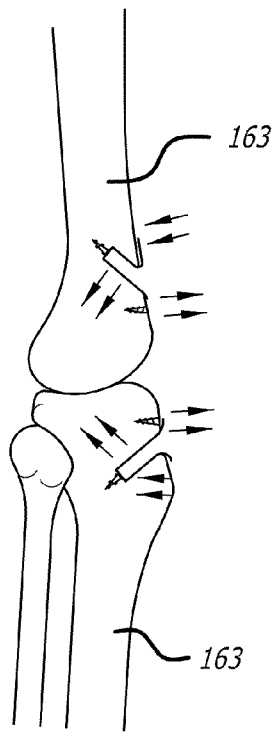
FIG. 45 is a cross-sectional view, depicting mounting structure formed in body anatomy.

Referring now to FIGS. 42-44, there are shown various details associated with attachment or mounting structure of a bending spring assembly, but the assembly can be employed across all contemplated approaches. A rod 154 connected to one such bend spring assembly (not shown) can be coupled to a bracket assembly 156 which is affixed to body anatomy of a patient. By way of an adjustment screw 156, the placement of the rod 154 can be adjusted with respect to the bracket assembly 156. It is contemplated that a needle screw (not shown) could be employed to accomplish the necessary adjustment percutaneously. The bracket assembly 156 can further or alternatively include a spring 158 (FIG. 43), the tension of which can be adjusted percutaneously to provide desired dampening or shock absorption at the ends of a bending spring assembly. Moreover, the bracket assembly 156 for these any of the disclosed embodiments can further include a textured surface 160 adapted for attachment to patient anatomy. Such texturing can surface irregularities or can come in the form of materials adapted for tissue in-growth.

Figure 46:
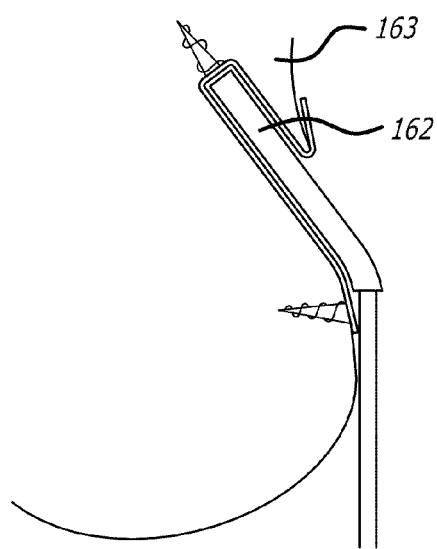
FIG. 46 is a partial cross-sectional view, depicting a energy manipulation assembly affixed to the body anatomy shown in FIG. 45.
Figure 47:
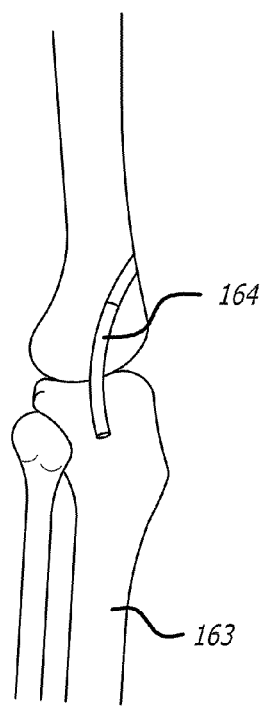
FIG. 47 is a cross-sectional view, depicting a load bearing assembly contained substantially entirely within body anatomy.
Figure 48:
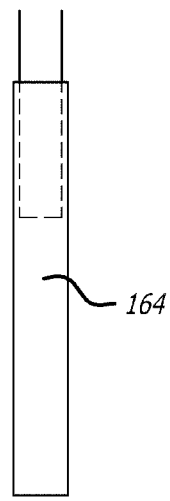
FIG. 48 is a side view, depicting an enlarged view of the energy manipulation assembly shown in FIG. 47.

Furthermore, the bending spring assemblies and for that matter each of the disclosed embodiments of energy manipulation assemblies, can be attached to body anatomy in various ways. As shown above, the assemblies of the present invention can be surface mounted upon anatomy by employing anchors. Also, mounting structure 162 can be inserted completely or partially within bones 163, for example, such as that in the manner depicted in FIGS. 21 and 22. Further anchoring of the assemblies can occur through a surface of the bone (See FIG. 46). Moreover, as shown in FIGS. 47 and 48, a energy manipulation assembly 164 can be placed substantially entirely with a bone 163, leaving a terminal end thereof to accomplish desired energy transfer and/or absorption.

Figure 49:
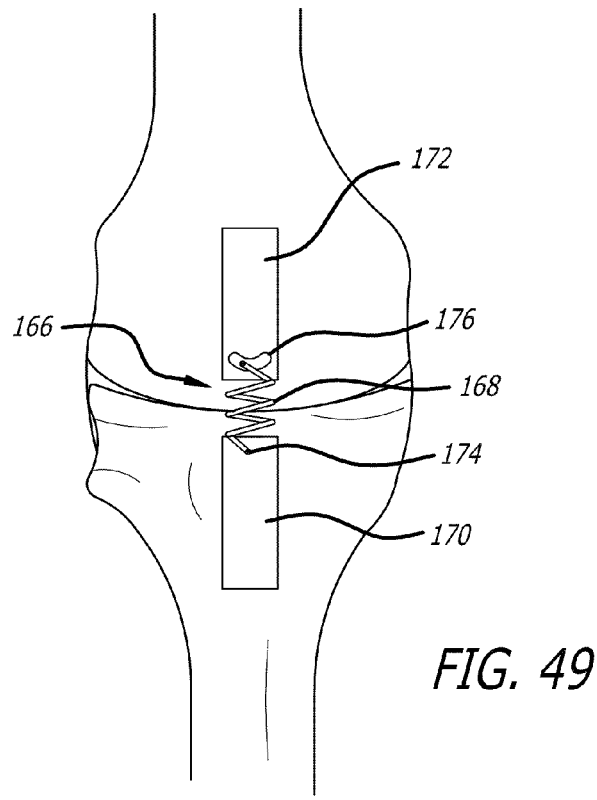
FIG. 49 is a side view, depicting a bending spring energy manipulation assembly including a slot for articulating movement.

The bending spring assemblies can embody rather complex structures. As shown in FIG. 49, one contemplated bend spring assembly 166 including a spring 168 can be attached to a pair of spaced attachment structures 170, 172. Such attachment structures 170, 172 can be directly connected to body anatomy or can be further attached to structure mounted on or within anatomy. The spring 168 includes one end which is fixed or rotatably connected to a first attachment structure 170 and a second end is constrained within a curved slot formed in the second attachment structure 172. Again, this unique design is contemplated to provide a body joint or other anatomy with a desired energy absorption and/or transfer profile which complements the unique articulation at the target tissue.

Figure 50:
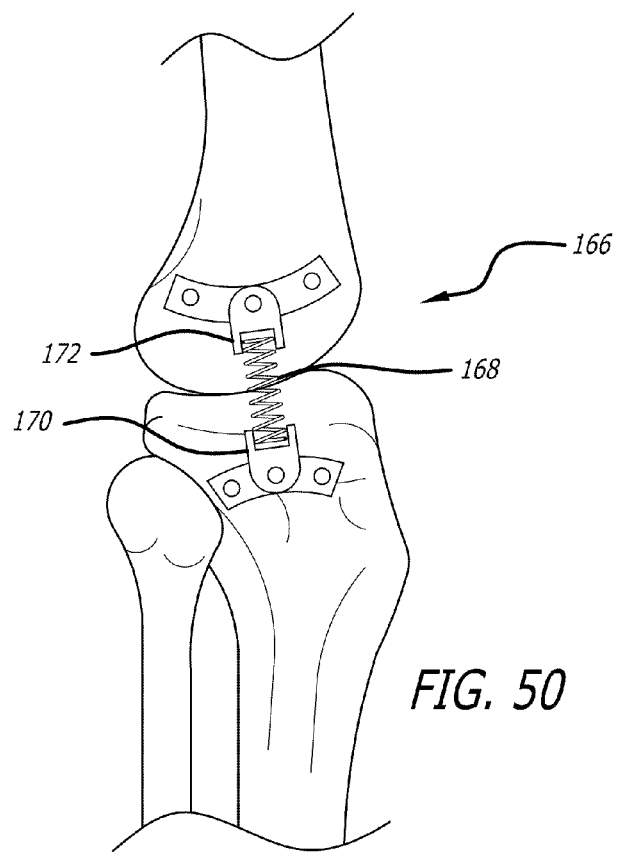
FIG. 50 is a side view, depicting another embodiment of a bending spring assembly including pivoting structure.
Figure 51:
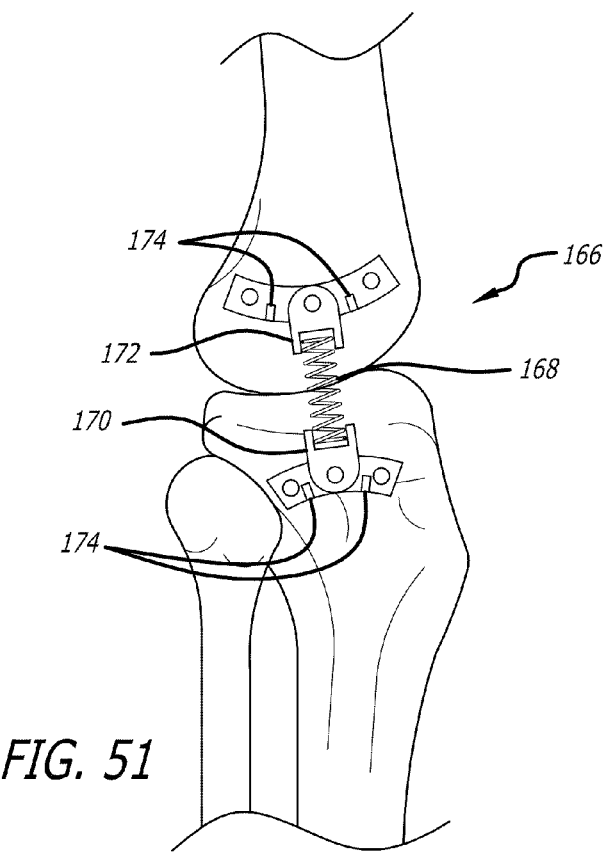
FIG. 51 is a side view, depicting yet a further embodiment of a bending spring assembly including pivoting structure.

The spring 168 of a bending spring assembly 166 can likewise be configured between one or more pivoting attachment structures 170, 172 (See FIGS. 50, 51). In a first approach, as shown in FIG. 50, one or both of the attachment structures 170, 172 are allowed to pivot about a pivot point. The pivoting action of the attachment structures 170, 172 of the device of FIG. 51 are constrained by stops 174.

Each of the previously and for that matter, hereinafter disclosed embodiments can incorporate or cooperate with sensing mechanisms adapted to provide loading information concerning the tissues being treated. Thus, it is contemplated that the various pressured sensing mechanisms available can be placed upon the devices of the present invention. Such sensors can be configured to provide information about the efficacy of the energy manipulating device of the present invention and whether adjustments are necessary. Similarly, sensors can be placed on anatomy to provide information regarding loads being placed on the tissues themselves.

Furthermore, it is contemplated that drugs can be delivered to the interventional site targeted for energy manipulation. In this regard, the entirety of the subject matter disclosed in U.S. Publication No. 2007/0053963 is hereby incorporated by reference.

In other aspects, the present invention is embodied in a cam engagement assembly for energy manipulation. In this approach, the cam engagement assembly employs contacting elements, at least one of which has an eccentric contracting surface. The degree, duration and instance of elemental contact is controlled by the profile of the cam element or elements. Increased contact stress is contemplated between device elements when the body anatomy members are in extension. During flexion, the cam profile can be configured to ensure little or no engagement. The assembly can include a spring assembly that can be made to be adjusted, or exchanged, to tune the amount of energy absorption across anatomy.

Moreover, the surface engagement of the device can be created through multiple methods and can include such structure as wear-resistant bearing surfaces, ball bearings at a surface engagement site or a geared engagement. The mounting features of the device can be contained in separate mounting elements or incorporated into anatomy spring elements. The mounting design can further accommodate complex motion of a joint as it transitions from extension to flexion by allowing for rotation and pivoting, or through the use of compressible materials.

Various approaches to cam related energy manipulation are depicted in FIGS. 52-61. In a first embodiment (FIGS. 52 and 53), curved load bearing surfaces 202 are configured to rotate with respect to each other. The load bearing surfaces 202 are connected to attachment structure 204, 206 which in turn are affixed to body anatomy such as bones forming a joint. The connections between the load bearing surfaces 202 and attachment structures 204, 206 or between the attachment structures 204, 206 and the bone can be spring loaded or otherwise be comprised of flexible or elastic materials. As the body anatomy transitions between extension (FIG. 28) and flexion (FIG. 29), the energy bearing surfaces 202 move between varying degrees of engagement. In one aspect, it is contemplated that the greatest off-loading and energy manipulation occurs between loading members 202 when the body anatomy is in its extension configuration. The varying degrees of engagement are pre-selected to absorb energy between body members with the aim of reducing or eliminating pain. In this way, unique paths of motion can be preserved during an attempt at absorbing energy.

Another embodiment of a cam engagement assembly is shown in FIG. 54. In this approach, a center load bearing, joint section 208 is configured between a pair of spaced attachment brackets 210. Post members 212 provide rotation points to define an articulating engagement assembly. Various connecting points 214 can be further provided along the attachment bracket 210 to receive the post members 212 to thereby provide a means to readjust the assembly to fit a patient's needs. It is further contemplated that gearing structure (gears or gears and a rack) can be implemented into this embodiment to provide desired control between moving parts.

Figure 55:
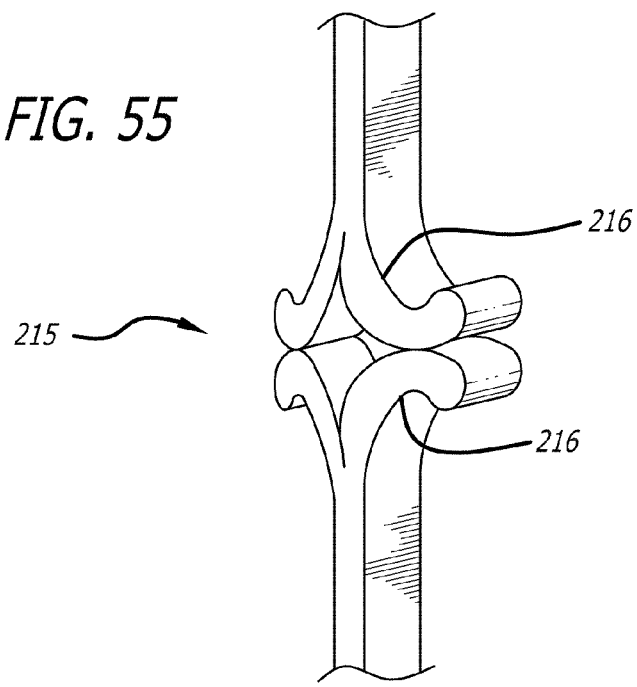
FIG. 55 is a perspective view, depicting a energy manipulation assembly including multiple camming surfaces.
Figure 56:
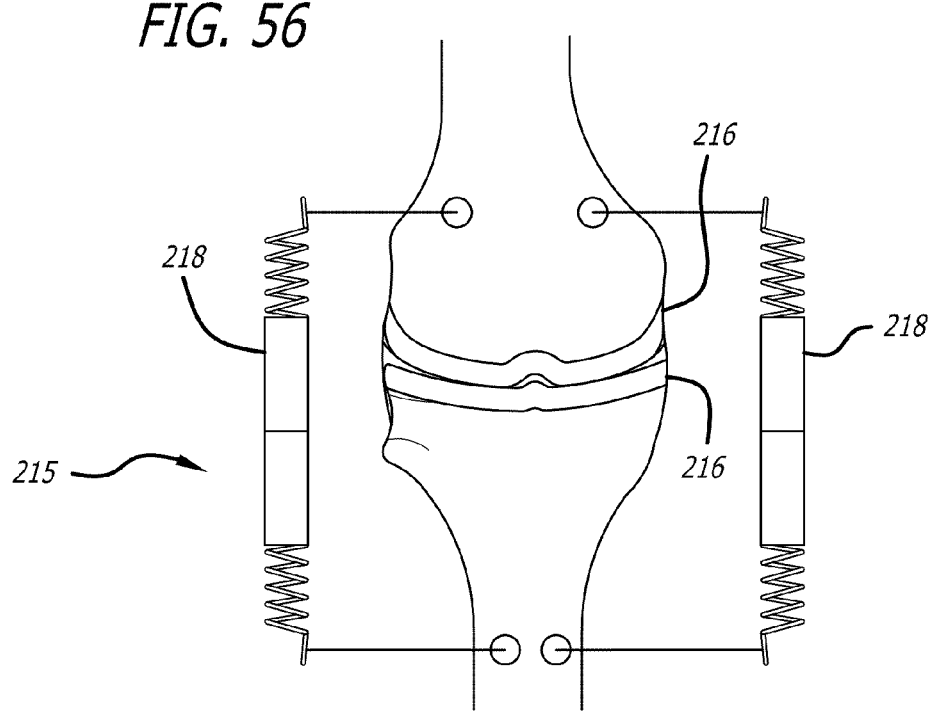
FIG. 56 is a front view, depicting a energy manipulation assembly including camming surfaces and spring biasing structure.

Another embodiment of a cam engagement assembly 215 of the present invention is depicted in FIGS. 55 and 56. In this approach, camming surfaces 216 are adapted to fit the natural contour of the body anatomy. In one aspect, the camming surfaces 216 are provided along substantially an entire range of surfaces of natural tissue which may come into contact. This structure is supplemented with a energy absorbing assembly 218 comprising springs or other structure for absorbing energy from areas of contact between the camming surfaces 216. Such an assembly 215 is affixed at a joint or other body anatomy employing approaches described herein.

Figure 57:
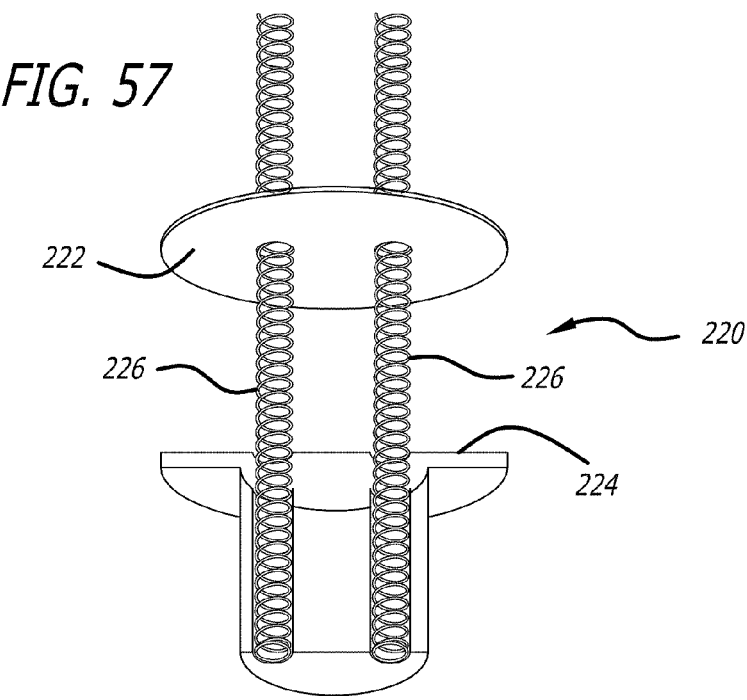
FIG. 57 is a perspective view, depicting yet another embodiment of a energy manipulation assembly including multiple camming surfaces.

Turning to FIG. 57, there is shown a cam engagement assembly 220 including a first concave camming surface 222 and a second convex camming surface 224. These surfaces are biased apart by a pair of springs 226 arranged in a parallel fashion. Each of the camming surfaces 222, 224 include cavities for receiving a portion of the springs 226. The springs 226 act as a energy absorbing structure and in combination with the convex and concave surfaces 222, 224 complements the action of the body parts to which the assembly is attached.

Figure 58:
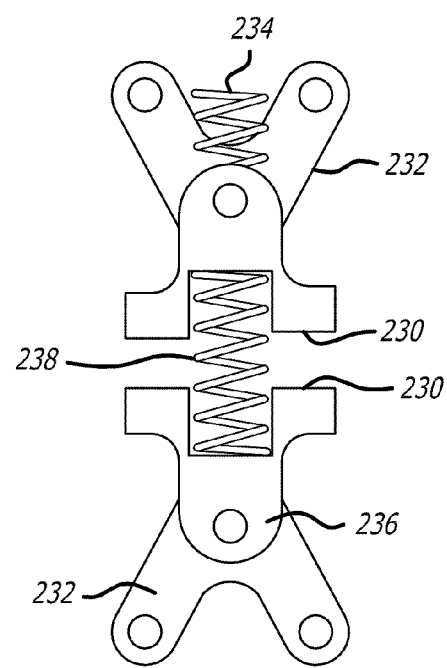
FIG. 58 is a front view, depicting a energy manipulation assembly including camming surfaces and pivoting substructure.

A similar combination of elements is disclosed in FIG. 58. Here, the camming surface assemblies 230 are at least at one end attached in a spring loaded arrangement 233 to brackets 232. A second camming surface 230 can be connected in a manner to allow pivoting between the camming surface 230 assembly and bracket 232 such as by providing a slotted connector 236. The brackets 232 are in turn affixed to body anatomy. Configured between the camming surface assemblies 230 is a load bearing spring assembly 238 which at opposing ends engages receiving holes formed in the camming surface assemblies 230.

Figure 59:
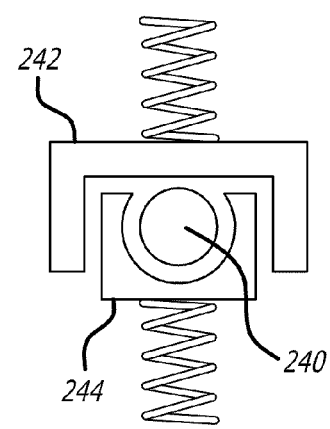
FIG. 59 is a partial cross-sectional view, depicting a ball bearing in combination with camming surfaces.
Figure 60:
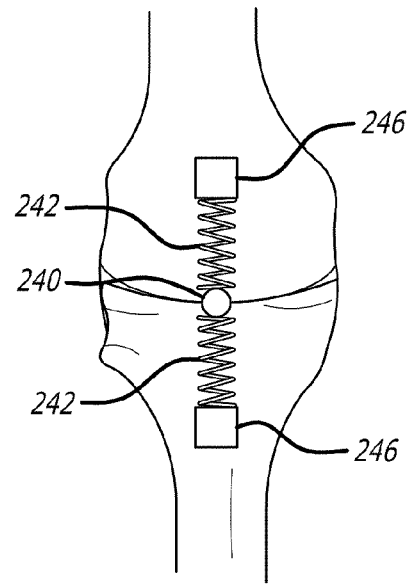
FIG. 60 is a side view, depicting a energy manipulation assembly employing a ball-like camming surface.
Figure 61:
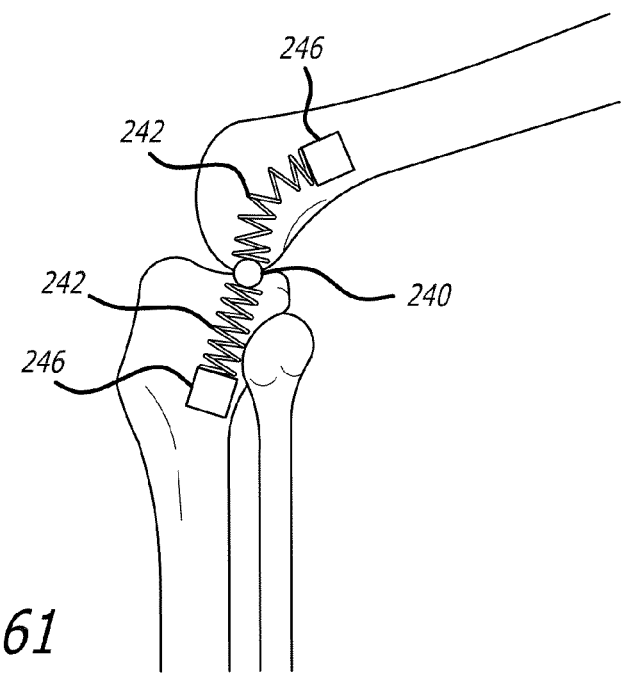
FIG. 61 is a side view, depicting the assembly of FIG. 60 in relation to articulated body members.

As shown in FIG. 59, a ball bearing 240 can be strategically placed between camming surfaces 242 of a cam engagement assembly for the purpose of aiding the relative motion between the structures. Such an approach can be further incorporated into any of the disclosed assemblies. In one particular embodiment (FIGS. 60 and 61), a ball bearing 240 is placed between the anatomy of articulating members of a patient. Alternatively, a disc can be employed in like fashion. In either approach, the ball bearing structure 240 is supported by energy absorbing springs 242 which are in turn attached to attachment structure 246 mounted to patient anatomy.

A further aspect of the present invention is embodied in a segmented support assembly. Generally, this approach employs multiple elements that align and mate to provide column support as desired, such as during extension of loading parts. Thus, in one aspect, adjacent elements forming a segmented support assembly can be constrained by an adjacent element in a variable fashion to accommodate the complex motion of articulating members. The amount of energy manipulation is adjusted by mounting or attaching components via spring or dampening assemblies.

Figure 62:
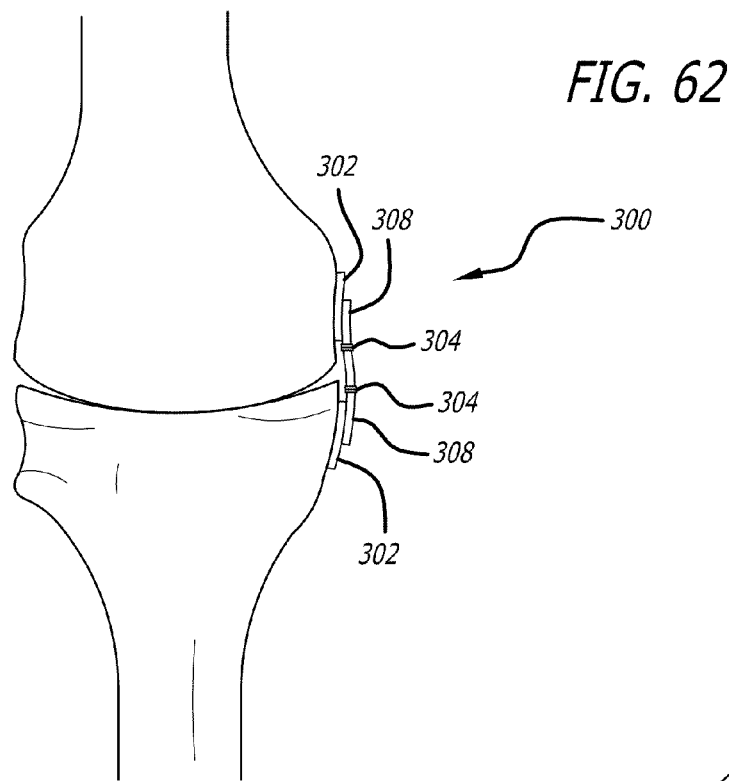
FIG. 62 is a front view, depicting a energy manipulation assembly incorporating segmented support substructure.
Figure 63:
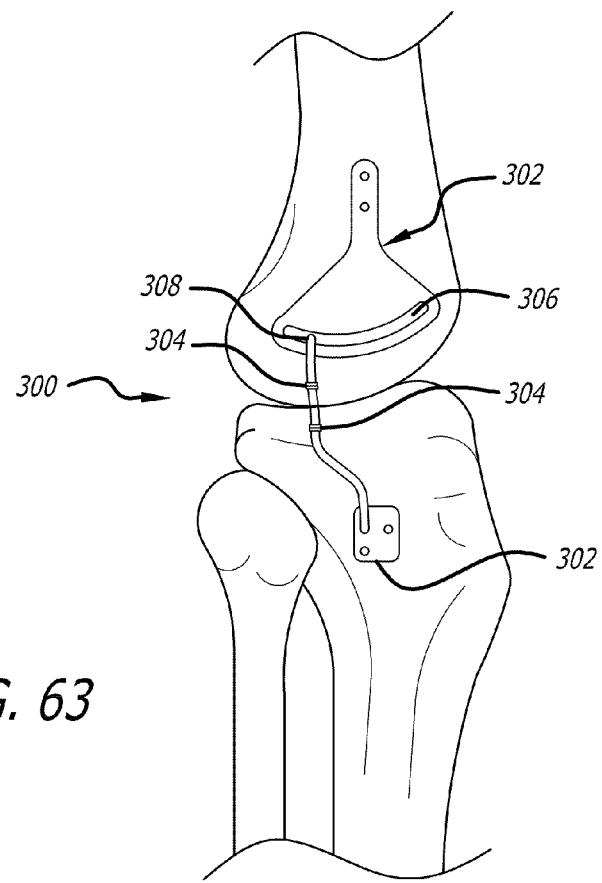
FIG. 63 is a side view, depicting the assembly shown in FIG. 62 further incorporating a slotted engagement arrangement.

With reference to FIGS. 62 and 63, there is shown one embodiment of a segmented support assembly 300. Fixation base components 302 are provided to attach the assembly to patient anatomy. Medially positioned pivot points 304 in combination with adjustable spacers 306 define a segmented load bearing member and provide desired off-loading as well as multi-dimensional flexibility permitting the patient anatomy to articulate freely. Being adjustable, the spacers 306 function to facilitate alignment. In one particular aspect, at least one fixation component 302 can include a slotted receiving trough 306 sized to receive one terminal end 308 of the segmented load bearing member, the terminal end 308 slideably engaging the slot.

Figure 64:
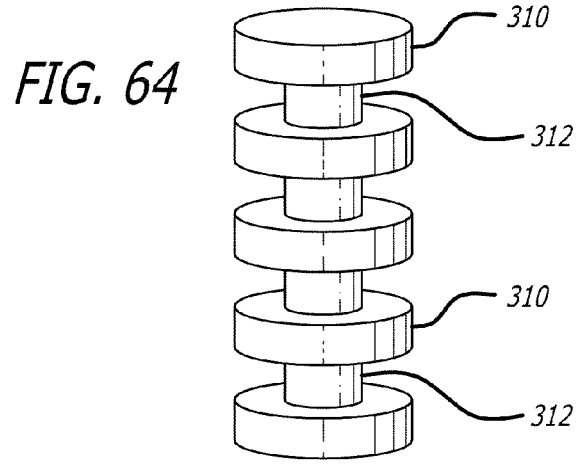
FIG. 64 is a perspective view, depicting another embodiment of a segmented support subassembly.
Figure 65:
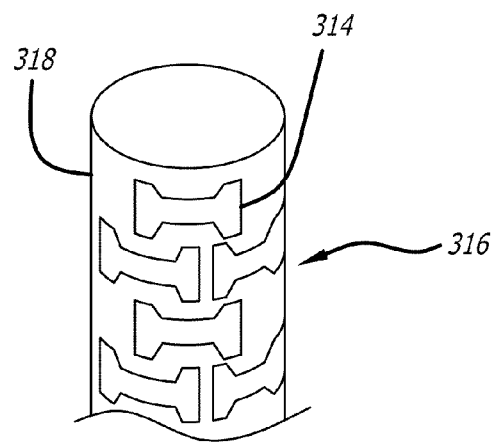
FIG. 65 is a perspective view, depicting yet another embodiment of a segmented support subassembly.
Figure 66:
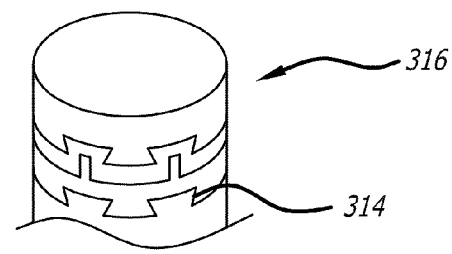
FIG. 66 is a perspective view, depicting yet still another segmented support subassembly.
Figure 67:
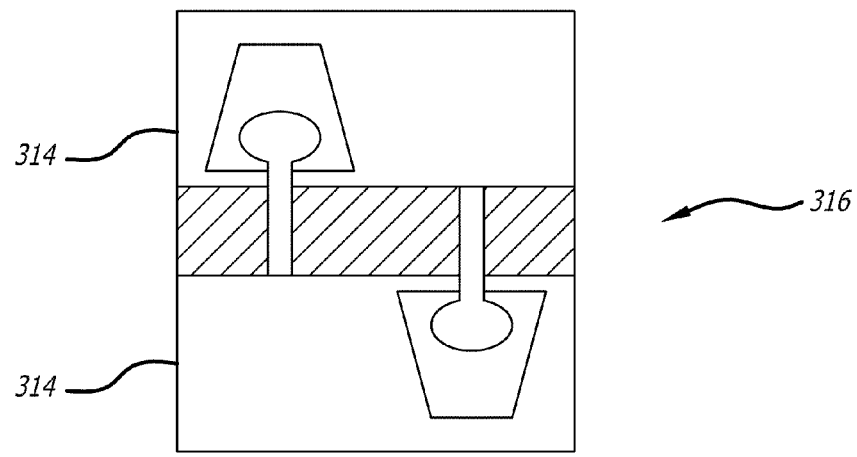
FIG. 67 is a side view, depicting members forming a segmented support subassembly.
Figure 68:
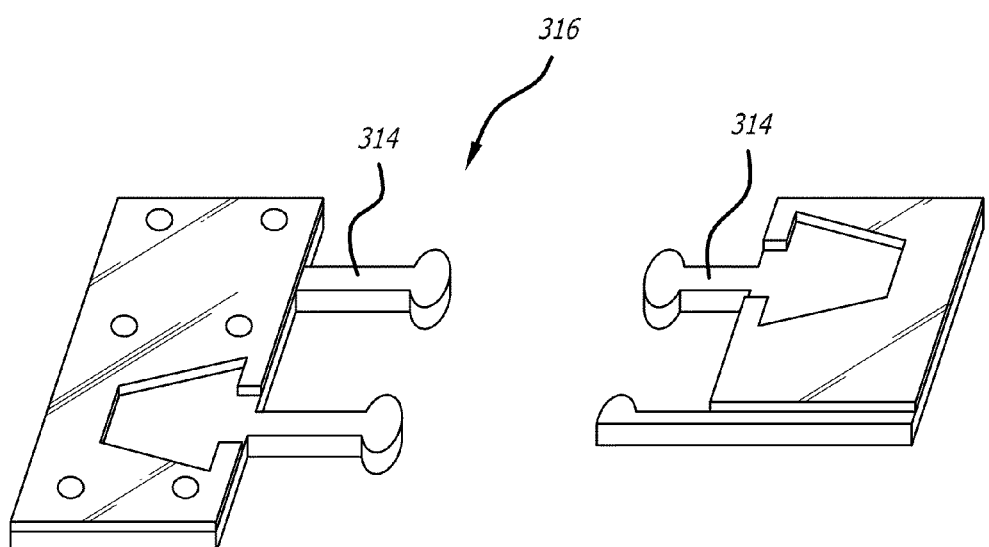
FIG. 68 is a perspective view, depicting disengaged members of a segmented support subassembly.
Figure 69:
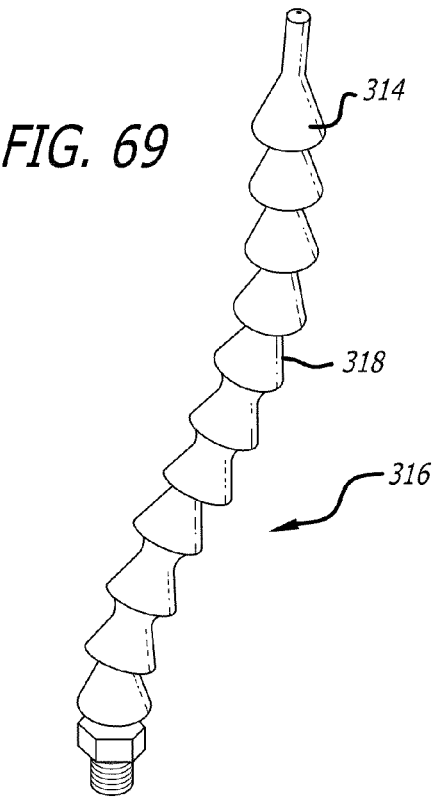
FIG. 69 is a perspective view, depicting a segmented support assembly encased in an outer sheath.
Figure 70:
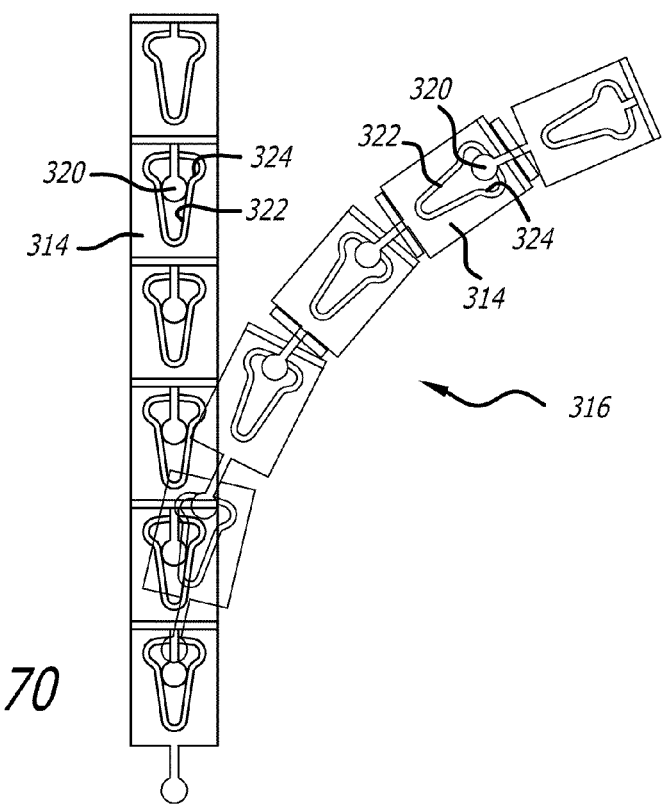
FIG. 70 is a perspective view, depicting both a longitudinally arranged segmented support assembly and its configuration upon bending.

The segmented load bearing member can assume various shapes and forms. These approaches incorporate multiple, mating elements which provide columnar support while facilitating multi-dimensional movement. Such approaches are shown in FIGS. 64-69. As depicted in FIG. 64, disc-like members 310 are connected in a series via interconnecting structures 312 contemplated to permit three-dimensional translation between adjacently arranged discs 310. While three-dimensional motion is contemplated, the degree of motion is constrained by the members defining the segmented load bearing member. Accordingly, there can be limited axial compression of the members so that there is a desired amount of columnar support. Likewise, lateral pivoting of the members is limited by the geometry of the adjacent discs. The lateral pivoting can be selected to permit and complement the unique articulation of a particular patient's anatomy.

The structure defining a segmented load bearing member can assume relatively complex geometry. That is, various embodiments of interlocking links 314 can form a segmented load bearing member 316 (See FIGS. 65-70). Such links 314 can be held within a sheath 318 (FIGS. 65 and 69) or can be locked together to permit articulation without the need for an outer sheath (FIGS. 66-68 and 70). In a further aspect (See FIG. 70 for example), certain designs of the links 314 can include a projection 320, a number of which are received within a variable shaped slot 322 of an adjacent link. The variable staged slot 322 can further include a narrower section 324 which is sized and shaped to engage the projection 320 in a manner to both absorb loads as well as constrain articulating motion.

Figure 71:
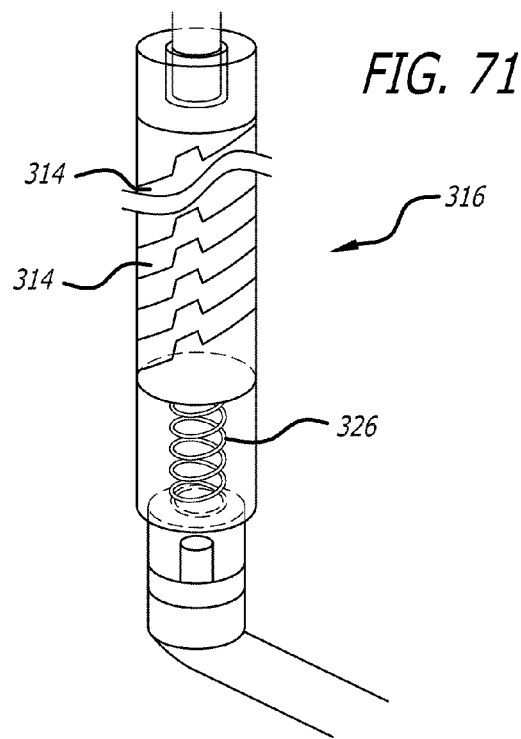
FIG. 71 is a perspective view, depicting a segmented support assembly including variable interlocking links in combination with spring assemblies.
Figure 72:
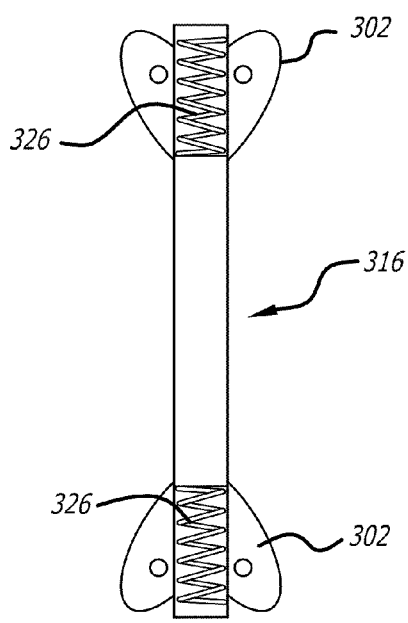
FIG. 72 is a side view, depicting yet another embodiment of a segmented energy manipulation assembly.
Figure 73:
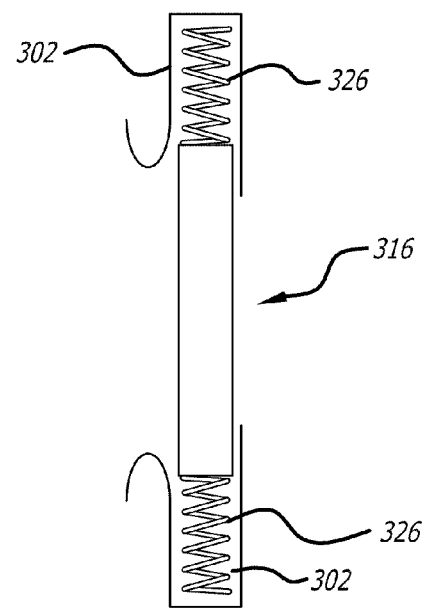
FIG. 73 is a side view, depicting still yet another embodiment of a segmented energy manipulation assembly.
Figure 74:
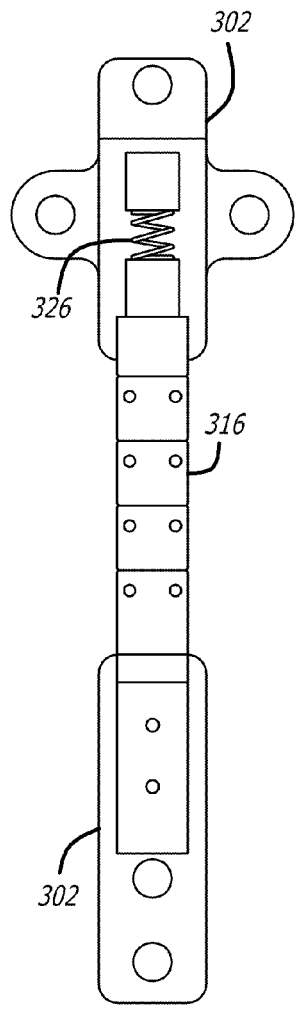
FIG. 74 is a partial cross-sectional side view, depicting still yet another segmented support assembly for a energy manipulation assembly.
Figure 75:
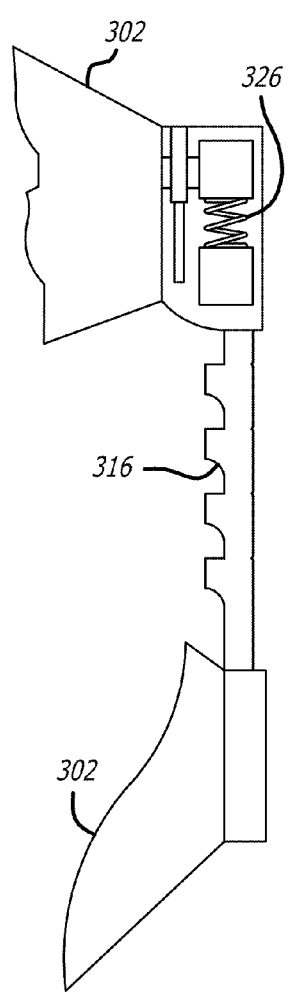
FIG. 75 is a partial cross-sectional view, depicting the assembly of FIG. 74.
Figure 76:
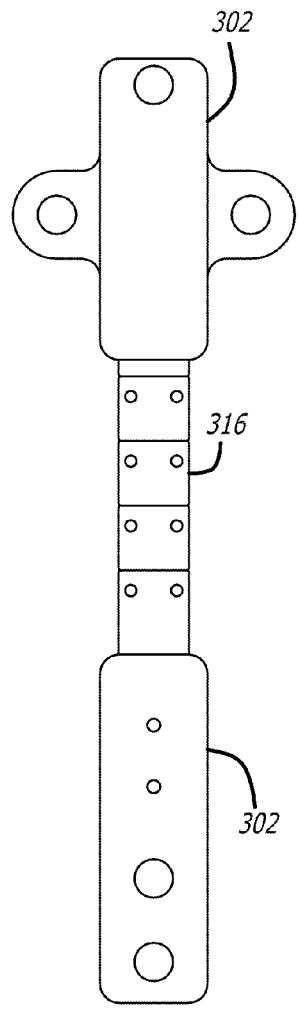
FIG. 76 is a bottom view, depicting the assembly shown in FIG. 74.

Furthermore, as shown in FIG. 71, the links 314 of a segmented section of a load bearing member 316 can embody variably shaped links 314. That is, the geometry of the links 314 can vary along a length of a load bearing member 316 to thereby provide differing articulation at various points. Moreover, the assembly can incorporate one or more springs 326 designed to facilitate desired energy absorption and/or dampening.

Other examples of assemblies including segmented load sharing linkages in combination with spring assemblies are shown in FIGS. 72-76. In each of these embodiments, springs 326 can be placed at one or more ends of the segmented load bearing members 316. It may be convenient to configure the springs 320 within attachment structures 302 employed to anchor the assembly to body anatomy. Springs 320 can also be placed along other portions of the assembly to achieve desired effects.

Figure 77:
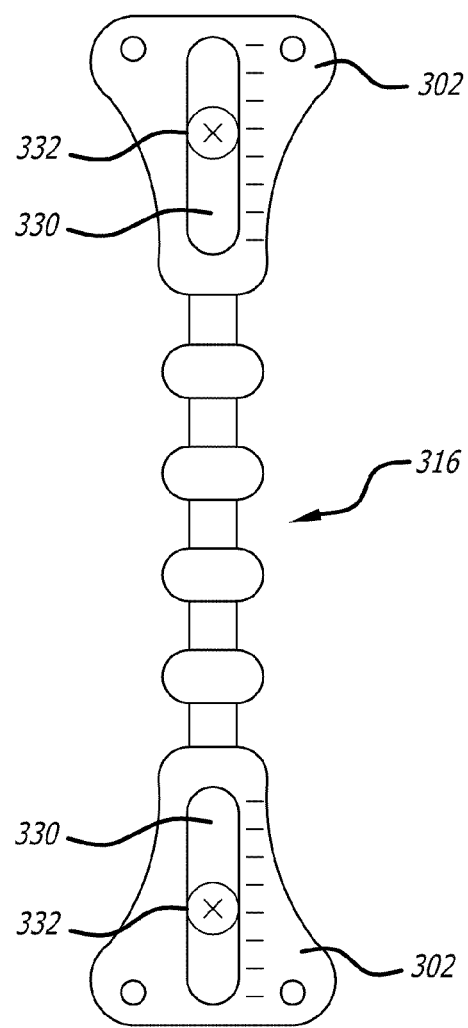
FIG. 77 is a side view, depicting a segmented energy manipulation assembly including slotted attachment structure.
Figure 78:
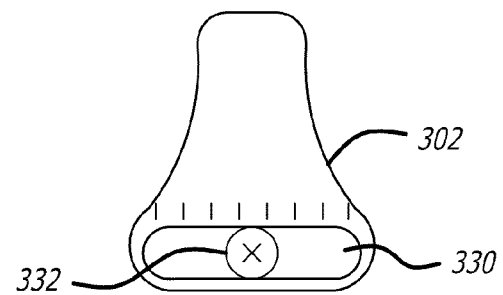
FIG. 78 is a side view, depicting a modification to the assembly shown in FIG. 77.
Figure 79:
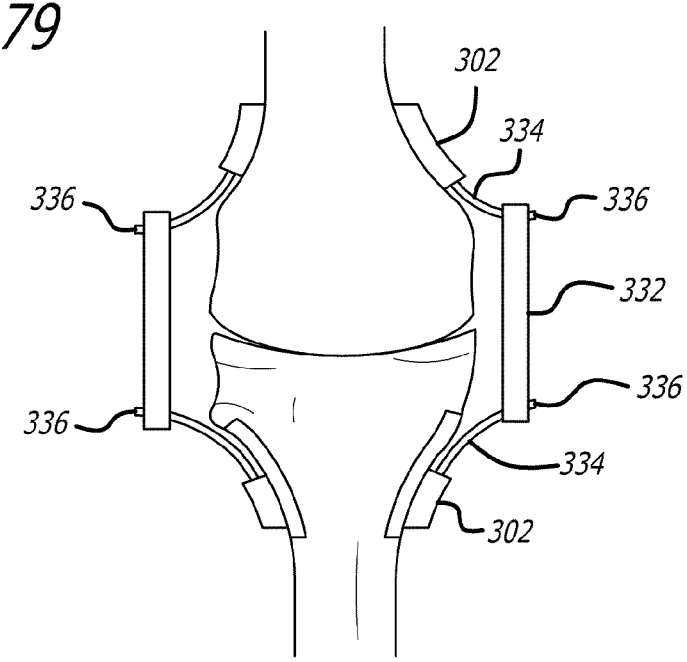
FIG. 79 is a front view, depicting a energy manipulation assembly incorporating segmented and articulating structure.
Figure 80:
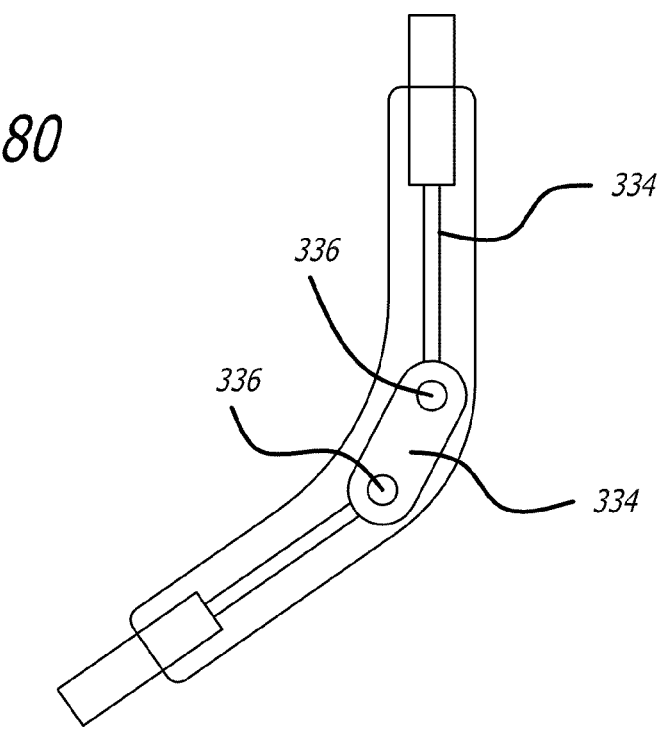
FIG. 80 is a side view, depicting sheathing of members of a energy manipulation assembly.
Figure 81:
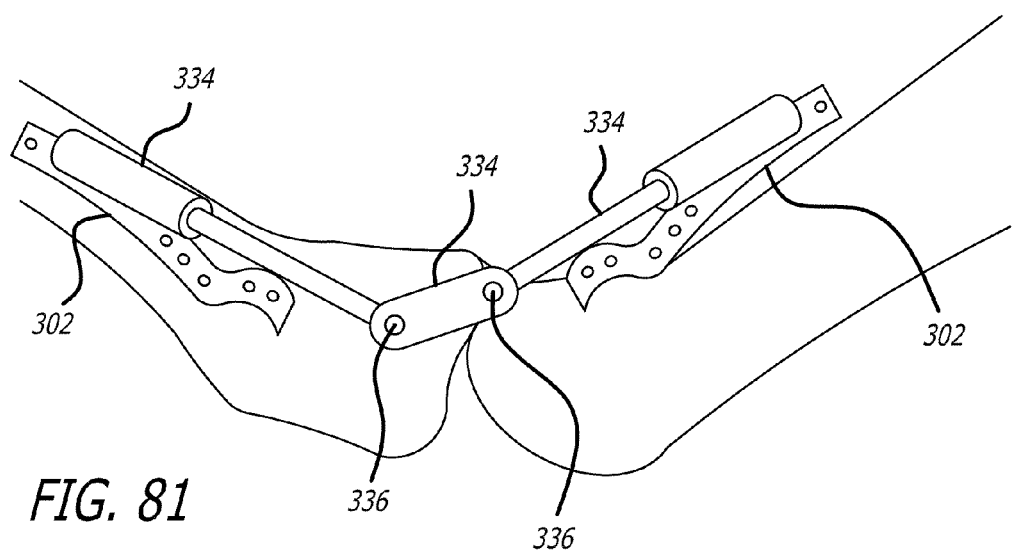
FIG. 81 is a perspective view, depicting further aspects of a segmented support assembly of the present invention.
Figure 82:
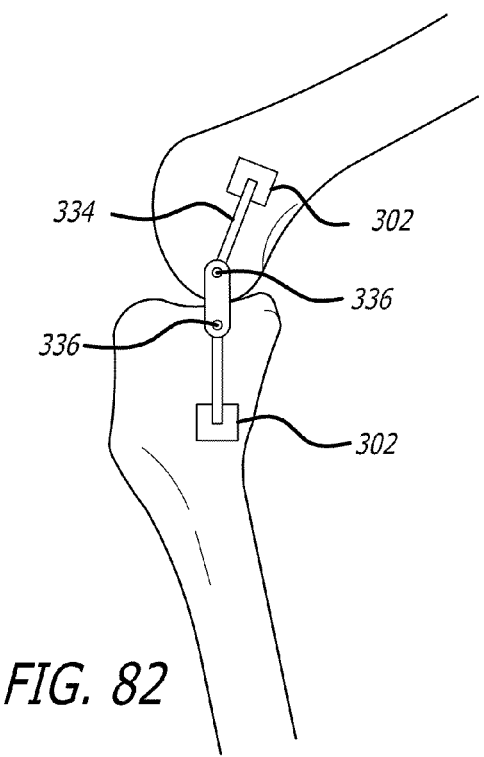
FIG. 82 is a side view, depicting yet further aspects of segmented support assemblies of the present invention.
Figure 83:
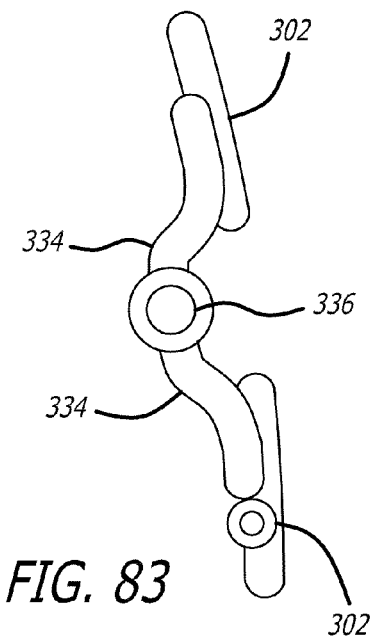
FIG. 83 is a side view, depicting a energy manipulation assembly including articulating and segmented structure.

In yet another embodiment (FIGS. 77 and 78), the assembly is provided with slotted structure 330 rather than springs. The slotted structure 330 can be configured within the attachment structure 302 and be both generally vertical (FIG. 77) or generally horizontal (FIG. 78). An adjustment screw 332 or similar structure can further be provided to permit adjustment of the attachment structure relative to patient anatomy and to the segmented load bearing structure 316.

Other of segmented support assemblies of the present invention employ articulating linkages rather than interlocking links to provide desired results (See FIGS. 79-83). The various contemplated articulate linkages 334 can have a myriad of shapes and sizes and can include one or more points of articulation 336. Opposed ends of the linkages 334 are affixed to body anatomy in varying ways as well. As with all of the disclosed embodiments, mounting structure of one approach can be substituted for another and thus, the load bearing assemblies can be surface mounted to anatomy or partially buried therewithin. Moreover, the linkages can be sheathed (See FIG. 80) or can lack sheathing.

In yet another specific approach, the present invention employs piston support to accomplish desired load manipulation. In general, these embodiments include an axially mobile member which translates in a defined linear path. A compressible spring can be included to facilitate energy absorption and transfer and the assembly can further include structure permitting articulation between the piston subassembly and the body anatomy.

Figure 84:
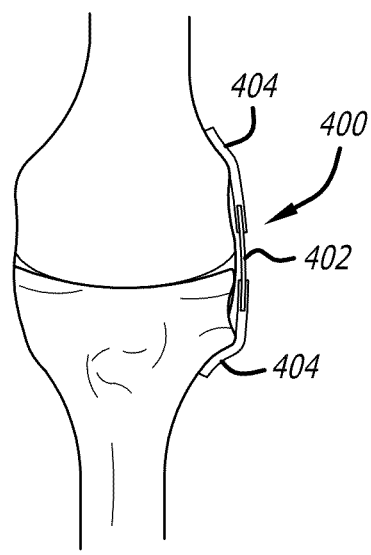
FIG. 84 is a front view, depicting a energy manipulation assembly incorporating piston support.
Figure 85:
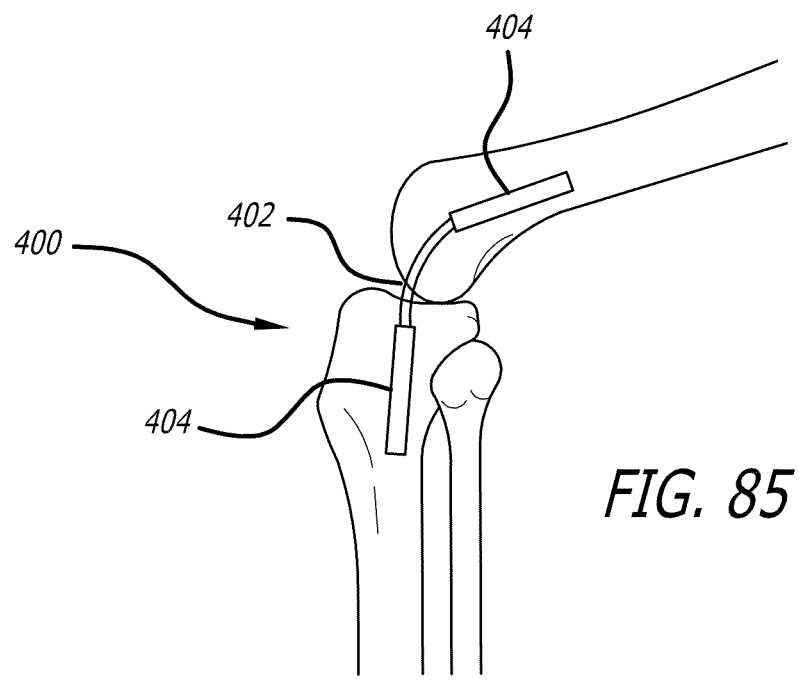
FIG. 85 is a side view, depicting the assembly of FIG. 84 after articulation of body members.

A simplified approach involving a piston support, load manipulation assembly 400 is depicted in FIGS. 84 and 85. In this embodiment, the piston member 402 is highly laterally flexible but also sufficiently longitudinally rigid to thereby both bend with the articulation of body members as well as absorb compression forces when the body members are in extension. One or more cylinders 404 are configured to accept longitudinal translation of the piston 402.

Figure 86:
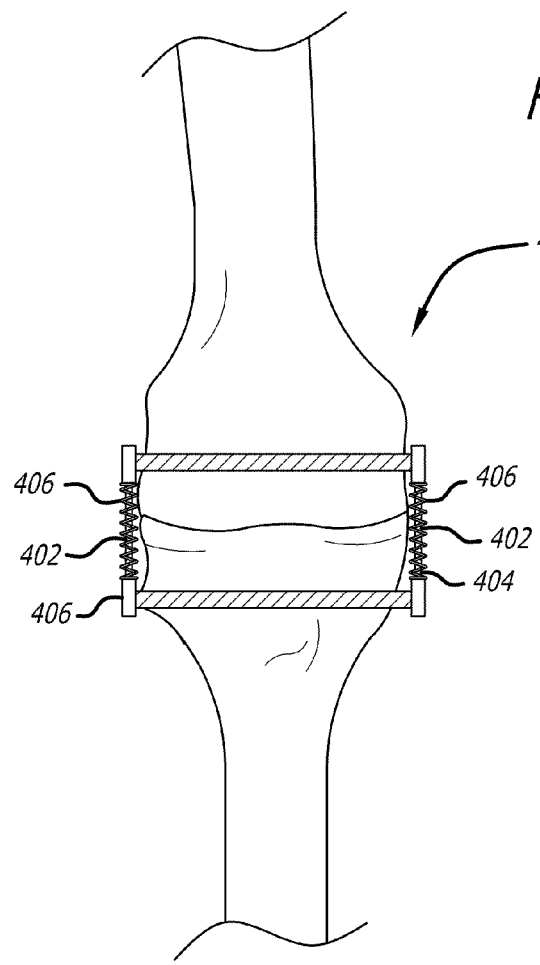
FIG. 86 is a front view, depicting another embodiment of a energy manipulation assembly incorporating piston support.
Figure 87:
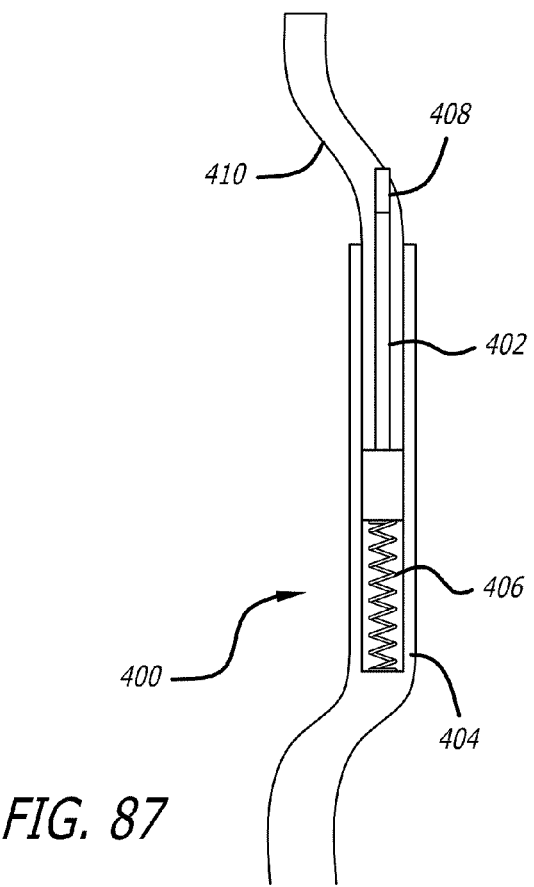
FIG. 87 is a cross-sectional view, depicting substructure of the assembly shown in FIG. 86.

A piston support assembly 400 can further include springs 406 to aid in the load manipulation being sought (See FIGS. 86 and 87). Such springs 406 can be placed within an attachment cylinder 404 (FIG. 87) or can be additionally or alternatively placed about the piston assembly 402. Moreover, the piston assembly 402 can assume a complex geometry which includes both pivot points 408 and/or curvilinear portions 410. As in all of the disclosed embodiments, the structure can be affixed to body anatomy so that it spans a joint between articulating members.

Figure 88:
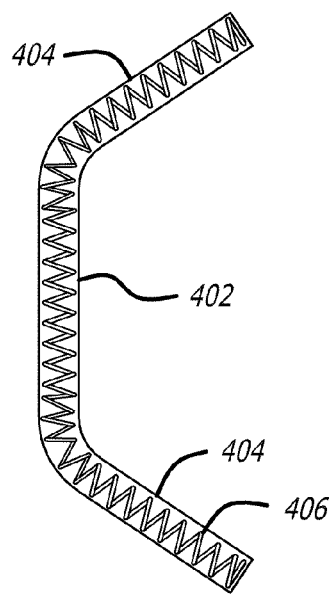
FIG. 88 is a partial cross-sectional view, depicting another embodiment of a piston support subassembly.
Figure 89:
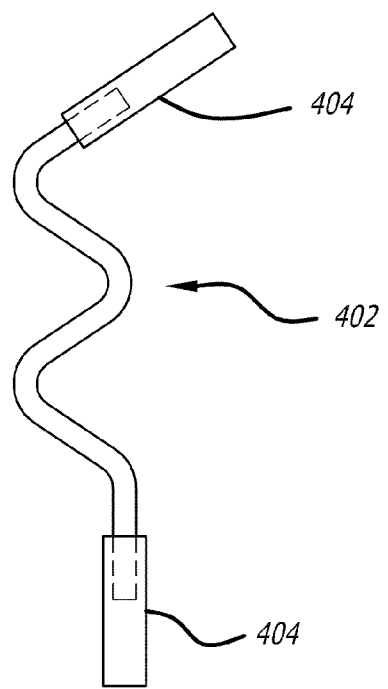
FIG. 89 is a partial cross-sectional view, depicting yet another embodiment of a piston support subassembly.

Further embodiments of piston-based load bearing members are disclosed in FIGS. 88-94. FIG. 88 discloses an arrangement when a spring 402 spans the length of the piston member 402 and within spaced cylinders 404. FIG. 89 employs a piston member 402 which additionally includes bending spring structures for energy manipulation. FIGS. 90 and 91 depict a piston assembly 402 including a knurled outer surface and is further contemplated to include means for adjusting the strength of its loading capabilities by rotating the piston with respect to the cylinder. FIG. 92 shows an assembly which includes a spring 406 configured about the piston 402 having a stepped profile and between a cylinder 404 and a pair of stops 412. This assembly is also contemplated to be adjustable between high and low spring tensions.

A piston support based assembly 400 can also include a plurality of telescoping members 414 arranged longitudinally. Thus, certain of the circumferentially arranged telescoping members act both as pistons and cylinders for adjacent structure. By varying the energy which adjacent telescopic members 414 can bear, a desired energy absorbing profile can be provided by the structure to thereby absorb energy in a desired sequence.

As previously described, the energy absorbing assemblies of the present invention can be surface mounted upon anatomy or can be inserted completely or partially within the target tissue. As shown in FIGS. 95 and 96, a piston based, energy manipulation assembly 400 having one or more cylinders 404 receiving a piston 402 can be substantially completely implanted within a member defining a target tissue. The portions extending out from a surface of the tissue provide the energy absorbing characteristics needed for a particular application. The assemblies 400 can also be configured to span articulating body members and include a portion of the cylinder 404 being buried within body tissue as shown in FIGS. 97 and 98.

Figure 99:
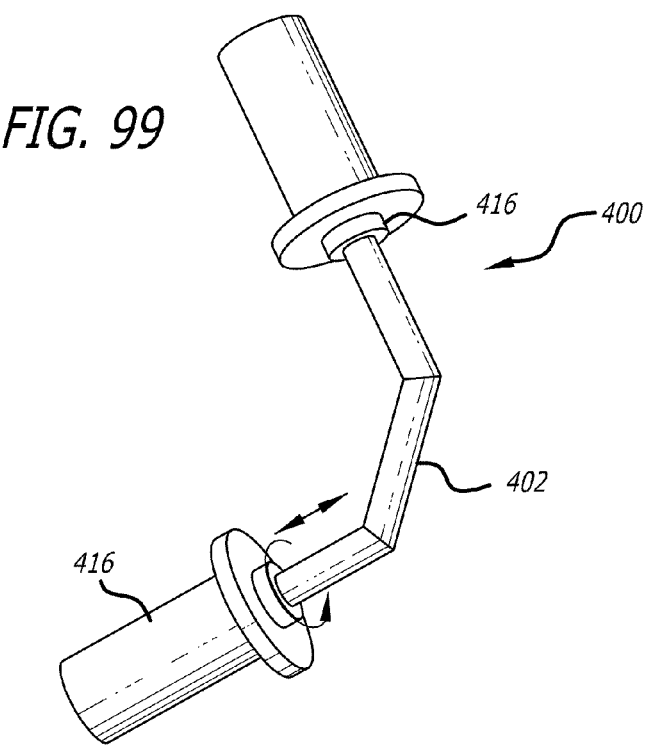
FIG. 99 is a perspective view, depicting a load bearing member of a energy manipulation assembly including piston support and incorporating rotational substructure.

Structure which is believed to be particularly suited for the situations depicted in FIGS. 97 and 98 is shown in FIG. 99. Here, the energy absorbing assembly 402 includes a mid-section characterized by a piston having bending spring qualities and further includes collars 416 which are configured to rotate with respect to the piston. The collars 416 are also sized and shaped to be placed into a reciprocating motion with a cylinder.

Figure 100:
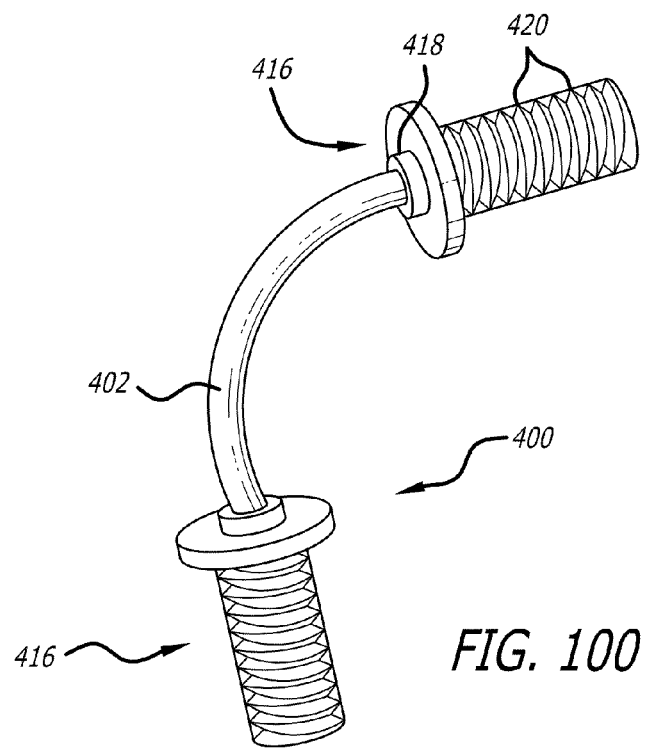
FIG. 100 is a perspective view, depicting adjustment substructure of a energy manipulation assembly for the present invention.
Figure 101:
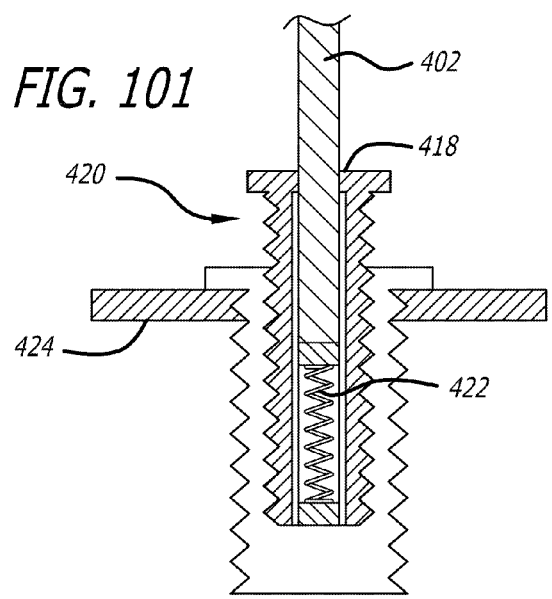
FIG. 101 is a cross-sectional view, depicting further aspects of the assembly depicted in FIG. 100.

With reference to FIGS. 100 and 101, the collars 416 can further include a washer and bearing arrangement which permits rotation of the collar 416 and the piston or end 402. Further, a screw assembly can be employed to connect the mid-section of the piston assembly with the collar 416. A spring 422 can be further provided within the collar 416 (See FIG. 101) to accept loads. The assembly 400 is then threaded within an attachment structure 424 and affixed to or within body tissue.

Figure 102:
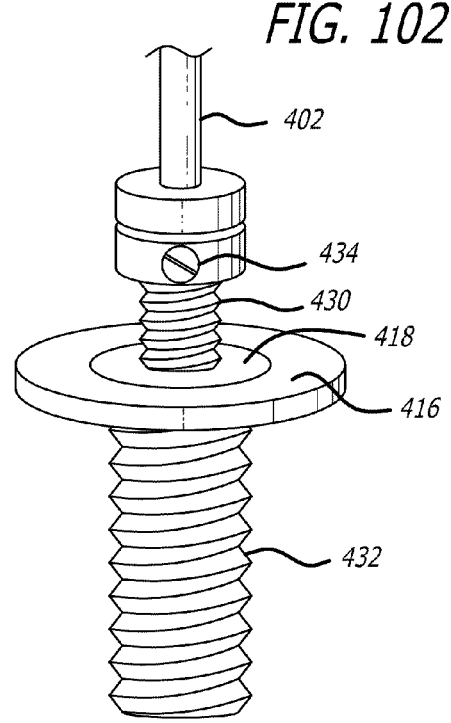
FIG. 102 is a perspective view, depicting further aspects which can be incorporated into the assembly depicted in FIG. 100.
Figure 103:
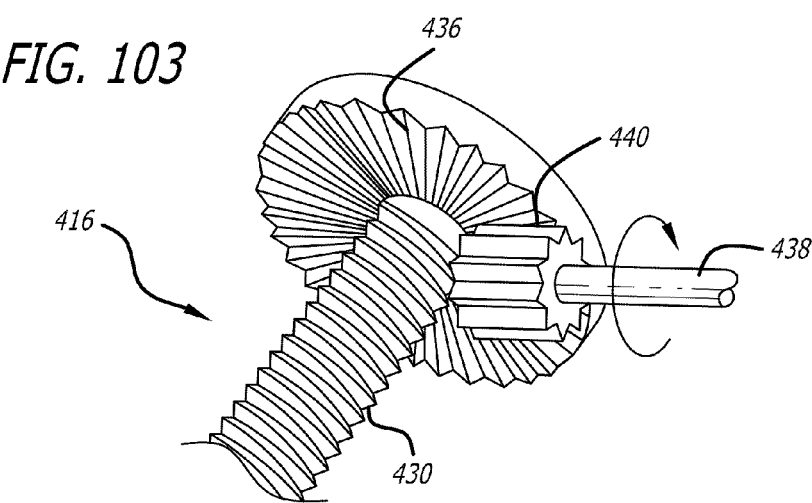
FIG. 103 is a perspective view, depicting adjustment structure of a energy manipulation assembly of the present invention.

In a further modification to the approach in FIGS. 100 and 101, it is contemplated that inner 430 and outer members 432 of the collar assembly 416 can be adjustable postimplant. In a first embodiment (FIG. 102), the collar assembly 416 can include a percutaneously accessible adjustment screw 434 which controls the relative positions between the inner and outer members 430, 432. One or more of the inner and outer housings 430, 432 can alternatively be equipped with a gear surface 436 that is accessible by a percutaneous gear shaft tool 438 (FIG. 103). The tool 438 includes a terminal end 440 configured with a gear surface complementary to that of the gear surface formed on the collar assembly 416. In this way, tension as well as spacing of the components of a energy manipulation assembly can be altered or corrected as needed.

A sheathed energy manipulation assembly 440 incorporating various aspects of the present invention is shown in FIGS. 104-108. In this embodiment, ends of the assembly are reciprocally mounted within body tissue. The length of the device is encased in a sheath 442. It is to be recognized that various of the contemplated energy manipulation assemblies can be encased to thereby provide smooth surfaces which are less traumatic to body tissue. Moreover, as shown in the figures, one or more spring assemblies 444 can be placed about and in apposition with load bearing structure.

Figure 108:
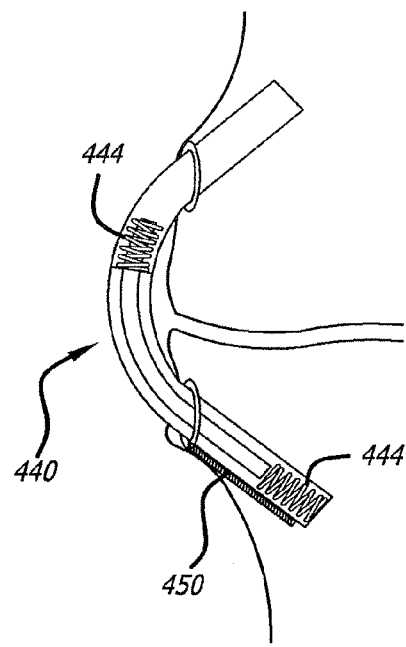
FIG. 108 is a cross-sectional view, depicting an alternate embodiment of a energy manipulation assembly incorporating piston support implanted within body anatomy.
Figure 109:
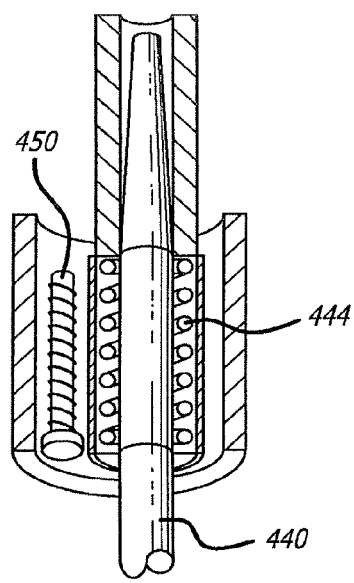
FIG. 109 is a cross-sectional view, depicting further substructure which may be incorporated into the assembly depicted in FIG. 108.

As best seen in FIGS. 108 and 109, the piston-type bearing assembly can further include an adjustment screw 450 arranged in a parallel fashion with respect to other energy absorbing structure to alter the effect of the same. Again, it is anticipated that such adjustment structure can be accessed percutaneously after the load bearing assembly is placed at or within a target tissue.

Figure 110:
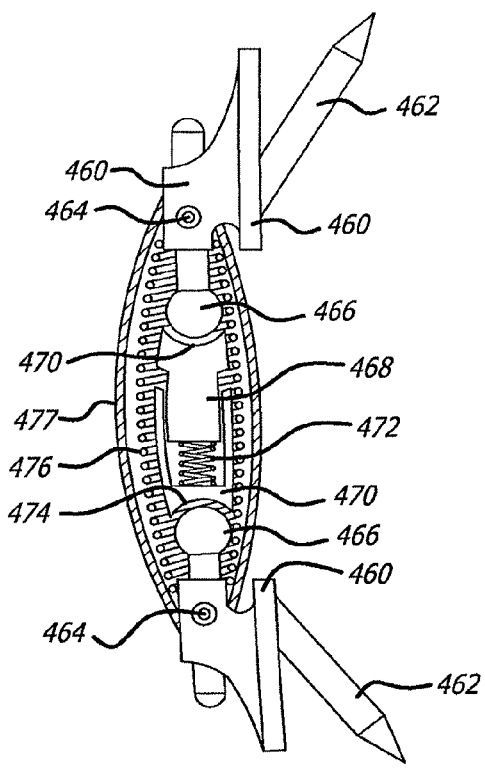
FIG. 110 is a cross-sectional view, depicting another embodiment of a energy manipulation assembly of the present invention incorporating piston support substructure.

Yet another embodiment of the present invention is disclosed in FIG. 110. In this assembly, a pair of spaced attachment assemblies 460 include projections 462 for engaging the tissue to be treated. The attachment assemblies 460 further each include locking side screws 464 as well as a rotatable access screw head 465 which operate to affect a longitudinal position (advancement and retraction) of a threaded shaft with a ball-tipped terminal end 466. Configured between the longitudinally spaced shafts 466 is a piston and cylinder assembly 468 having opposed ends 470 with a socket sized to receive the ball portion of the threaded shaft 466. A first spring 472 is contained within the cylinder 474 of the assembly. A second spring 476 is coaxially arranged about the threaded shafts 466 and piston and cylinder assembly 468. Further, a sheath 476 is placed about these subassemblies from one attachment assembly to another 460. Thus, this embodiment of a energy manipulation assembly provides both energy absorption as well as multi-dimensional translation to permit body anatomy articulation.

Yet further details of useful energy manipulation are disclosed in FIGS. 111-118. A bi-lateral energy manipulation assembly 480 includes a pair of laterally configured shafts 482, at the terminal ends of which are connected a single energy absorbing member 484. The energy absorbing member 484 can include a piston and spring assembly arranged and the shafts can extend a full width and length of the tissue being treated. Further, the laterally configured shafts 482 can include a longitudinally extending trough 486 employed to selectively engage complementary surfaces of the energy absorbing member assemblies 484. Also, as best seen in FIG. 112, tissue inserts 488 in the form of collars are contemplated to receive at least a portion of a length of the shafts 482. Such inserts 488 as well as other surfaces of the various disclosed embodiments and approaches can include a bone-ingrowth coating or texture.

Figure 116:
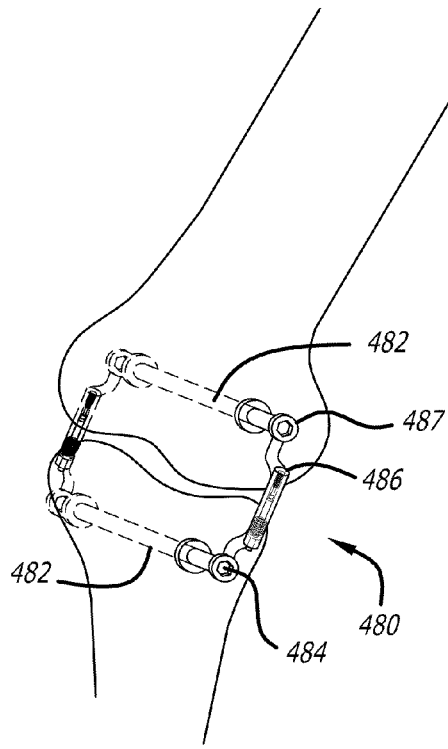

A related unilateral mounted device is shown in FIG. 116. In this approach, the shafts 482 extend less than a full width of the body anatomy but otherwise include a piston-based energy manipulation assembly 484. Once again, the members defining the piston assembly 484 can be sheathed with encasing structure 486 and can pivot about end points 488. The encasing structure 486 can be applied to various structures of the disclosed embodiments and can be formed from PTFE, ePTFE, Dacron, Polypropylene, Polyethylene, or woven materials such as silk. This structure 486 can also be created from bioabsorbable material and can be drug loaded or impregnated with silver or other agents capable of stimulation or reducing inflammation. The piston subassembly can further include a biasing spring 490 configured about a piston 492 and placed in a position with an internal cylindrical sleeve 494. Within the internal cylindrical sleeve 494 can be configured a further energy absorbing structure 496 such as a simple bending, columnar spring or a conventional helical spring (See FIGS. 117 and 118).

Figure 117:
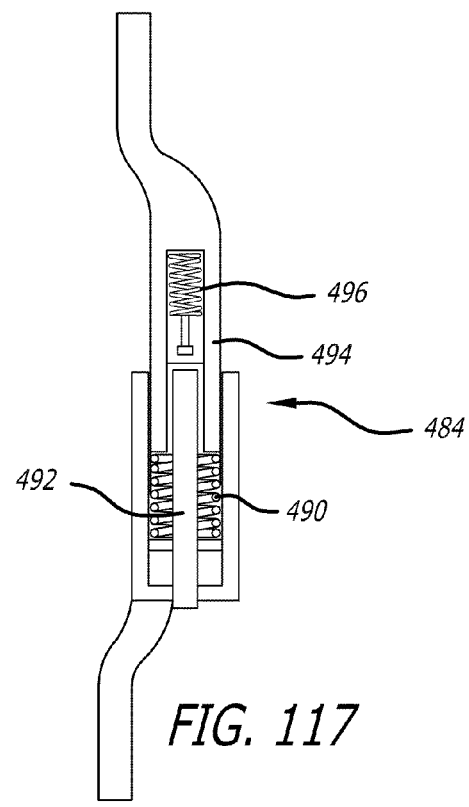

Moreover, with reference to FIG. 117, the piston subassembly 484 can include a platform 498, the position of which is adjustable by turning a central screw shaft 500. Again, it is contemplated that the screw shaft 500 be percutaneously accessed for ease of adjustment. Further, the dampening element can also involve a fluid-dampening system (FIGS. 117 and 118). Holes 502 formed in an end of position 492 effect a slow movement of fluid 504 through the assembly to prevent rapid changes in velocity.

Thus, the energy absorbing substructure 496 is engaged only at maximal compression of the assembly and at all other times remains free within the device.

Turning now to FIGS. 119-127, further embodiments of structure incorporating features of the present invention are depicted. In particular, the energy manipulation assembly 510 shown in FIGS. 119 and 120 includes first and second attachment structures 512, 514 having contours selected to match outer surfaces of body anatomy. An energy absorbing member 516 includes a pair of spaced ends each being pivotably attached to one attachment structure. The connection to the attachment structures 512, 514 as well as the energy absorption member 516 can further be sheathed in encasing structure 518 as described above. In this way, the overall structure assumes a low profile and generally atraumatic assembly which tends to cooperate with body anatomy.

In yet another approach (See FIG. 121), an energy manipulation assembly 520 of the present invention can incorporate into a first of a pair of attachment structures 522, 524 for mounting to body anatomy, an energy manipulation subassembly 526. Here, the attachment structure 522 includes a first end for mounting to body anatomy as well as a midsection employing a spring assembly 528 and a second end 530 including a slotted and cam assembly for engaging the second attachment structure.

Figure 122:
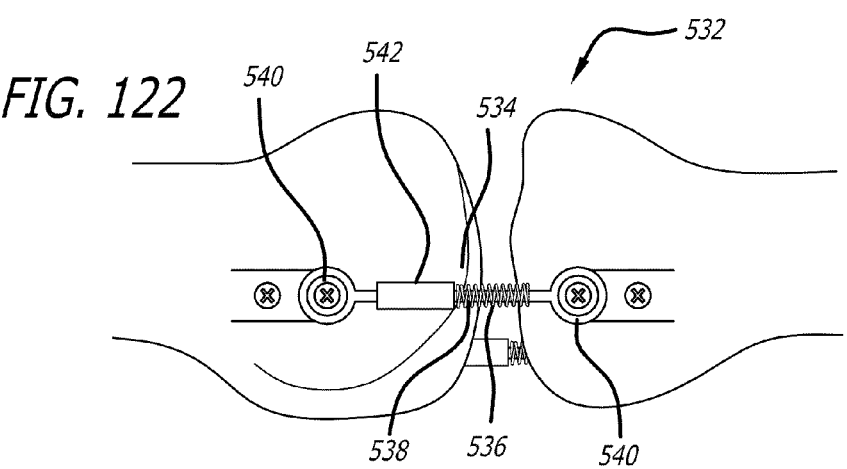
Figure 123:
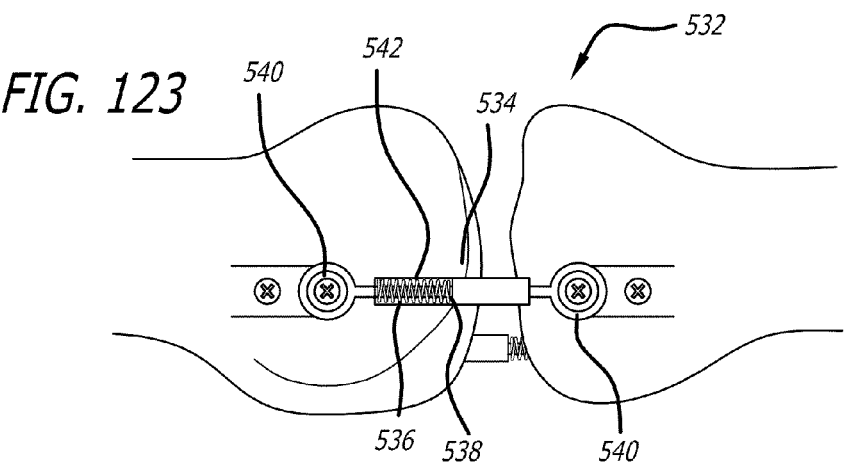
Figure 124:
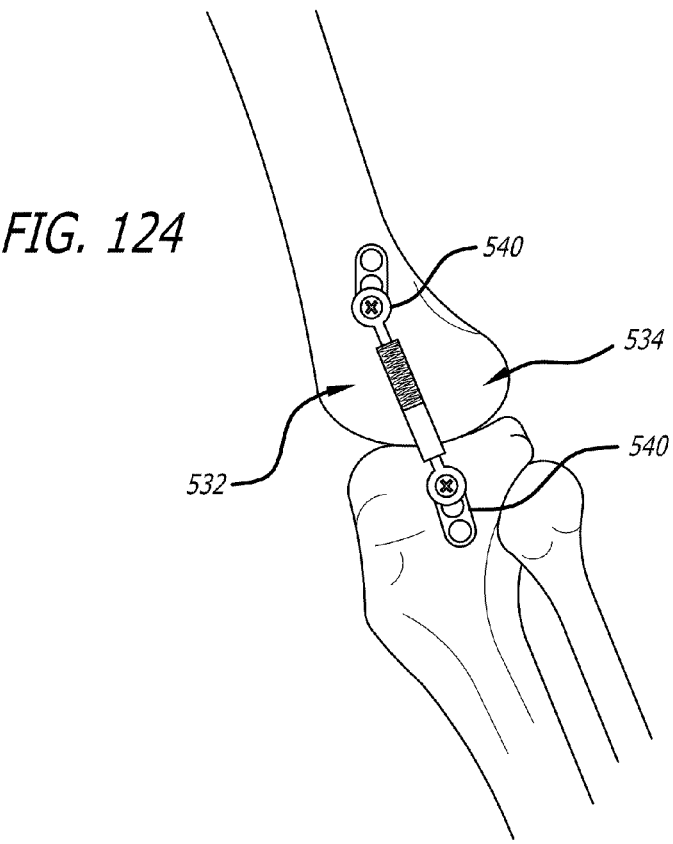
Figure 125:
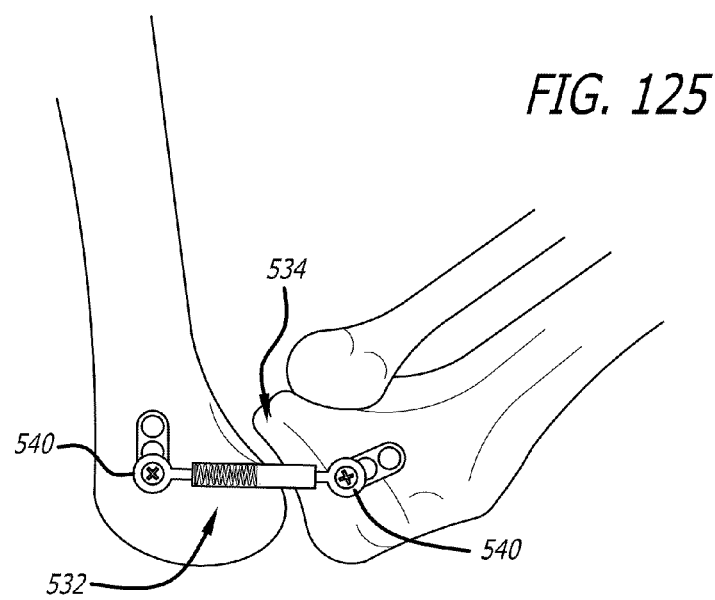

Other bilateral energy manipulation assemblies 532 incorporating spring subassemblies are shown in FIGS. 122 and 123. In each, pivoting structure is employed to connect energy manipulation assemblies 534 including springs 536 mounted about central rods 538, to body anatomy attachment structures 540. Again, in order to provide more atraumatic surfaces for contacting body tissue, portions of these approaches can be sheathed in encasing material 542. The manner in which such energy manipulation assemblies cooperate with the natural articulation of body joints is shown in FIGS. 124 and 125.

Figure 126:
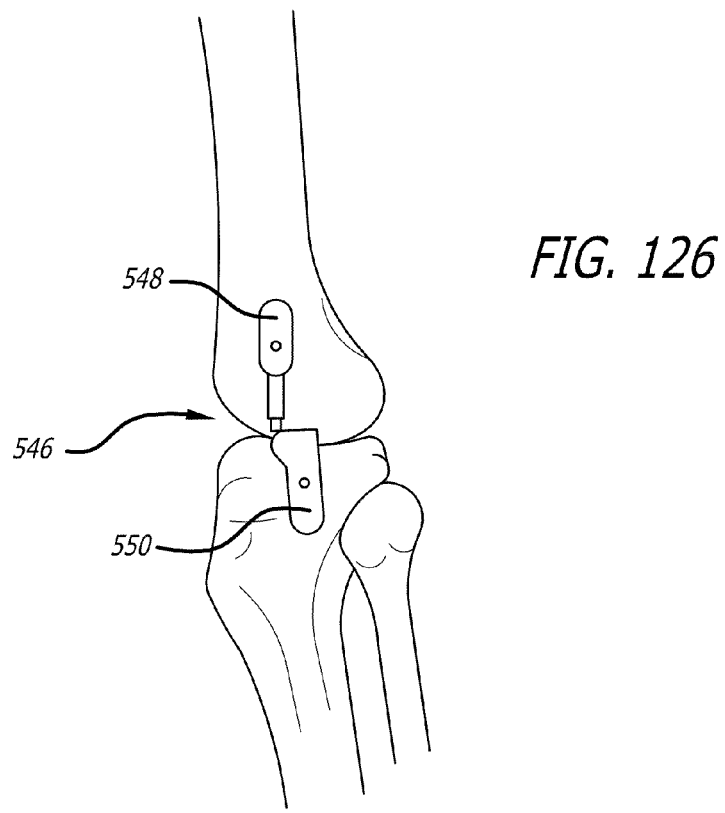
Figure 127:
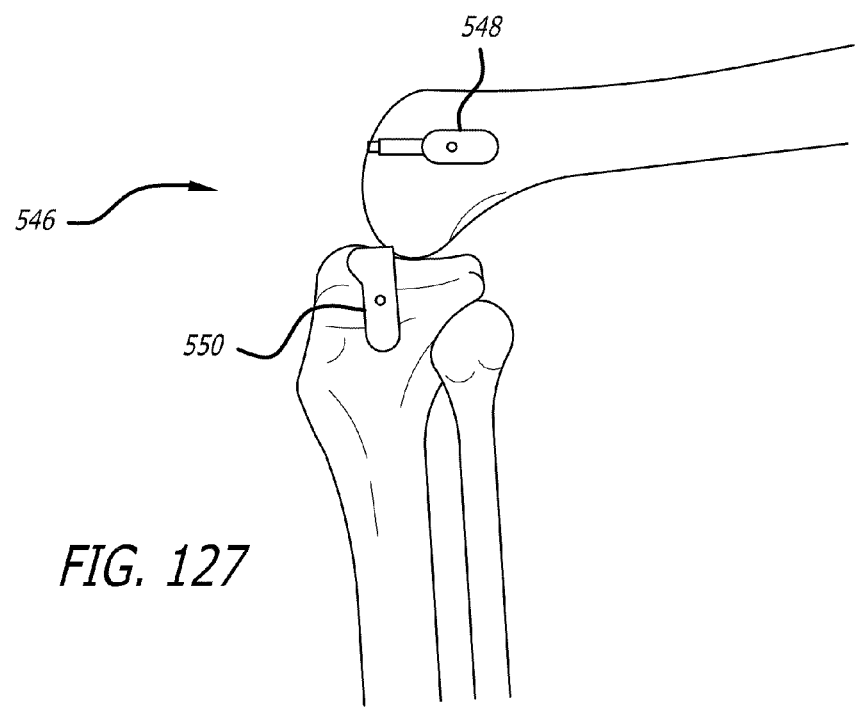

FIGS. 126 and 127 depict an approach where the energy manipulation assembly 546 includes a first part 548 and a second part 550, the first and second parts only engaging when the body anatomy approaches an aligned configuration. In this way, energy manipulation is achieved in tension but not in flexion.

Various further details of mounting or attachment structure are shown in FIGS. 128 and 129. Again, the present invention contemplates attachment structure 554 which follows the exterior contour of anatomy such as bones to which the attachment structure 554 is mounted. Moreover, such attachment structure 554 can extend longitudinally varying distances along the body anatomy. Furthermore, the contemplated attachment structures 556 can extend a substantial lateral distance along body anatomy as well as longitudinally to define various geometries. In one aspect, the attachment structures can assume a modified Y-shape.

With reference to FIG. 130, still yet a further embodiment of an energy manipulation assembly 560 incorporating various features of the present invention is shown. Configured between spaced attachment or body anatomy structures 562 is a complex energy absorption subassembly 564. An adjustment mechanism 566 can be affixed to one attachment structure 562 so that the degree of energy manipulation can be modified as needed. In the approach depicted, the adjustment mechanism 566 includes a slotted section 568 that receives a screw 570 which can be manipulated to allow the assembly to slide towards and away from the energy absorbing member 564. The energy absorbing member further includes a rotating, arcuate arm 572 which alternatively engages the attachment structure 562 having the adjustment subassembly 566, and a spring or otherwise biased projection 574. The various geometries and dimensions of the components of this approach are selected to accomplish desired load manipulation cooperating with natural articulation of the body anatomy being treated.

By way of example, the energy manipulation assembly 612 depicted in FIG. 131 could be employed to provide varying degrees of energy manipulation during a gait cycle and patient healing. The energy manipulation member 614 can include a spring 618 which slides within a slider 620 during normal motion. At first the spring 618 does not engage but at some point after implantation for example three weeks, a rotation tab 622 is locked within a slot 624. At that point, the sliding spring engages the tab 622 at key stages of gait and absorbs desired amounts of energy.

Turning to FIG. 132, yet a further contemplated embodiment is described. Here, an adjustable spring unit can be found within a base plate and joint elements are contemplated to be part of a replaceable unit. In that regard, a dovetail mating section 627 as well as a ball and socket joint 628 are placed between the energy manipulator 629 subassembly and one or more base assemblies 630.

Various different types of mounting screws are also contemplated to be used with this as well as other systems. Thus, there are at least two forms of screws, namely, a large thread design for a cancellous screw and a finer thread intended for denser cortical bone. The threads are orientated at opposing angles (~8 degrees) to anchor into a wedge of bone making removal of the plate through pull out very difficult. The heads of the screws are designed with the screw holes to ensure the correct trajectory of the screw. Installation of the screw will utilize a screw guide that initially locks into the screw hole on the plate thereby defining the desired trajectory and the screw is screwed into the bone through the screw guide which is then removed. Moreover, cortical screws can be angled as much forward toward an opposite cortex as possible without causing problems in the plate. The cancellous screws can be angled in such a way so as to grab hold of as much bone as possible.

As mentioned above, the present invention has applications to various parts of the body. As shown in FIGS. 132 and 133, an energy manipulation assembly 630 can be placed within the cavity 632 between the acromiom 634 and the humerus 636 bones. Although various approaches are contemplated, in one aspect the energy manipulation assembly can include a spring loaded body 638 between fixation points 640. A bearing surface 642 in the form of a ball bearing is further contemplated as is a spring compression adjustment subassembly 644.

In an application to the foot (See FIG. 134), an energy manipulation assembly 646 can be placed between the tibia 648 and the calcareous 650 bones to address problems with the ankle. Such an approach can help alleviate pain as well as address symptoms associated with a condition referred to as drop foot. Thus, the assembly 646 can be configured to accomplish a lifting motion on the foot.

Applications to the hand and finger are also contemplated (FIGS. 135 and 136). Here, one or more load manipulating assemblies 660 can be positioned between distal 662 and middle 664 phalanges as well as between middle 664 and proximal 666 phalanges. Moreover, distraction units 668 can be placed between adjacent phalanges 670 to treat various conditions.

Moreover, the present invention has applications to the spine (See FIGS. 137 and 138). Accordingly, a load sharing or energy manipulating device 680 can be attached to and placed between vertebra 682 to off-load a disc 684. The energy manipulation device 680 can be attached to the side of the vertebra 682 (FIG. 137) or can be affixed to facets (FIG. 138). Moreover, the device 680 (See FIG. 137) can include various of the previously described features such as adjustment nut 686 effecting the action of a shock absorber spring 688. A load transfer unit 690 can be further provided to include another spring 692 as well as adjustment nut 694. A pair of fixating components 696 are further provided for mounted to body tissue.

It is to be borne in mind that each of the disclosed various structures can be interchangeable with or substituted for other structures. Thus, aspects of each of the bending spring, cam engagement, segmented support and piston support assemblies can be employed across approaches. Moreover, the various manners of engaging energy absorbing structure with attachment structure and attachment structures to body anatomy can be utilized in each approach. Also, one or more of the various disclosed assemblies can be placed near a treatment site and at various angles with respect thereto. Pressure sensing and drug delivery approaches can also be implemented in each of the various disclosed embodiments.

Certain components of most embodiments of the present invention are designed for easy removal and, if necessary replacement while others are intended for permanent fixation. The permanent components are fixation components which have bony ingrowth promoting surfaces and are responsible for fixation of the system to the skeletal structure. The removable components include the mobile elements of the system such as the link members and/or the pivots or ball joints.

The advantages of this feature of the system include the ability to exchange key components of the system due to device failure, patient condition change or newer improved systems being available. Additionally if the patient subsequently requires further surgery the links may be removed to facilitate the additional procedure.

Further, certain of the contemplated mechanisms can be made to be completely disengaged mechanically and then brought into action under various conditions and during certain phases of the gait cycle. This discontinuous functionality—and the ability to tune that functionality to a particular patient's gait or pain is consequently a feature of the present invention.

Location of the permanent fixation components is important to fixation strength, ability to complete subsequent procedures, and location of pivots or ball joints. The fixation strength of the system, and therefore load bearing capacity, is dependent on the integrity of the bone onto which the component is fixed. To ensure strong fixation, in one embodiment, the fixation components span along the cortical bone and cancellous (or trabecular) bone. For example on the knee, the component would reside on the femoral shaft and extend down onto the trabecular bone on the end of the femur. Also, the system may utilize fixation on two cortical surfaces using through pins or bicortical screws.

A common joint procedure is joint replacement as previously described. The procedure of replacing a diseased joint includes resection of the surfaces of the joint and replacement with synthetic materials. To enable implantation of the energy absorbing system without impacting the potential to complete subsequent procedures (e.g., joint replacement) the permanent fixation components in a preferred embodiment are positioned at a location that does not compromise the total joint zone.

Many articulating joints are not simply pivot joints but involve complex multi-axis rotation and translation movements. To achieve its intended purpose, the energy absorber must accommodate these movements but also absorb and transfer energy during the required range of motion. To do so the joints on the device may be either in case A located at points on the bones of least motion, or in case B the joint mechanism must incorporate motion beyond simple uniaxial rotation or a combination of both.

In the case of A, the fixation components are positioned such that they orientate the attached device joint locations to preferred locations described by minimal or known motion characteristics. The device joint locations may be finely adjusted within a defined region on the fixation component to further optimize the device joint location. In the case of B) the device joint mechanism accommodates the positional changes and therefore can be placed on any distal point on the fixation component.

Therefore, the present invention provides a number of ways to treat body tissues and in particular, to absorb energy or manipulate forces to reduce pain. The present invention can be used throughout the body but have clear applications to articulating body structures such as joints.

Thus, it will be apparent from the foregoing that, while particular forms of the invention have been illustrated and described, various modifications can be made without parting from the spirit and scope of the invention.

We claim:

1. A method for treating a knee joint including a femur and a tibia, comprising:
   implanting a first base member directly in contact with the femur by placing the first base on the femur and securing the first base in place on the femur with a plurality of bone screws;
   implanting a second base member on the tibia; and
   configuring an energy manipulation structure between the first and second base members, wherein the energy manipulation structure includes proximal and distal articulating structures and at least one spring structure between the articulating structures;
   wherein the articulating structures are ball and socket joints.

2. The method of claim 1, wherein the articulating structures are replaceable.

3. The method of claim 1, further comprising placing a protective sheath over the articulating and spring structures.

4. The method of claim 1, wherein the method comprises attaching the bases only to one side of the knee joint.

5. The method of claim 1, wherein the first and second base members are attached to the bone by inserting bone screws through holes in the base members.

6. The method of claim 1, further comprising creating a tunnel under the patient's skin for the energy manipulation structure to be placed.

7. The method of claim 1, further comprising adjusting the energy manipulation structure between the first and second base components.

8. The method of claim 1, wherein the at least one spring structure is a metallic coil spring.

9. A method for treating a knee joint including a femur and a tibia, comprising:
   implanting a first base member directly in contact with the femur;
   implanting a second base member on the tibia by placing the second base on the tibia and securing the second base in place on the tibia with a plurality of bone screws; and
   configuring an energy manipulation structure between the first and second base members, wherein the energy manipulation structure includes at least one spring structure positioned between the first and second bases and configured to absorb a compressive load normally applied to the knee joint;
   wherein the at least one spring structure is a metallic coil spring.

10. The method of claim 9, wherein the method comprises attaching bases only to a medial side of the knee joint.

11. The method of claim 9, wherein the first and second base members are attached to the bone by inserting bone screws through holes in the base members.

12. The method of claim 9, wherein the bases and energy manipulation structure are placed under the patient's skin and outside of the joint capsule.

* * * * *